US008772295B2

(12) United States Patent
Mochly-Rosen et al.

(10) Patent No.: US 8,772,295 B2
(45) Date of Patent: *Jul. 8, 2014

(54) MODULATORS OF ALDEHYDE DEHYDROGENASE AND METHODS OF USE THEREOF

(71) Applicant: The Board of Trustees of the Leland Stanford Junior University, Palo Alto, CA (US)

(72) Inventors: Daria Mochly-Rosen, Menlo Park, CA (US); Che-Hong Chen, Fremont, CA (US); Wenjin Yang, Foster City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,106

(22) Filed: Jan. 22, 2013

(65) Prior Publication Data

US 2013/0267501 A1 Oct. 10, 2013

Related U.S. Application Data

(63) Continuation of application No. 12/581,704, filed on Oct. 19, 2009, now Pat. No. 8,389,522.

(60) Provisional application No. 61/225,827, filed on Jul. 15, 2009, provisional application No. 61/109,081, filed on Oct. 28, 2008.

(51) Int. Cl.
*A61K 31/495* (2006.01)
*C07D 261/02* (2006.01)

(52) U.S. Cl.
USPC ............ 514/248; 548/240; 544/233; 514/218

(58) Field of Classification Search
USPC .................... 514/248, 218; 544/233; 548/240
See application file for complete search history.

(56) References Cited

U.S. PATENT DOCUMENTS

| | | | |
|---|---|---|---|
| 2,319,808 A | 5/1943 | Fernholz et al. | |
| 5,260,323 A | 11/1993 | Baader et al. | |
| 5,374,605 A | 12/1994 | Hallenbach et al. | |
| 6,762,176 B1 | 7/2004 | Lassauniere et al. | |
| 6,780,883 B2 | 8/2004 | Booth et al. | |
| 6,900,338 B1 | 5/2005 | Haj-Yehia | |
| 6,939,882 B1 | 9/2005 | Cooke et al. | |
| 8,389,522 B2 * | 3/2013 | Mochly-Rosen et al. | .... 514/248 |
| 2002/0034783 A1 | 3/2002 | Meyers et al. | |
| 2002/0156281 A1 | 10/2002 | Booth et al. | |
| 2003/0100034 A1 | 5/2003 | Hunter | |
| 2004/0234622 A1 | 11/2004 | Muto et al. | |
| 2005/0171043 A1 | 8/2005 | Mochly-Rosen et al. | |
| 2005/0215548 A1 | 9/2005 | Wang et al. | |
| 2005/0215645 A1 | 9/2005 | Muto et al. | |
| 2006/0106051 A1 | 5/2006 | Dyckman et al. | |
| 2006/0173050 A1 | 8/2006 | Liu et al. | |
| 2008/0153926 A1 | 6/2008 | Mochly-Rosen et al. | |
| 2008/0200461 A1 | 8/2008 | Anderson et al. | |
| 2009/0082431 A1 | 3/2009 | Mochly-Rosen et al. | |
| 2009/0163545 A1 | 6/2009 | Goldfarb | |
| 2010/0113423 A1 | 5/2010 | Mochly-Rosen et al. | |
| 2012/0010248 A1 | 1/2012 | Mochly-Rosen et al. | |

FOREIGN PATENT DOCUMENTS

| | | |
|---|---|---|
| CN | 1749415 A | 3/2006 |
| EP | 1402887 | 3/2004 |
| EP | 1402888 | 3/2004 |
| EP | 2018863 | 1/2009 |
| JP | 1-203351 | 8/1989 |
| JP | 2-115168 | 4/1990 |
| JP | 6-321903 | 11/1994 |
| JP | 2009544742 A | 12/2009 |
| WO | WO99/23063 | 5/1999 |
| WO | WO99/32444 | 7/1999 |
| WO | WO99/54284 | 10/1999 |
| WO | WO01/32928 | 5/2001 |
| WO | WO02/22599 | 3/2002 |
| WO | WO02/053544 | 7/2002 |
| WO | WO03/007931 | 1/2003 |
| WO | WO03/030937 | 4/2003 |
| WO | WO03/064391 | 8/2003 |
| WO | WO03/086377 | 10/2003 |
| WO | WO2004/022523 | 3/2004 |
| WO | WO2005/014550 | 2/2005 |
| WO | WO2005/037782 A2 | 4/2005 |
| WO | WO2005/037792 A1 | 4/2005 |
| WO | WO2005/057213 | 6/2005 |
| WO | WO2005/007889 | 8/2005 |
| WO | WO2005/110422 | 11/2005 |
| WO | WO2007/034312 A2 | 3/2007 |

(Continued)

OTHER PUBLICATIONS

Moussa et al. CAS: 146: 337551, 2007.*
Weintraub et al. CAS: 143: 405804, 2005.*
Huisgen et al. CAS: 46: 45365, 1952.*
Chen et al., "Activation of aldehyde dehydrogenase-2 reduces ischemic damage to the heart", Science (Sep. 2008), 321(5895):1493-5.
Davis et al., "Requirement for Pax6 in corneal morphogenesis: a role in adhesion", J Cell Sci. (Jun. 2003), 116 (11):2157-67.
Gilman, et al., "Organometallic compounds in the Kolbe and Reimer-Tiemann reactions", Journal of Organic Chemistry (Jul. 1945), 10(4):374-379.
Nicoll-Griffith, "Stereoelectronic model to explain the resolution of enantiomeric ibuprofen amides on the Pirkle chiral stationary phase", Journal of Chromatography (Jul. 1987), 402:179-87.
STN: 11/16. 1984.

(Continued)

*Primary Examiner* — Rei-tsang Shiao
(74) *Attorney, Agent, or Firm* — Rudy J. Ng; Paula A. Borden; Bozicevic, Field & Francis LLP

(57) ABSTRACT

The present disclosure provides compounds that function as modulators of aldehyde dehydrogenase (ALDH) enzymatic activity, as well as compositions and formulations comprising the compounds. The present disclosure provides therapeutic methods involving administering a subject compound, or a subject pharmaceutical composition.

21 Claims, 25 Drawing Sheets

(56) References Cited

FOREIGN PATENT DOCUMENTS

| WO | WO2007/110237 |  | 10/2007 |
|---|---|---|---|
| WO | WO2008/002725 |  | 1/2008 |
| WO | WO2008/014497 | A2 | 1/2008 |
| WO | WO2008/021388 | A1 | 2/2008 |
| WO | WO2008/024497 |  | 2/2008 |
| WO | 2008112164 |  | 9/2008 |
| WO | WO2008112164 | * | 9/2008 |
| WO | WO2009/146555 |  | 12/2009 |
| WO | WO2009/156484 |  | 12/2009 |

OTHER PUBLICATIONS

Tracey, et al., "Product class 4: N-Arylalkanamides, ynamides, enamides, dienamides, and allenamides", Science of Sythesis (2005), 21:387-475.

U.S. Appl. No. 13/717,056, filed Dec. 17, 2012, Mochly-Rosen, et al.

Borgna et. al. "Preparation and Study of the Phytotoxic Activity of N-Aralkyl Substituted Amides", Il Farmaco; Edizione Scientifica, 1977, vol. 32, No. 11, pp. 813-826.

Budas, et. al., "Activation of Aldehyde Dehydrogenase 2 (ALDH2) Confers Cardioprotection in Protein Kinase C Epsilon (PKCε) Knockout Mice", Journal of Molecular and Cellular Cardiology, 2009, vol. 48, pp. 757-764.

Bukhitiarova, et al., "Structure and Anti-inflammatory Activity of Isonicotinic and Nicotine Amides", Pharmaceutical Chemistry Journal, 1997, vol. 31, No. 11, pp. 597-598.

Bukhitiarova, et al., "Possibilities for search for New Analagesics in the series of Arylamides of Isoniotinic and Nocotine Acids", Dopovidi Natsional'Noi Akademii Nauk Ukraini, 1998, No. 8, pp. 162-164.

Chen, et al., CAS:149:548594, 2008.

Cutshall, et. al., "Nicotinamide N-Oxides as CXCR2 Antagonists", Bioorganic & Medicinal Chemistry Letters, 2001, vol. 11, pp. 1951-1954.

Deng, et al., "Distinct Expression Levels and patterns of Stem Cell Marker, Aldehyde Dehydrogenase Isoform 1 (ALDH1), in Human Epithelial Cancers", PLoS One, 2010, vol. 5, No. 4, pp. 1-11.

Feng, et al., "Isolation and Characterization of Human Salivary Glands for Stem Cell Transplantation to Reduce Radiation-Induced Hyposalivation", Radiotherapy and Oncology, 2009, vol. 92, pp. 466-471.

Fernholz, et. al., "Stigmastadienone-22, 23-dibromide and related compounds", 1943, Accession No. 1943: 40468.

Furata et al. "Efficient Synthesis of Phenanthridinone Derivatives via Palladium-Catalyzed Coupling Process", Organic Letters, 2007, vol. 9, No. 2, pp. 183-186.

Goldfarb, "Method Using Lifespan-Altering Compounds for Altering the Lifespan of Eukaryotic Organisms, and Screening for Such Compounds", Accession No. 2009:846100.

Grigg, et al. "Synthesis of Cyclopropanes by Intramolecular Attack of N-Nucleophiles on the Central Carbon of (Π-Allyl)Palladium Complexes", Eur. J. Org. Chem. , 2001, vol. 4, pp. 707-712.

Hess, et al., "Functional Characterization of Highly Purified Human Hematopoietic Repopulating Cells Isolated According to Aldehyde Dehydrogenase Activity", Blood, 2004, vol. 104, No. 6, pp. 1648-1655.

Johnson, et al., "Metabolism, Excretion, and Pharmacokinetics of (3-{[4-Tert-Butylbenzy)-(Pyridine-3-sulfonyl)-Amino]-Methyl}-Phenoxy)-Acetic Acid, An Ep2recepto-Selective Prostaglandin E2 Agonist, In Male and Female Sprague-Dawley Rats", 2005, Drug Metabolism and Disposition, vol. 33, No. 8, pp. 1191-1201.

Katritzky, et al., "N-Oxides and Related Compounds. Part X. The Hydrogenation pd some Polyridine 1-oxides", 1958, J. Chem. Soc., pp. 1-18.

Konoplitskaya, et al. "Influence of Cycloprppylethyl-Containing Amines and amides of the Isoenzyme Forms of Rat Liver Aldehyde Dehydrogenase", 1994, vol. 28, No. 1, pp. 7-10.

Larson, et. al. "Disruption of the Coenzyme Binding Site and Dimer Interface Revealed in the Crystal Structure of Mitochondrial Aldehyde Dehydrogenase "Asian" Variant", The Journal of Biological Chemistry Investigation, 2006 vol. 116, No. 2, pp. 506-511.

Lombaert, et al., "Rescue of Salivary Gland Function after Stem Cell Transplantation in Irradiated Glands", PLoS ONE, 2008, vol. 3, No. 4, pp. 1-13.

Li et. al. "Mitochondrial Aldehyde Dehydrogenase-2 (ALDH2) Glu504Lys Polymorphism Contributes to the Variation in Efficacy of Sublingual Nitroglycerin", The Journal of Clinical Investigation, 2006, vol. 116, No. 2, pp. 506-511.

Nicoll-Griffith's CAS: 107: 141210, 1987.

Palacios, "Diuretic Action of New Sulfonamide Compounds", 1964, Arch. Inst. Farmacol. Exptl., vol. 16, No. 1, pp. 1-18.

Patani, et. al. "Bioisosterism: A Rational Approach to Drug Design", Chem. Rev., 1996, vol. 96, pp. 3146-3176.

Paruszewski, et al., "Anticonvulsant Activity of Benzylamides of Some Amino Acids and Heterocyclic Acids", Protein and Peptide and Peptide Letters, 2003, vol. 10, No. 5, pp. 475-482.

Perez-Miller, et al., "Alda-1 is an Agonist and Chemical Chaperone for the Common Human Aldehyde Dehydrogenase 2 Variant", Nat Struct Mol Biol, 2010, vol. 17, No. 2, pp. 159-164.

Registry (STN) [online], Apr. 24, 2001 (Searched date: Apr. 25, 2013) CAS Registry No. 332129-81-4.

Registry (STN) [online], Jul. 29, 2001 (Searched date: Apr. 25, 2013), CAS Registry No. 349438-38-6.

Registry (STN) [online], May 14, 2003 (Searched date: Apr. 25, 2013), CAS Registry No. 514816-37-6.

Registry (STN) [online], Aug. 1, 2001 (Searched date: Apr. 25, 2013), CAS Registry No. 349615-88-9.

Registry (STN) [online], Jan. 2, 2001 (searched date: Apr. 25, 2013), CAS Registry No. 312526-08-2.

Registry (STN) [online], Jul. 25, 2006 (Searched date: Apr. 25, 2013), CAS Registry No. 895680-72-5.

Registry (STN) [online], Jul. 25, 2006 (Searched date: Apr. 25, 2013), CAS Registry No. 895680-64-5.

Registry (STN) [online], Nov. 5, 2004 (Searched date: Apr. 25, 2013), CAS Registry No. 775317-15-2.

Registry (STN) [online], Jun. 7, 2004 (Searched date: Apr. 25, 2013), CAS Registry No. 690210-80-1.

Registry (STN) [online], Jul. 26, 2001 (Searched date: Apr. 25, 2013), CAS Registry No. 348604-08-0.

Registry (STN) [online], Apr. 2, 2004 (Searched date; Apr. 25, 2013), CAS Registry No. 670271-74-6.

Sato, et. al., "2-Hydroxymethylnicotinic Acid Lactone, 2-Hydroxymethylpyridine-3-acetic Acid Lactone, and Some of their Derivatives", Chem. Pharm. Bull., 1960, vol. 8, No. 5, pp. 427-435.

Satoh, et al. "Comparison of the Inhibitory Action of Synthetic Capsaicin Analogues with Various NADH-ubiquinone Oxidoreductases", Biochimica et Biophysica Acta, 1996, 1273(1) pp. 21-30.

Stella et. al., "Prodrug Strategies to Overcome Poor Water Solubility", Advanced Drug Delivery Reviews, 2007, vol. 59, pp. 677-694.

Williams et. al. Foye's Principals of Medicinal Chemistry. 5th edition, 2002, Chapter 2: "Drug Design and Relationship of Functional Groups to Pharmacologic Activity", pp. 59-63.

Zhang, et al. "Automation of Fluorous Solid-Phase Extraction for Parallel Synthesis", J. Comb. Chem. , 2006, vol. 8, pp. 890-896.

Himel, et al., "Fluorescent Analogs of Insecticides and Synergists. Synthesis and Reactions of Active-Site-Directed Fluorescent Probes", J. Agr. Food Chem., 1971, 19(6):1175-1180.

* cited by examiner

```
  1 mlraaarfgp rlgrrllsaa atqavpapnq qpevfcnqif innewhdavs rktfptvnps
 61 tgevicqvae gdkedvdkav kaaraafqlg spwrrmdash rgrlnriad lierdrtyla
121 aletldngkp yvisylvdld mvlkclryya gwadkyhgkt ipidgdffsy trhepvgvcg
181 qiipwnfpll mqawklgpal atgnvvvmkv aeqtplitaly vanlikeagf ppgvvnivpg
241 fgptagaaia shedvdkvaf tgsteigrvi qvaagssnik rvtleiggks pniimsdadm
301 dwaveqahfa lffnqgqccc agsrtfvqed iydefversv araksrvvgn pfdskteggp
361 qvdetqfkki lgyintgkqe gakllcgggi kdldkanyls tiakeeifgp
421 vmqilkfkti eevvgranns tyglaaavft kdldkanyls qalqagtvwv ncydvfgaqs
481 pfggykmsgs grelgeygiq aytevktvtv kvpqkns (SEQ ID NO:1)
```

FIG. 5A

```
  1 mlraaarfgp rlgrrllsaa atqavpapnq qpevfcnqif innewhdavs rktfptvnps
 61 tgevicqvae gdkedvdkav kaaraafqlg spwrrmdash rgrlnriad lierdrtyla
121 aletldngkp yvisylvdld mvlkclryya gwadkyhgkt ipidgdffsy trhepvgvcg
181 qiipwnfpll mqawklgpal atgnvvvmkv aeqtplitaly vanlikeagf ppgvvnivpg
241 fgptagaaia shedvdkvaf tgsteigrvi qvaagssnik rvtleiggks pniimsdadm
301 dwaveqahfa lffnqgqccc agsrtfvqed iydefversv araksrvvgn pfdskteggp
361 qvdetqfkki lgyintgkqe gakllcgggi kdldkanyls tiakeeifgp
421 vmqilkfkti eevvgranns tyglaaavft kdldkanyls qalqagtvwv ncydvfgaqs
481 pfggykmsgs grelgeygiq aytkvktvtv kvpqkns (SEQ ID NO:2)
```

FIG. 5B

```
  1 msssgtpdlp viltdlkiqy tkifinnewh dsvsgkkfpv fnpateeelc qveegdkedv
 61 dkavkaarga fqigspwrtm dasergrlly kiadlierdr lliatmesmn ggklysnayl
121 sdiagciktl rycagwadki qgrtipidgn fftytrhepi gvcgqiipwn fplvmliwki
181 gpalscgntv vvkpaeqtpl talhvaslik eagfppgvvn ivpgygptag aaisshmdid
241 kvaftgstev gklikeaagk snikrvtlel ggkspcivla dadldnavef ahhgvfyhqg
301 qcciaasrif veesiydefv rrsverakky ilgnpitpgv tqgpqidkeq ydkildlies
361 gkkegaklec gggpwgnkgy fvqptvfsnv tdemriakee ifgpvqqimk fksiddvikr
421 anntfyglsa gvftkdidka itissaiqag tvwvncygvv saqcpfggfk msgngreige
481 ygfheytevk tvtvkisqkn s (SEQ ID NO:3)
```

FIG. 6A

```
  1 msssgtpdlp viltdlkiqy tkifinnewh dsvsgkkfpv fnpateeelc qveegdkedv
 61 dkavkaarga fqigspwrtm dasergrlly kiadlierdr lliatmesmn ggklysnayl
121 ndiagciktl rycagwadki qgrtipidgn fftytrhepi gvcgqiipwn fplvmliwki
181 gpalscgntv vvkpaeqtpl talhvaslik eagfppgvvn ivpgygptag aaisshmdid
241 kvaftgstev gklikeaagk snikrvtlel ggkspcivla dadldnavef ahhgvfyhqg
301 qcciaasrif veesiydefv rrsverakky ilgnpitpgv tqgpqidkeq ydkildlies
361 gkkegaklec gggpwgnkgy fvqptvfsnv tdemriakee ifgpvqqimk fksiddvikr
421 anntfyglsa gvftkdidka itissaiqag tvwvncygvv saqcpfggfk msgngreige
481 ygfheytevk tvtvkisqkn s (SEQ ID NO:4)
```

FIG. 6B

```
  1 mskiseavkr apaafssgrt rplqfriqql ealqrliqeq eqelvgalaa dihknewnay
 61 yeevvvlee ieymiqkipe waadepvekt pqtqqdeiyi hsepigvvlv igtwnypfni
121 tiqpmvgaia agnsvvlkps elsenmasil atiipqyidk dlypvinggv petteilker
181 fdhilytgst gvqkiimtaa akhltpvtie lggkspcyvd kncdidvacr riawgkfmns
241 gqtcvapdyi lcdpsiqnqi veklkkslke fygedakksr dygriisarh fqrvmglieg
301 qkvayggtgd aatryiapti itdvdpqspv mqeeifgpvi pivcvrslee aiqfinqrek
361 plalymfssn dkvikkmiae tssgvaand vivhitlhsl pfggvgnsgm gsyhgkksfe
421 tfshrrsciv rplmndeglk vryppspakm tqh (SEQ ID NO:5)
```

FIG. 7

```
  1 matciwirsc garrlgstfp gcrlrpragg lvpasgpapg paqlrcyagr lagisaailr
 61 tdsfvggrwl paaatfpvqd pasgaalgmv adcgvreara avraayeafc rwrevsaker
121 ssilrkwynl miqnkddiar iitaesgkpl keahgeilys afflewfsee arrvygdiih
181 tpakdrraiv lkqpigvaav itpwnfpsam itrkvgaala agctvvvkpa edtpfsaial
241 aelasqagip sgvynvipcs rknakevgea ictdplivski sftgstttgk illhhaansv
301 krvsmeiggl apfivfdsan vdqavagama skfrntgqtc vcsnqfivqr gihdafvkaf
361 aeamkknlrv gngfeegttq gpliinekave kvekqvndav skgatvvtgg krhqlgknff
421 eptlicnvtq dmlctheetf gplapvikfd teeeaiaian aadvglagyf ysqdpaqiwr
481 vaeqlevgmv gvneglissv ecpfggvkqs gigregskyg ideyieikyv cyggl (SEQ ID NO:6)
```

MODULATORS OF ALDEHYDE DEHYDROGENASE AND METHODS OF USE THEREOF

CROSS-REFERENCE

This application claims the benefit of U.S. Provisional Patent Application No. 61/109,081, filed Oct. 28, 2008, and U.S. Provisional Patent Application No. 61/225,827, filed Jul. 15, 2009, which applications are incorporated herein by reference in their entirety.

STATEMENT REGARDING FEDERALLY SPONSORED RESEARCH

This invention was made with Government support under contract number AA11147 awarded by the National Institutes of Health. The Government has certain rights in this invention.

BACKGROUND

Aldehyde dehydrogenases (ALDH) constitute a family of enzymes that play a critical role in detoxification of various cytotoxic xenogenic and biogenic aldehydes. There are at least 19 members/isozymes of the ALDH family, where the various isozymes may exhibit different substrate specificity and/or cellular location relative to other members of the family.

Cytotoxic aldehydes derive from a variety of sources. For example, environmental (external) sources of aldehydes include those that result from ethanol consumption, from consumption of food sources, from ingestion of hazardous materials such as vinyl chloride, pesticides, herbicides, etc., or from inhalation of hazardous materials such as those found in cigarette smoke, industrial pollution, etc. Aldehydes that may be cytotoxic can also be produced biologically (e.g., endogenously), e.g., as a result of oxidative stress such as occurs in ischemia, irradiation, or metabolism or bioconversion of cellular precursors such as neurotransmitters and drugs. Accumulation of cytotoxic levels of aldehydes, and/or defects in the ALDH enzyme, has been implicated in a variety of diseases and conditions, or in increased risk of disease development. The range of implicated diseases includes neurodegenerative diseases, aging, cancer, myocardial infarction, stroke, dermatitis, diabetes, cataracts, and liver diseases.

There is a need in the art for agents that modulate ALDH enzymatic activity.

Literature

U.S. Patent Publication No. 2008/0153926; WO 2008/122164.

SUMMARY OF THE INVENTION

The present disclosure provides compounds that function as modulators of aldehyde dehydrogenase (ALDH) enzymatic activity, as well as compositions and formulations comprising the compounds. The present disclosure provides therapeutic methods involving administering a subject compound, or a subject pharmaceutical composition.

BRIEF DESCRIPTION OF THE DRAWINGS

FIG. 5A and FIG. 5B provide the amino acid sequence of human ALDH2 (SEQ ID NO:1) and the amino acid sequence of an E487K variant of human ALDH2 (SEQ ID NO:2), respectively.

FIGS. 6A and 6B provide exemplary ALDH1 amino acid sequences.

FIG. 7 provides an exemplary ALDH3 amino acid sequence.

FIG. 12 provides an exemplary ALDH5 amino acid sequence.

DEFINITIONS

Figure 1:
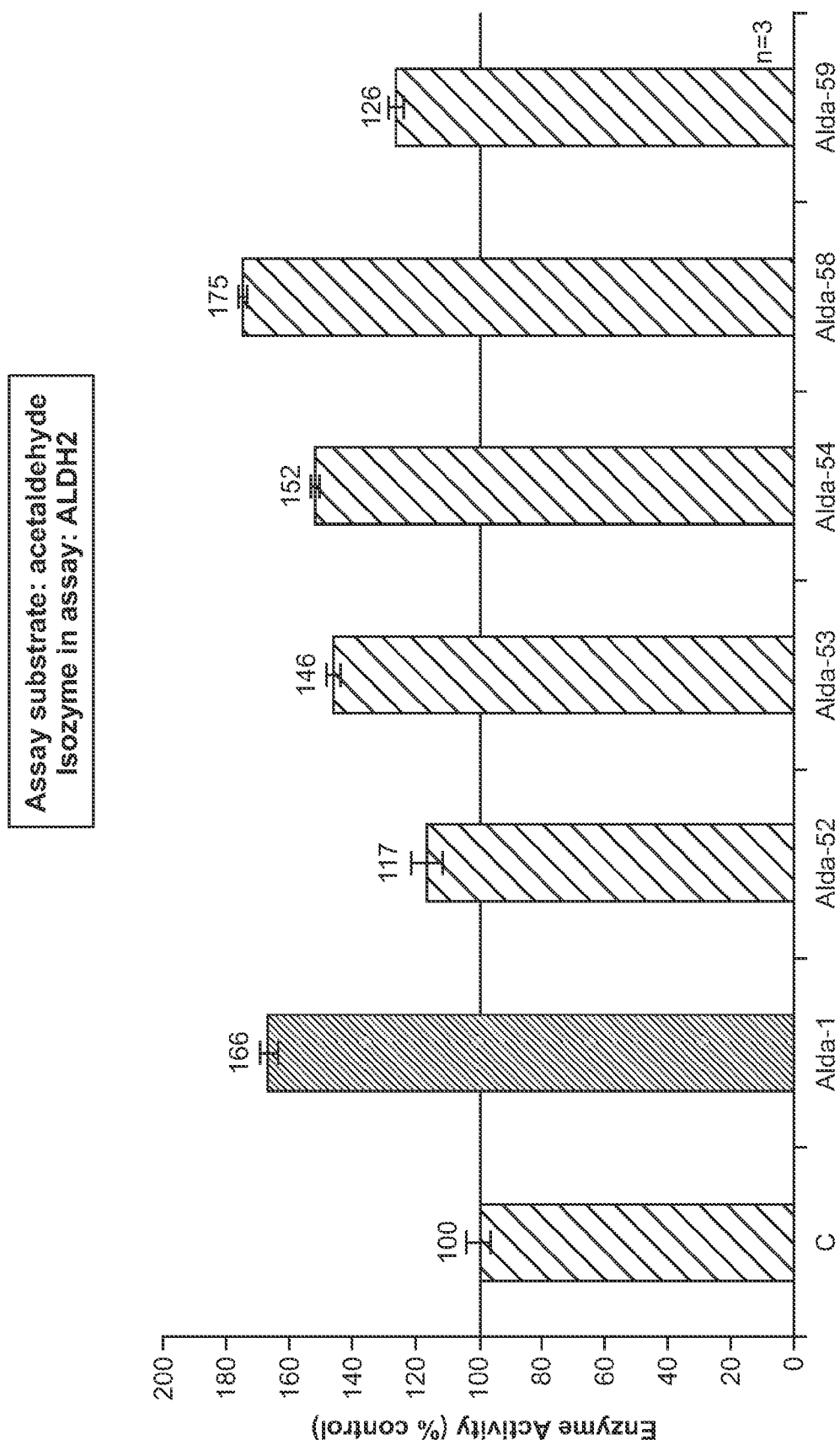
FIGS. 1-3 depict the effect of exemplary compounds on enzymatic activity of ALDH2.
Figure 2:
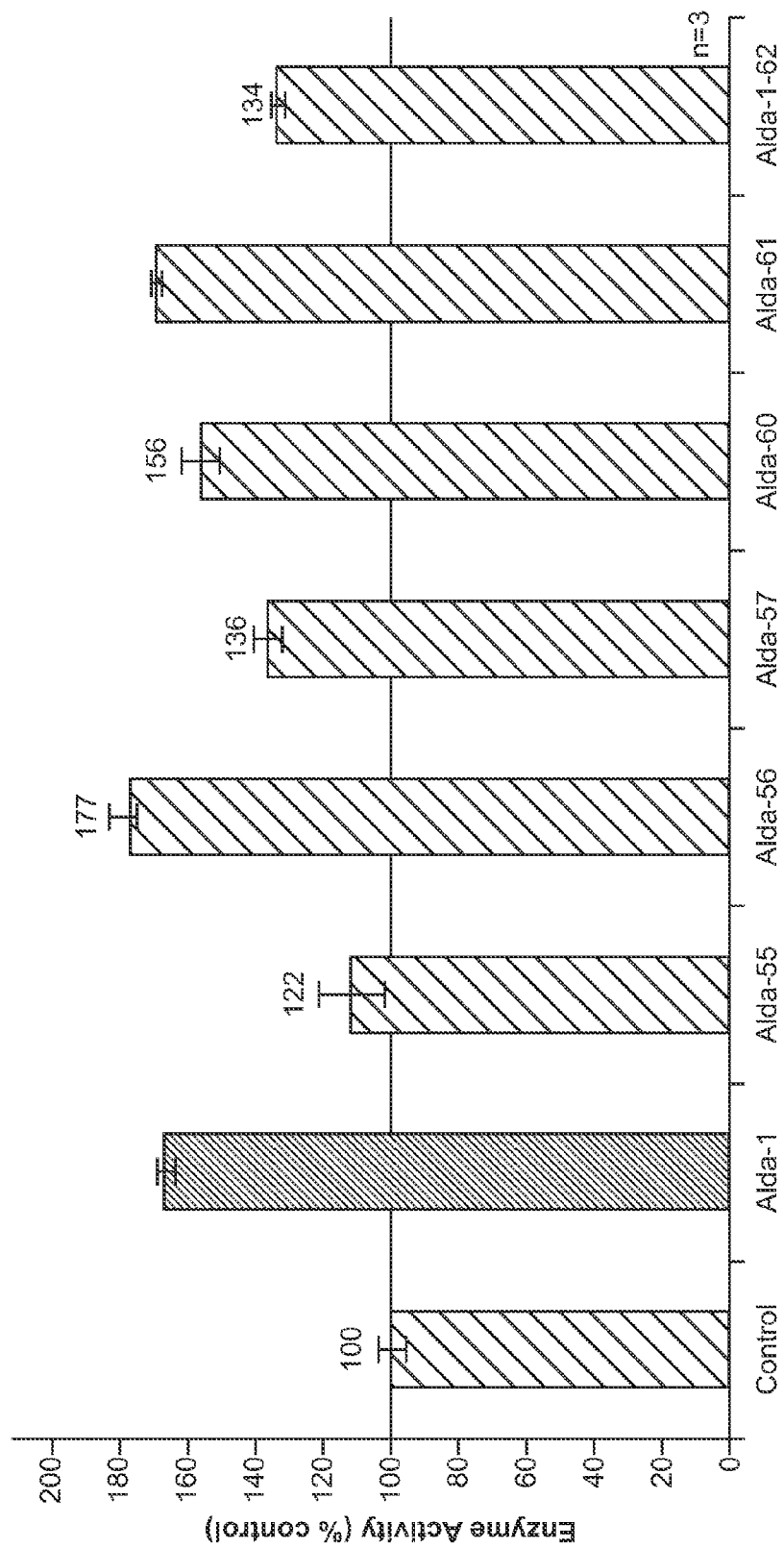
Figure 3:
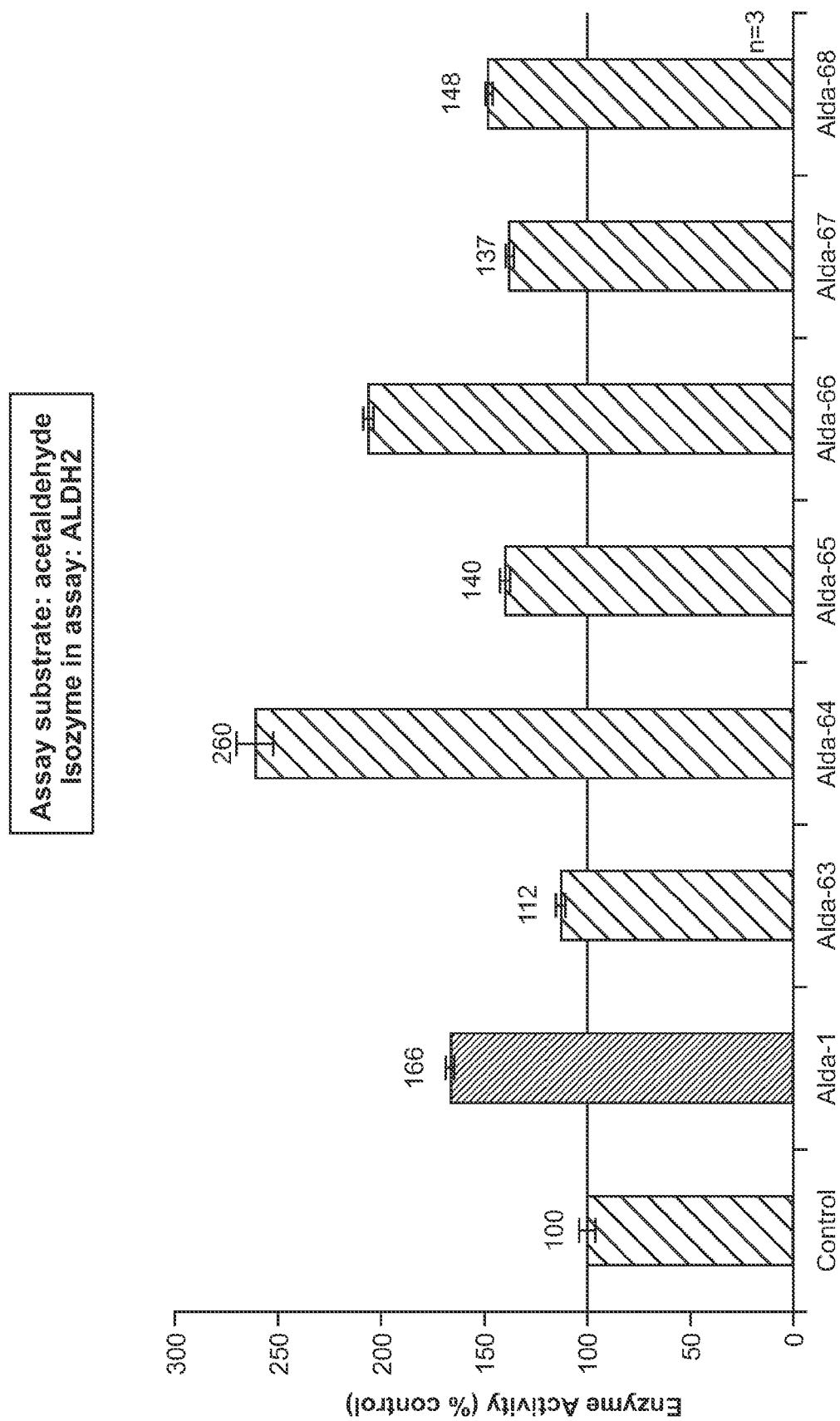

As used herein, the term "aldehyde dehydrogenase" or "ALDH" refers to an enzyme that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent or an $NADP^+$-dependent reaction. For example, ALDH oxidizes aldehydes derived from the breakdown of compounds, e.g., toxic compounds that are ingested, that are absorbed, that are inhaled, that are produced as a result of oxidative stress, or that are produced during normal metabolism, e.g., conversion of retinaldehyde to retinoic acid. An example of a biogenic aldehyde is acetaldehyde produced as a product of alcohol dehydrogenase activity on ingested ethanol. An aldehyde dehydrogenase can also exhibit esterase activity and/or reductase activity.

The term "ALDH" encompasses ALDH found in the cytosol, in the mitochondria, microsome, or other cellular compartment. The term "ALDH" encompasses ALDH found primarily in one or a few tissues, e.g., cornea, saliva, liver, etc., or in stem cells and embryos. The term "ALDH" encompasses any of the known ALDH isozymes, including ALDH1, ALDH2, ALDH3, ALDH4, ALDH5, etc.

As used herein, the term "mitochondrial aldehyde dehydrogenase-2" or "ALDH2" refers to an enzyme that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent reaction. For example, ALDH2 oxidizes aldehydes derived from the breakdown of compounds, e.g., toxic compounds that are ingested, that are absorbed, that are inhaled, or that are produced during normal metabolism. Mitochondrial ALDH2 is naturally found in mitochondria.

The term "ALDH2" encompasses ALDH2 from various species. Amino acid sequences of ALDH2 from various species are publicly available. For example, a human ALDH2 amino acid sequence is found under GenBank Accession Nos. AAH02967 and NP_000681; a mouse ALDH2 amino acid sequence is found under GenBank Accession No. NP_033786; and a rat ALDH2 amino acid sequence is found under GenBank Accession No. NP_115792. The term "ALDH2" encompasses an aldehyde dehydrogenase that exhibits substrate specificity, e.g., that preferentially oxidizes aliphatic aldehydes. The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1 or SEQ ID NO:2.

The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. An example of an ALDH2 variant is an ALDH2 polypeptide that comprises a Glu-to-Lys substitution at amino acid position 487 of mature human ALDH2, as depicted in FIG. 5B (amino acid 504 of SEQ ID NO:2), or at a position corresponding to amino acid 487 of human ALDH2. This mutation is referred to as the "E487K mutation"; the "E487K variant"; or as the "Glu504Lys polymorphism". See, e.g., Larson et al. (2005) *J. Biol. Chem.* 280: 30550; and Li et al. (2006) *J. Clin. Invest.* 116:506. An ALDH2 variant retains at least about 1% of the enzymatic activity of a corresponding wild-type ALDH2 enzyme. For example, the E487K variant retains at least about 1% of the activity of an enzyme comprising the amino acid sequence depicted in FIG. 5A (SEQ ID NO:1). "ALDH2" includes an enzyme that converts acetaldehyde into acetic acid, e.g., where the acetaldehyde is formed in vivo by the action of alcohol dehydrogenase on ingested ethanol.

As used herein, "ALDH1" refers to a cytosolic aldehyde dehydrogenase that oxidizes an aldehyde (e.g., a xenogenic aldehyde, a biogenic aldehyde, or an aldehyde produced from a compound that is ingested, inhaled, or absorbed) to its corresponding acid in an $NAD^+$-dependent reaction.

The term "ALDH1" encompasses ALDH1 from various species. Amino acid sequences of ALDH1 from various species are publicly available. See, e.g., GenBank Accession Nos. AAC51652 (*Homo sapiens* ALDH1); NP_000680 (*Homo sapiens* ALDH1); AAH61526 (*Rattus norvegicus* ALDH1); AAI05194 (*Bos taurus* ALDH1); and NP_036051 (*Mus musculus* ALDH1). The term "ALDH1" as used herein also encompasses fragments, fusion proteins, and variants (e.g., variants having one or more amino acid substitutions, addition, deletions, and/or insertions) that retain ALDH1 enzymatic activity. The term "ALDH1" encompasses an aldehyde dehydrogenase that oxidizes aromatic aldehydes, including those of the retinaldehyde, naphthaldehyde, phenanthrenealdehyde, and coumarinaldehyde series, as well as complex polyaromatic aldehydes. The term "ALDH1" encompasses a cytosolic aldehyde dehydrogenase.

The term "ALDH1" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in SEQ ID NO:3 or SEQ ID NO:4 (depicted in FIGS. 6A and 6B, respectively).

The term "ALDH3" encompasses ALDH3 from various species. Amino acid sequences of ALDH3 from various species are publicly available. See, e.g., GenBank Accession Nos. AAB26658 (*Homo sapiens* ALDH3), NP_000683 (*Homo sapiens* ALDH3), P30838 (*Homo sapiens* ALDH3), NP_001106196 (*Mus musculus* ALDH3), and AAH70924 (*Rattus norvegicus* ALDH3). The term "ALDH3" as used herein also encompasses fragments, fusion proteins, and variants (e.g., variants having one or more amino acid substitutions, addition, deletions, and/or insertions) that retain ALDH3 enzymatic activity. The term "ALDH3" encompasses an aldehyde dehydrogenase that exhibits specificity toward aromatic aldehydes, e.g., oxidizing aromatic aldehydes of the 2-naphthaldehyde series, but inactive toward 1-naphthaldehydes and higher polyaromatic aldehydes. The term "ALDH3" encompasses an aldehyde dehydrogenase that can use both $NAD^+$ and $NADP^+$ as co-substrate. The term "ALDH3" encompasses aldehyde dehydrogenase found naturally in the stomach, in the lung, in saliva, and in the cornea.

The term "ALDH3" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in SEQ ID NO:5 (as depicted in FIG. 7).

The term "ALDH5" (also referred to as "succinic semialdehyde dehydrogenase") encompasses an $NAD^+$-dependent enzyme that oxidizes succinic semialdehyde to succinate. ALDH5 is involved in the catabolism of 4-aminobutyric acid (GABA). Naturally-occurring ALDH5 can be found in the mitochondria of eukaryotic cells. The term "ALDH5" encompasses an enzymatically active polypeptide having at least about 75%, at least about 80%, at least about 85%, at least about 90%, at least about 95%, at least about 98%, at least about 99%, or 100%, amino acid sequence identity to the amino acid sequence set forth in FIG. 12 (SEQ ID NO:6).

The term "isolated compound" means a compound which has been substantially separated from, or enriched relative to, other compounds with which it occurs in nature. Isolated compounds are at least about 80%, at least about 90% pure, at least about 98% pure, or at least about 99% pure, by weight. The present disclosure is meant to comprehend diastereomers as well as their racemic and resolved, enantiomerically pure forms and pharmaceutically acceptable salts thereof.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The terms "subject," "individual," and "patient" are used interchangeably herein to a member or members of any mammalian or non-mammalian species that may have a need for the pharmaceutical methods, compositions and treatments described herein. Subjects and patients thus include, without limitation, primate (including humans and non-human primates), canine, feline, ungulate (e.g., equine, bovine, swine (e.g., pig)), avian, and other subjects. Humans and non-human mammals having commercial importance (e.g., livestock and domesticated animals) are of particular interest.

"Mammal" refers to a member or members of any mammalian species, and includes, by way of example, canines; felines; equines; bovines; ovines; rodentia, etc. and primates, e.g., humans. Non-human animal models, particularly mammals, e.g. a non-human primate, a murine (e.g., a mouse, a rat), lagomorpha, etc. may be used for experimental investigations.

"In combination with," or "co-administration," as used herein, in the context of administering a first compound and at least a second compound, refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to one or more of the generic formulas shown below in vivo when such prodrug is administered to a mammalian subject. Prodrugs of a compound of one or more of the generic formulas shown below are prepared by modifying functional groups present in the compound of the generic formula in such a way that the modifications may be cleaved in vivo to release the parent compound. Prodrugs include compounds of one or more of the generic formulas shown below wherein a hydroxy, amino, or sulfhydryl group in one or more of the generic formulas shown below is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of one or more of the generic formulas shown below, and the like.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom-ethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings.

Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

A subject compound may possess one or more asymmetric centers; such compounds can therefore be produced as individual (R)— or (S)— stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an ALDH agonist" includes a plurality of such agonists and reference to "the formulation" includes reference to one or more formulations and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compounds that function as modulators of aldehyde dehydrogenase (ALDH) enzymatic activity, as well as compositions and formulations comprising the compounds. The present disclosure provides therapeutic methods involving administering a subject compound, or a subject pharmaceutical composition.

Agonists of ALDH (e.g., ALDH1, ALDH2, ALDH3, ALDH4, ALDH5, etc.) are useful for treating a variety of disorders, including, e.g., conditions involving ischemic stress, oxidative stress, chronic free-radical associated diseases, acute free-radical associated diseases, insensitivity to nitroglycerin (e.g., in angina and heart failure), hypertension, peripheral artery disease, diabetes, cataract, age-related macular degeneration, lung diseases that result from cigarette smoking, cancer, neurodegenerative diseases, ethanol intolerance, and osteoporosis.

Agonists of ALDH can also be used to modulate embryogenesis, stem cell regeneration, development, and differentiation. Agonists of ALDH can also be used for various skin treatments. Agonists of ALDH are also useful for reducing the level in an individual of a compound such as ethanol, methanol, ethylene glycol monomethyl ether, polyvinyl chloride, xenogenic aldehydes, and biogenic aldehydes. Agonists of ALDH are useful for reducing the level of an aldehyde in an individual, where the aldehyde is ingested, inhaled, or absorbed, or where the aldehyde is formed in vivo from an ingested, inhaled, or absorbed compound, where ALDH agonist reduces the level of the aldehyde to below a toxic level. Agonists of ALDH are also useful for reducing the level in an individual of a compound that, when ingested, absorbed, or inhaled, gives rise to an aldehyde substrate for ALDH. The present disclosure provides therapeutic methods involving administering a subject compound, or a subject pharmaceutical composition.

Modulators of Aldehyde Dehydrogenase

The present disclosure provides compounds that function as modulators of ALDH enzymatic activity; and pharmaceutical compositions comprising the compounds. Modulators include agonists (also referred to herein as "activators").

In some embodiments, individuals to be treated are humans. In some embodiments, a human to be treated according to a subject method is one that has two "wild-type" ALDH2 alleles, e.g., the ALDH2 encoded by the two wild-type ALDH2 alleles has a glutamic acid at position 487 of the mature protein (amino acid 504 of the protein including the leader peptide), as depicted in FIG. 5A. In other embodiments, a human to be treated according to a subject method is one that has one or two "ALDH2*2" alleles, e.g., the ALDH2 encoded by one or both ALDH2 alleles comprises a lysine as amino acid position 487 of the mature protein (amino acid 504 of the protein including the leader peptide), as depicted in FIG. 5B. The E487K polymorphism is a semidominant polymorphism, and results in an ALDH2 tetramer that has significantly lower enzymatic activity than "wild-type" ALDH2. Thus, individuals who are heterozygous or homozygous for the ALDH2*2 allele have much lower in vivo ALDH2 activity levels than individuals who are homozygous for the "wild-type" ALDH2 allele. Individuals who are heterozygous or homozygous for the ALDH2*2 allele are expected to benefit from treatment with a subject ALDH2 agonist, because the level of ALDH2 activity in such individuals is particularly low, and any increase of ALDH2 activity levels would be expected to provide a therapeutic effect. Any increase in ALDH2 activity would be beneficial in treating conditions such as ischemic disorders, in increasing the responsiveness of such individuals to nitroglycerin, etc., as discussed in more detail below.

In some embodiments, a subject ALDH agonist selectively modulates (e.g., increases) an enzymatic activity of a particular ALDH isozyme. For example, in some embodiments, a subject ALDH agonist selectively increases an enzymatic activity of ALDH1. For example, in some embodiments, a subject ALDH agonist increases an enzymatic activity of ALDH1, but does not substantially increase the same enzymatic activity of an ALDH isozyme other than ALDH1, e.g., the ALDH agonist increases an enzymatic activity of an ALDH isozyme other than ALDH1, if at all, by no more than about 15%, e.g., by less than 15%, less than 10%, less than 5%, or less than 1%.

In some embodiments, a subject ALDH agonist selectively modulates (e.g., increases) an enzymatic activity of ALDH2. For example, in some embodiments, a subject ALDH agonist increases an enzymatic activity of ALDH2, but does not substantially increase the same enzymatic activity of an ALDH isozyme other than ALDH2, e.g., the ALDH agonist increases an enzymatic activity of an ALDH isozyme other than ALDH2, if at all, by no more than about 15%, e.g., by less than 15%, less than 10%, less than 5%, or less than 1%.

In some embodiments, a subject ALDH agonist selectively modulates (e.g., increases) an enzymatic activity of ALDH3. For example, in some embodiments, a subject ALDH agonist increases an enzymatic activity of ALDH3, but does not substantially increase the same enzymatic activity of an ALDH isozyme other than ALDH3, e.g., the ALDH agonist increases an enzymatic activity of an ALDH isozyme other than ALDH3, if at all, by no more than about 15%, e.g., by less than 15%, less than 10%, less than 5%, or less than 1%.

In some embodiments, a subject ALDH agonist selectively modulates (e.g., increases) an enzymatic activity of ALDH5. For example, in some embodiments, a subject ALDH agonist increases an enzymatic activity of ALDH5, but does not substantially increase the same enzymatic activity of an ALDH isozyme other than ALDH5, e.g., the ALDH agonist increases an enzymatic activity of an ALDH isozyme other than ALDH5, if at all, by no more than about 15%, e.g., by less than 15%, less than 10%, less than 5%, or less than 1%.

In some embodiments, a subject ALDH agonist increases enzymatic activity of both ALDH2 and ALDH1. In some embodiments, a subject ALDH agonist increases enzymatic activity of both ALDH2 and ALDH1, but does not substantially increase enzymatic activity of an ALDH isozyme other than ALDH2 and ALDH1. In some embodiments, a subject ALDH agonist increases enzymatic activity of both ALDH1 and ALDH2, where the ALDH2 comprises a lysine at amino acid 487 of the mature protein (amino acid 504 of the protein including the leader peptide) as depicted in FIG. 5B.

A subject ALDH agonist will in some embodiments increase an enzymatic activity of an ALDH for a particular substrate or class of substrates. For example, in some embodiments, a subject ALDH agonist increases an enzymatic activity of an ALDH3 enzyme for complex polyaromatic aldehydes such as phenanthrenealdehyde. As another example, a subject ALDH agonist increases an enzymatic activity of an ALDH1 enzyme for a substrate such as phenylacetaldehyde or retinaldehyde. As another example, a subject ALDH agonist increases an enzymatic activity of an ALDH1 enzyme for a naphthaldehyde derivative of the phenanthrene series. As another example, a subject ALDH agonist increases an enzymatic activity of an ALDH3 enzyme for a long-chain aliphatic aldehyde, e.g., octylaldehyde, decylaldehyde, and the like. As another example, a subject ALDH agonist increases an enzymatic activity of an ALDH enzyme for an aromatic aldehyde, e.g., 6-methyoxy-2-naphthaldehyde, 2-naphthaldehyde, 6-dimethylamino-2-naphthaldehyde, etc. As another example, a subject ALDH agonist increases an enzymatic activity of an ALDH2 enzyme for acetaldehyde.

In some embodiments, a compound that modulates ALDH activity modulates a dehydrogenase activity of ALDH, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid. In other embodiments, a compound that modulates ALDH activity modulates an esterase activity of ALDH. In other embodiments, a compound that modulates ALDH activity modulates a reductase activity of ALDH. For example, ALDH can convert nitroglycerin to nitric oxide (NO) via its reductase activity.

As noted above, in some embodiments, a compound that modulates ALDH activity modulates a dehydrogenase activity of ALDH, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid.

A variety of compounds can give rise to aldehyde substrates for ALDH2. Non-limiting examples of compounds that can give rise to aldehyde substrates for ALDH2 include ethanol; a variety of insecticides; industrial toxins such as vinyl chlorides (e.g., polyvinyl chloride); and pyruvate. For example, a compound is ingested, absorbed (e.g., through the skin), or inhaled, by a mammal and is subsequently converted in the mammal into an aldehyde substrate for ALDH2.

Biogenic aldehydes include aldehydes that are produced by a mammal, e.g., are produced metabolically by a mammal. Non-limiting examples of biogenic aldehydes include malondialdehyde (MDA); 3,4-dihydroxyphenylacetaldehyde (DOPAL); 3,4-dihydroxyphenylglycolaldehye (DOPEGAL); hexanal; acrolein; glyoxal; crotonaldehyde; trans-2-nonenal; 4-oxo-2-nonenal; 4-hydroxy-2-nonenal (HNE) (see e.g., Ellis, Pharmacology & Therapeutics (2007) 115:13, Picklo and Montine (2007) J Alzheimers Dis. 12:185); 3-aminopropanal (3-AP), a product of polyamine oxidase; aldehyde products of tyrosine, serine and threonine (see Wood et al, Brain Res (2006)1095; 190); and retinaldehdye (see e.g. Chen et al, Molecular Pharmacology (1994) 46:88).

Xenogenic aldehydes include aldehydes ingested, absorbed, or inhaled by a mammal from source outside the mammal. Xenogenic aldehydes include, e.g., formaldehyde and glutaraldehyde (e.g., McGregor et al., Crit. Rev Toxicol (2006) 36:821 and Pandey et al Hum Exp. Toxicol. (2000) 19:360); chloroacetaldehyde (see e.g., Richardson et al., Mutat. Research (2007) 636:178); reactive aldehydes present in cigarette smoke (see Simth et al., Inhal. Toxicol. (2006) 18:667); and reactive aldehydes present in food sources (see, e.g., Feron et al. (1991) *Mut. Res.* 259:363; Wang et al. (2008) *J. Mol. Cell. Cardiol.* 44:1016).

Non-limiting examples of compounds that are substrates for mitochondrial ALDH2 and cytosolic ALDH1 include 3,4-dihydroxyphenylacetaldehyde (DOPAL); 3,4-dihydroxyphenylglycolaldehye (DOPEGAL); acrolein; formaldehyde; acetaldehyde; propionaldehyde; n-butyraldehyde; capronaldehyde; heptaldehyde; pentaldehyde; octylaldehyde; decylaldehyde; retinaldehyde; 3-hydroxybenzaldehyde; 2,5-dihydroxybenzaldehyde; phenylacetaldehyde; 3-phenylpropionaldehyde (see, e.g., Want et al. (2002) *Drug Metabolism and Disposition* 30:69); cinnamoyl and hydrocinnamoyl aldehydes and their derivative aldehydes (e.g. p-nitrocinnamaldehyde, p-(dimethylamino)cinnamaldehyde, hydrocinnamaldehyde, α-phenylpropionaldehyde); benzaldehyde and its derivative aldehydes (e.g. 2,4-dinitrobenzaldehyde, o-nitro-benzaldehyde, p-nitro-benzaldehyde, p-methyl-benzaldehyde, m-methyl-benzaldehyde, p-methoxy-benzaldehyde, p-(dimethylamino)-benzaldehyde, m-methoxy-benzaldehyde, m-hydroxy-benzaldehyde, 3,4-dimethoxy-benzaldehyde, o-methoxy-benzaldehyde); naphthaldehyde and its derivative aldehydes (e.g. 5-bromo-1-naphthaldehyde, 5-nitro-1-naphthaldehyde, 6[O—$(CH_2)_5$—COOH]-2-naphthaldehyde, 6-(dimethylamino)-2-naphthaldehyde); coumarin-4-carboxaldehyde and its derivative aldehydes (e.g. 7-acetoxy-coumarin-4-carboxaldehyde, 7-(dimethylamino)-coumarin-4-carboxaldehyde, 7-methoxy-coumarin-4-carboxaldehyde, 6,7-dimethoxy-coumarin-4-carboxaldehyde); quinoline, quinolinonecarboxaldehyde, and their derivative aldehydes (e.g. quinoline-3-carboxaldehyde, 7-(dimethylamino)-2-quinolinone-4-carboxaldehyde, quinoline-4-carboxaldehyde, 6-methoxy-2-quinolinone-4-carboxaldehyde); phenanthrene-9-carboxaldehyde; indole-3-aldehyde, indole-3-actaldehyde; 5-methoxyindole-3-carboxaldehyde; 3-pyridinecarboxaldehyde; fluorene-2-carboxaldehyde (see, e.g., Klyosov, (1996) *Biochemstry* 35:4457); 4-hydroxynonenal; malondialdehyde; 3,4-dihydroxyphenylacetaldehyde; and 5-hydroxylindole-3-acetaldehyde. See, also, e.g., Williams et al. (2005) *Anal. Chem.* 77:3383; Marchitti et al. (2007) *Pharmacol. Rev.* 59:125; and Hoffman and Maser (2007) *Drug Metab. Rev.* 39:87.

ALDH Activators

The present disclosure provides ALDH agonists (also referred to as "activators"); and pharmaceutical compositions comprising ALDH agonists. A subject ALDH agonist is useful for treating a variety of disorders, including, e.g., conditions involving ischemic stress, chronic free-radical associated diseases, acute free-radical associated diseases, insensitivity to nitroglycerin (e.g., in angina and heart failure), hypertension, diabetes, seizures, cancer, acute myocardial infarction, stroke, skin damage, dermatitis, atherosclerosis, Alzheimer's Disease, Parkinson's Disease, cataract, skin aging, and other skin disorder (see, e.g. Dreno et al. (2007) *Dermatology* 214:260), acne (see, e.g., Boisnic et al. (2005) *Int J Tissue React.* 27: 91), abnormal hair loss (see, e.g., Everts et. al. (2004) *J Invest Dermatol* 123:258-263; and Everts et al. (2007) *Journal of Investigative Dermatology* 127:1593-1604), and osteoporosis. A subject ALDH agonist is also useful in the detoxification of alcohol, methanol poisoning, ethylene glycol monomethyl ether poisoning, and poisoning due to other xenogenic or biogenic aldehyde compounds. A subject ALDH agonist is also useful in the treatment of alcohol abuse. A subject ALDH agonist is also useful in modulation of embryogenesis and stem cell regeneration, differentiation and development (see, e.g. Mic and Duester (2003) *Developmental Biology* 264: 191-201, Douville et al. (2008) *Stem Cells Dev.* June 23 (e-publication ahead of print; PMID 18573038).

A subject ALDH agonist increases an enzymatic activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH polypeptide in the absence of the agonist.

In some embodiments, a subject ALDH agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH polypeptide in the absence of the agonist.

In some embodiments, a subject ALDH agonist increases the esterase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH polypeptide in the absence of the agonist.

In some embodiments, a subject ALDH agonist increases the reductase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH polypeptide in the absence of the agonist.

In some embodiments, a subject ALDH agonist increases an enzymatic activity of an ALDH2 polypeptide comprising an amino acid sequence set forth in SEQ ID NO:1 (depicted in FIG. 5A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the agonist.

In some embodiments, a subject ALDH agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH2 polypeptide comprising an amino acid sequence set forth in SEQ ID NO:1 (depicted in FIG. 5A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH2 polypeptide in the absence of the agonist.

In some embodiments, a subject ALDH agonist increases an esterase activity of an ALDH2 polypeptide comprising an amino acid sequence set forth in SEQ ID NO:1 (depicted in FIG. 5A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH2 polypeptide in the absence of the agonist.

In some embodiments, a subject ALDH agonist increases a reductase activity of an ALDH2 polypeptide comprising an amino acid sequence set forth in SEQ ID NO:1 (depicted in FIG. 5A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH2 polypeptide in the absence of the agonist.

In some embodiments, a subject ALDH agonist increases an enzymatic activity of an ALDH2 polypeptide comprising an amino acid sequence set forth in SEQ ID NO:2 (depicted in FIG. 5B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the agonist.

In some embodiments, a subject ALDH agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH2 polypeptide comprising an amino acid sequence set forth in SEQ ID NO:2 (depicted in FIG. 5B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH2 polypeptide in the absence of the agonist.

In some embodiments, a subject ALDH agonist increases an esterase activity of an ALDH2 polypeptide comprising an amino acid sequence set forth in SEQ ID NO:2 (depicted in FIG. 5B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH2 polypeptide in the absence of the agonist.

In some embodiments, a subject ALDH agonist increases a reductase activity of an ALDH2 polypeptide comprising an amino acid sequence set forth in SEQ ID NO:2 (depicted in FIG. 5B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH2 polypeptide in the absence of the agonist.

In some embodiments, a subject ALDH agonist increases an enzymatic activity (e.g., an aldehyde dehydrogenase activity, a reductase activity, or an esterase activity) of an ALDH1 polypeptide comprising an amino acid sequence set forth in SEQ ID NO:3 or 4 (depicted in FIGS. 6A and 6B, respectively), by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH1 polypeptide in the absence of the agonist.

In some embodiments, a subject ALDH agonist increases an enzymatic activity (e.g., an aldehyde dehydrogenase activity, a reductase activity, or an esterase activity) of an ALDH3 polypeptide comprising an amino acid sequence set forth in SEQ ID NO:5 (depicted in FIG. 7), by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH3 polypeptide in the absence of the agonist.

In some embodiments, a subject ALDH agonist increases an enzymatic activity (e.g., an aldehyde dehydrogenase activity, a reductase activity, or an esterase activity) of an ALDH5 polypeptide comprising an amino acid sequence set forth in FIG. 12 (SEQ ID NO:6), by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH5 polypeptide in the absence of the agonist.

In some embodiments, a subject ALDH agonist is specific for (e.g., selective for) ALDH2, e.g., a subject ALDH2 agonist increases an enzymatic activity of an ALDH2 enzyme, but does not substantially increase the same enzymatic activity of cytosolic aldehyde dehydrogenase-1 (ALDH1), e.g., a subject ALDH2 agonist increases an enzymatic activity of an ALDH1 enzyme, if at all, by less than about 15%, less than about 10%, less than about 5%, less than about 2%, or less than about 1%, when used at a concentration that increases the same enzymatic activity of an ALDH2 enzyme by at least about 5% or more. In some embodiments, a subject ALDH2 agonist does not substantially increase the enzymatic activity of alcohol dehydrogenase (ADH), e.g., a subject ALDH2 agonist increases the enzymatic activity of an ADH, if at all, by less than about 5%, less than about 2%, or less than about 1%, when used at a concentration that increases the enzymatic activity of an ALDH2 enzyme by at least about 5% or more.

For example, in some embodiments, a subject ALDH agonist is specific for (e.g., selective for) ALDH2, e.g., a subject ALDH2 agonist increases dehydrogenase activity of an ALDH2 enzyme, but does not substantially increase the dehydrogenase activity of cytosolic aldehyde dehydrogenase-1 (ALDH1), e.g., a subject ALDH2 agonist increases dehydrogenase activity of an ALDH1 enzyme, if at all, by less than about 15%, less than about 10%, less than about 5%, less than about 2%, or less than about 1%, when used at a concentration that increases dehydrogenase activity of an ALDH2 enzyme by at least about 5% or more. In some embodiments, a subject ALDH2 agonist does not substantially increase dehydrogenase activity of alcohol dehydrogenase (ADH), e.g., a subject ALDH2 agonist increases the dehydrogenase activity of an ADH, if at all, by less than about 5%, less than about 2%, or less than about 1%, when used at a concentration that increases the dehydrogenase activity of an ALDH2 enzyme by at least about 5% or more.

In some embodiments, a subject ALDH agonist is specific for (e.g., selective for) ALDH1, e.g., a subject ALDH agonist increases an enzymatic activity of an ALDH1 enzyme, but does not substantially increase the same enzymatic activity of any other ALDH isozyme, e.g., a subject ALDH agonist increases an enzymatic activity of an ALDH isozyme other than ALDH1, if at all, by less than about 15%, less than about 10%, less than about 5%, less than about 2%, or less than about 1%, when used at a concentration that increases the same enzymatic activity of an ALDH1 enzyme by at least about 15% or more.

In some embodiments, a subject ALDH agonist is specific for (e.g., selective for) ALDH3, e.g., a subject ALDH agonist increases an enzymatic activity of an ALDH3 enzyme, but does not substantially increase the same enzymatic activity of any other ALDH isozyme, e.g., a subject ALDH agonist increases an enzymatic activity of an ALDH isozyme other than ALDH3, if at all, by less than about 15%, less than about 10%, less than about 5%, less than about 2%, or less than about 1%, when used at a concentration that increases the same enzymatic activity of an ALDH3 enzyme by at least about 15% or more.

In some embodiments, a subject ALDH agonist is specific for (e.g., selective for) ALDH5, e.g., a subject ALDH agonist increases an enzymatic activity of an ALDH5 enzyme, but does not substantially increase the same enzymatic activity of any other ALDH isozyme, e.g., a subject ALDH agonist increases an enzymatic activity of an ALDH isozyme other than ALDH5, if at all, by less than about 15%, less than about 10%, less than about 5%, less than about 2%, or less than about 1%, when used at a concentration that increases the same enzymatic activity of an ALDH5 enzyme by at least about 15% or more.

In some embodiments, a subject ALDH agonist increases an enzymatic activity of both ALDH1 and ALDH2, but does not does not substantially increase the same enzymatic activity of any other ALDH isozyme, e.g., a subject ALDH agonist increases an enzymatic activity of an ALDH isozyme other than ALDH1 and ALDH2, if at all, by less than about 15%, less than about 10%, less than about 5%, less than about 2%, or less than about 1%, when used at a concentration that increases the same enzymatic activity of an ALDH1 and ALDH2 enzyme by at least about 15% or more.

In some embodiments, a subject ALDH agonist has an $EC_{50}$ (half maximal effective concentration) of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

For example, in some embodiments, a subject ALDH agonist has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM, for a dehydrogenase activity of mitochondrial ALDH2.

In some embodiments, a subject ALDH2 agonist has an $EC_{50}$ for an ALDH2 polypeptide comprising an amino acid sequence set forth in SEQ ID NO:1 (depicted in FIG. 5A), or as set forth in amino acids 18-517 of SEQ ID NO:1, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

For example, in some embodiments, a subject ALDH2 agonist has an $EC_{50}$ for dehydrogenase activity of an ALDH2 polypeptide comprising an amino acid sequence set forth in SEQ ID NO:1 (depicted in FIG. 5A), or as set forth in amino acids 18-517 of SEQ ID NO:1, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

In some embodiments, a subject ALDH2 agonist has an $EC_{50}$ for an ALDH2 polypeptide comprising an amino acid sequence set forth in SEQ ID NO:2 (depicted in FIG. 5B), or as set forth in amino acids 18-517 of SEQ ID NO:2, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

In some embodiments, a subject ALDH2 agonist has an $EC_{50}$ for dehydrogenase activity of an ALDH2 polypeptide comprising an amino acid sequence set forth in SEQ ID NO:2 (depicted in FIG. 5B), or as set forth in amino acids 18-517 of SEQ ID NO:2, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

In some embodiments, a subject ALDH agonist has an $EC_{50}$ for an enzymatic activity (e.g., an aldehyde dehydrogenase activity, an esterase activity, a reductase activity) of an ALDH1 polypeptide of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

In some embodiments, a subject ALDH agonist has an $EC_{50}$ for an enzymatic activity (e.g., an aldehyde dehydrogenase activity, an esterase activity, a reductase activity) of an ALDH3 polypeptide of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 μM, from about 1 μM to about 10 μM, from about 10 μM to about 25 μM, from about 25 μM to about 50 μM, from about 50 μM to about 75 μM, from about 75 μM to about 100 μM, from about 100 μM to about 250 μM, from about 250 μM to about 500 μM, or from about 500 μM to about 1 mM.

In some embodiments, a subject ALDH agonist has an $EC_{50}$ for an enzymatic activity (e.g., an aldehyde dehydrogenase activity, an esterase activity, a reductase activity) of an ALDH5 polypeptide of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH agonist is a compound of generic Formula I, as shown below:

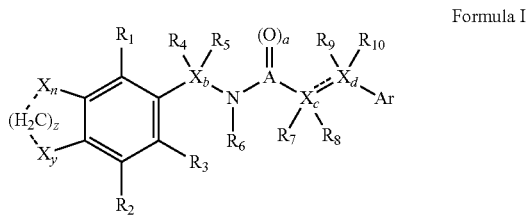

Formula I where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond; where z is the integer 0, 1, or 2;

where ⩵ is an optional double bond;

where each of $R_1$, $R_2$, $R_3$, $R_4$, $R_5$, $R_6$, $R_7$, $R_8$, $R_9$, and $R_{10}$ is independently selected from H; C; N; O; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where A is C or S; and where a=1 when A=C; and where a=2 when A=S;

where $X_b$ is C, N, O, or S; where b is the integer 0 or 1;
where $X_c$ is C, N, O, or S; where c is the integer 0 or 1;
where $X_d$ is C, N, O, or S; where d is the integer 0 or 1; and
where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

For example, in some embodiments, Ar of Formula I is:

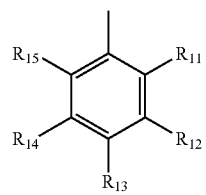

where $R_{11}$-$R_{15}$ are each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group. In some embodiments, Ar of Formula I is a substituted naphthalene group, e.g., a methoxy-substituted naphthalene group.

In other embodiments, Ar of Formula I is a substituted or unsubstituted heterocyclic group, e.g., a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group. In some embodiments, Ar of Formula I is a substituted thiophene group, e.g., a 2-carboxylic acid amide-substituted thiophene group.

In other embodiments, Ar of Formula I is a substituted or unsubstituted heterocyclic group, e.g., a substituted or unsubstituted pyridine, a thiazole, an imidazole, a thiophene, a quinoline, an isoquinoline, or a furan group. In some embodiments, Ar of formula I is a substituted pyridine-oxide.

In some embodiments, a subject ALDH agonist has the structure of Compound Alda-52, as shown below:

Compound Alda-52

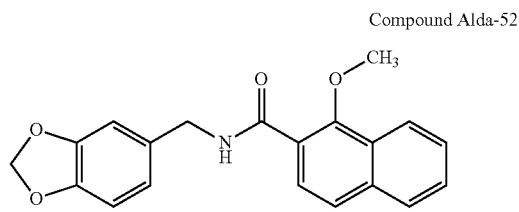 [SMILES: COc1c(C(=O)NCc2ccc3c(c2)OCO3)ccc2ccccc12]

Compound Alda-52: 1-methoxy-naphthalene-2-carboxylic acid (benzo[1,3]dioxol-5-ylmethyl)-amide.

In some embodiments, a subject ALDH agonist has the structure of Compound Alda-59, as shown below:

Compound Alda-59

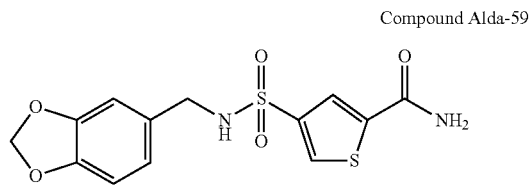 [SMILES: NC(=O)c1cc(S(=O)(=O)NCc2ccc3c(c2)OCO3)cs1]

Compound Alda-59: 4-[(benzo[1,3]dioxol-5-ylmethyl)-sulfamoyl]-thiophene-2-carboxylic acid amide.

In some embodiments, a subject ALDH agonist has the structure of Compound Alda-72, as shown below:

Compound Alda-72

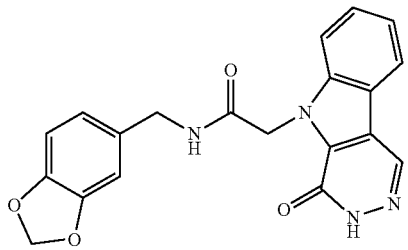

Compound Alda-72: N-benzo[1,3]dioxol-5-ylmethyl-2-(1-oxo-1,2-dihydro-2,3,9-triaza-fluoren-9-yl)-acetamide.

In some embodiments, a subject ALDH agonist has the structure of Compound Alda-71, as shown below:

Compound Alda-71

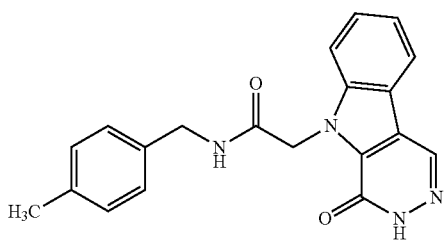

Compound Alda-71: N-(4-methyl-benzyl)-2-(1-oxo-1,2-dihydro-2,3,9-triaza-fluoren-9-yl)-acetamide.

In some embodiments, a subject ALDH agonist has the structure of Compound Alda-53, as shown below:

Compound Alda-53

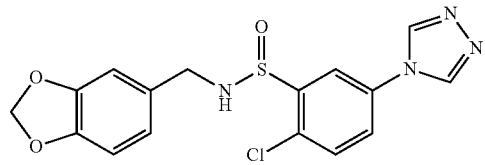

Compound Alda-53: N-benzo[1,3]dioxol-5-ylmethyl-2-chloro-5-[1,2,4]triazol-4-yl-benzamide.

In some embodiments, a subject ALDH agonist has the structure of Compound Alda-54, as shown below:

Compound Alda-54

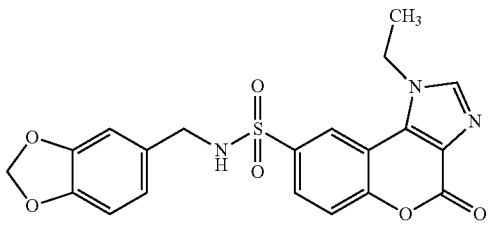

Compound Alda-54: 1-ethyl-4-oxo-1,4-dihydro-chromeno[3,4-d]imidazole-8-sulfonic acid (benzo[1,3]dioxol-5-ylmethyl)-amide.

In some embodiments, a subject ALDH agonist has the structure of Compound Alda-61, as shown below:

Compound Alda-61

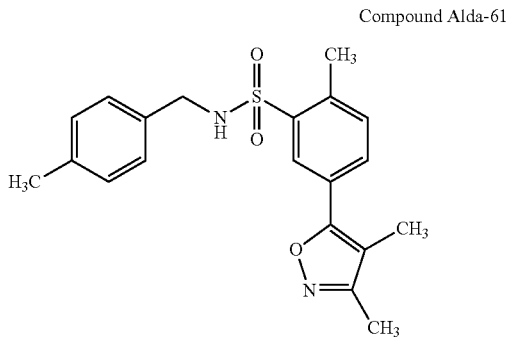

Compound Alda-61: 5-(3,4-dimethyl-isoxazol-5-yl)-2-methyl-N-(4-methyl-benzyl)-benzene sulfonamide.

In some embodiments, a subject ALDH agonist has the structure of Compound Alda-60, as shown below:

Compound Alda-60

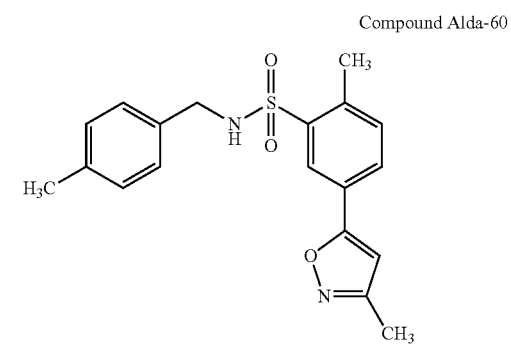

Compound Alda-60: 2-methyl-N-(4-methyl-benzyl)-5-(3-methyl-isoxazol-5-yl)-benzene sulfonamide.

In some embodiments, a subject ALDH agonist has the structure of Compound Alda-66, as shown below:

Compound Alda-66

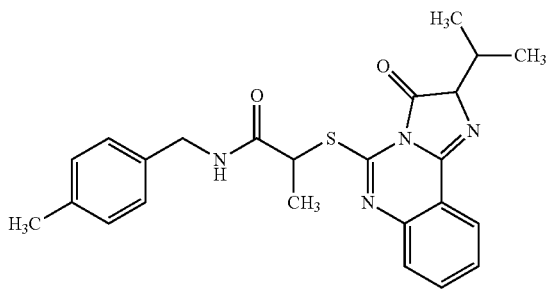

Compound Alda-66: 2-(2-isopropyl-3-oxo-2,3-dihydro-imidazo[1,2-c]quinazolin-5-ylsulfanyl)-N-(4-methyl-benzyl)-propionamide.

In some embodiments, a subject ALDH agonist has the structure of Compound Alda-65, as shown below:

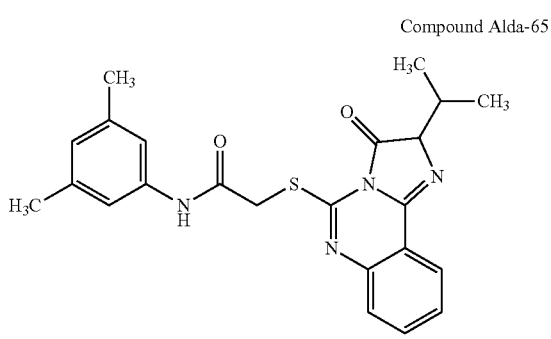 [SMILES: Cc1cc(C)cc(NC(=O)CSC2=Nc3ccccc3C3=NC(C(C)C)C(=O)N23)c1]

Compound Alda-65: N-(3,5-dimethyl-phenyl)-2-(2-isopropyl-3-oxo-2,3-dihydro-imidazo[1,2-c]quinazolin-5-yl-sulfanyl)-acetamide.

In some embodiments, a subject ALDH agonist has the structure of Compound Alda-64, as shown below:

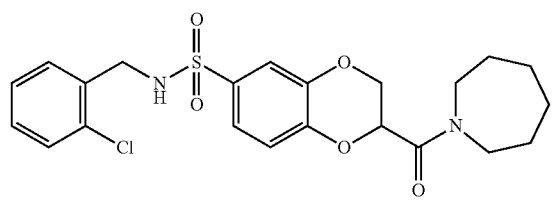

Compound Alda-64: 2-(azepane-1-carbonyl)-N-(2-chloro-benzyl)-2,3-dihydro-benzo[1,4]dioxine-6-sulfonamide.

In some embodiments, a subject ALDH agonist has the structure of Compound Alda-84, as shown below:

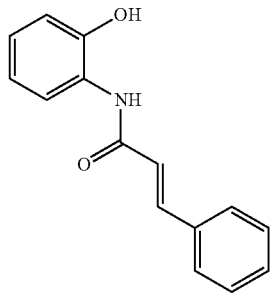

Compound Alda-84: N-(2-hydroxy-phenyl)-3-phenyl-acrylamide.

In some embodiments, a subject ALDH agonist is a compound of generic Formula Ia, as shown below:

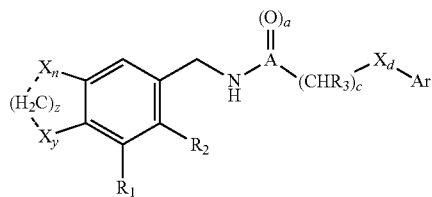

where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where A=C or S, and where a=1 when A=C; and where a=2 when A=S;

where $R_1$, $R_2$, and $R_3$ are each independently selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where c is the integer 0 or 1;

where $X_d$ is C, N, O, or S; where d is the integer 0 or 1; and where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, the following compounds are exemplary, non-limiting compounds of Formula Ia: Alda-52, Alda-59, Alda-72, Alda-71, Alda-53, Alda-54, Alda-61, Alda-60, Alda-66 and Alda-64.

In some embodiments, a subject ALDH agonist is a compound of sub-generic Formula Ib, as shown below:

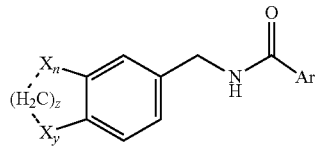

where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, the following compounds are exemplary, non-limiting compounds of Formula Ib: Alda-52 and Alda-53.

In some embodiments, a subject ALDH agonist is a compound of sub-generic Formula Ic, as shown below:

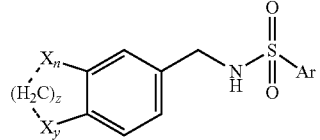

where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, the following compounds are exemplary, non-limiting compounds of Formula Ic: Alda-59, Alda-60, Alda-61 and Alda-64.

In some embodiments, a subject ALDH agonist is a compound of sub-generic Formula Id, as shown below:

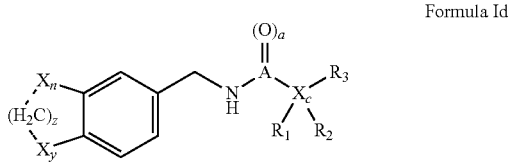

Formula Id where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where A=C or S, and where a=1 when A=C; and where a=2 when A=S;

where $X_c$ is C, N, O, or S; where c is the integer 0 or 1; and where $R_1$ and $R_2$ are each independently selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_3$ is selected from a substituted polycyclic group, an unsubstituted polycyclic group, a substituted hetero polycyclic group, and an unsubstituted hetero polycyclic group;

or a pro-drug, a pharmaceutically acceptable salt, an analog, or a derivative thereof.

In some embodiments, the following compounds are exemplary, non-limiting compounds of Formula Id: Alda-71, Alda-72 and Alda-54.

In some embodiments, a subject ALDH agonist is a compound of sub-generic Formula Ie, as shown below:

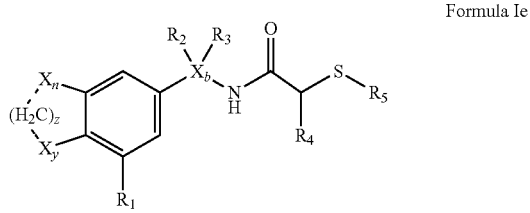

Formula Ie where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where $X_b$ is C, N, O, or S; where c is the integer 0 or 1; and where $R_1$, $R_2$, $R_3$ and $R_4$ are each independently selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_5$ is selected from a substituted polycyclic group, an unsubstituted polycyclic group, a substituted hetero polycyclic group, and an unsubstituted hetero polycyclic group;

or a pro-drug, a pharmaceutically acceptable salt, an analog, or a derivative thereof.

In some embodiments, the following compounds are exemplary, non-limiting compounds of Formula Ie: Alda-65 and Alda-66.

In some embodiments, a subject ALDH agonist is a compound of generic Formula If, as shown below:

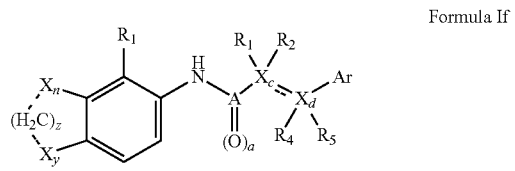

Formula If where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where ⋯ is an optional double bond;

where A=C or S, and where a=1 when A=C; and where a=2 when A=S;

where $R_1$, $R_2$, $R_3$, $R_4$ and $R_5$ are each independently selected from H; —OH; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $X_c$ is C, N, O, or S; where c is the integer 0 or 1;

where $X_d$ is C, N, O, or S; where c is the integer 0 or 1; and where Ar is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

An exemplary, non-limiting compound of Formula If is Alda-84.

In some embodiments, a subject ALDH agonist is a compound of generic Formula II, as shown below:

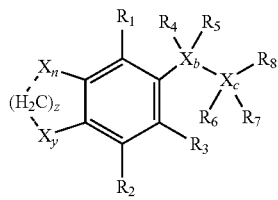

Formula II where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond; where z is the integer 0, 1, or 2;

where $R_1$ to $R_7$ is each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where $X_b$ is C, N, O, or S; where b is the integer 0 or 1;

where $X_c$ is C, N, O, or S; where c is the integer 0 or 1; and where $R_8$ is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, $R_8$ of Formula II is a substituted or unsubstituted heterocyclic group, e.g., a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group. In some embodiments, $R_8$ of Formula II is a substituted pyrrolidin-2-one group, a substituted pyrrolo[2,3-d]pyrimidine group, a substituted pyrazolo[3,4-d]pyrimidine group, a substituted pyrazin-2-one group, or a substituted 4,5,6,7-tetrahydro-tetrazolo[1,5-a]pyrimidine group.

In other embodiments, $R_8$ of Formula II is a substituted or unsubstituted heterocyclic group, e.g., a substituted or unsubstituted pyridine, a thiazole, an imidazole, a thiophene, a quinoline, an isoquinoline, or a furan group. In some embodiments, $R_8$ of Formula II is a substituted pyridine-oxide.

In some embodiments, a subject ALDH agonist has the structure of Compound Alda-58, as shown below:

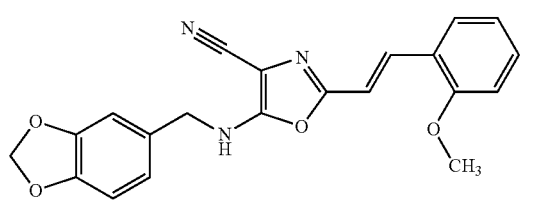

Compound Alda-58

Compound Alda-58: 5-[(benzo[1,3]dioxol-5-ylmethyl)-amino]-2-[2-(2-methoxy-phenyl)-vinyl]-oxazole-4-carbonitrile.

In some embodiments, a subject ALDH agonist has the structure of Compound Alda-70, as shown below:

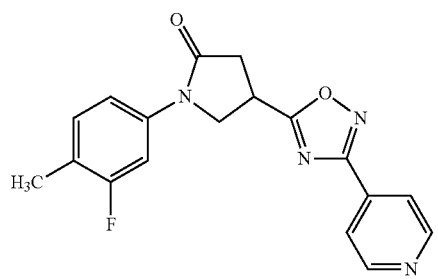

Compound Alda-70

Compound Alda-70: 1-(3-fluoro-4-methyl-phenyl)-4-(3-pyridin-4-yl-[1,2,4]oxadiazol-5-yl)-pyrrolidin-2-one.

In some embodiments, a subject ALDH agonist has the structure of Compound Alda-69, as shown below:

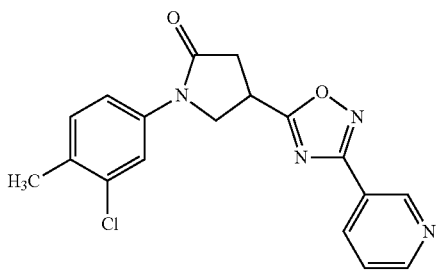

Compound Alda-69

Compound Alda-69: 1-(3-chloro-4-methyl-phenyl)-4-(3-pyridin-3-yl-[1,2,4]oxadiazol-5-yl)-pyrrolidin-2-one.

In some embodiments, a subject ALDH agonist has the structure of Compound Alda-73, as shown below:

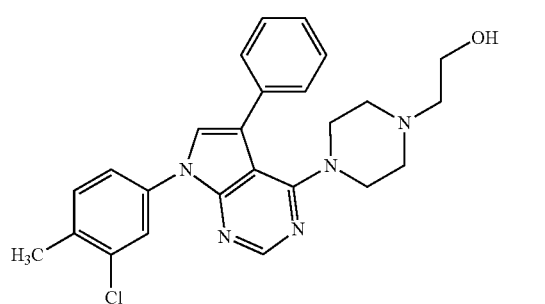

Compound Alda-73

Compound Alda-73: 2-{4-[7-(3-chloro-4-methyl-phenyl)-5-phenyl-7H-pyrrolo[2,3-d]pyrimidin-4-yl]-piperazin-1-yl}-ethanol.

In some embodiments, a subject ALDH agonist has the structure of Compound Alda-67, as shown below:

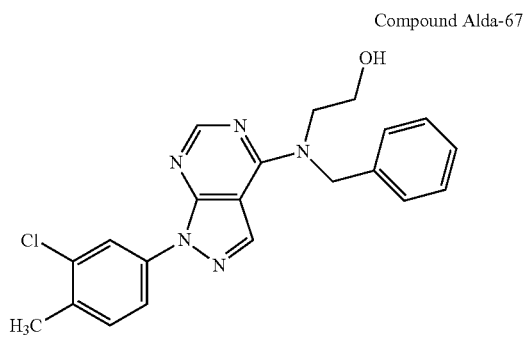 [SMILES: Cc1ccc(-n2ncc3c(N(CCO)Cc4ccccc4)ncnc32)cc1Cl]

Compound Alda-67

Compound Alda-67: 2-{benzyl-[1-(3-chloro-4-methyl-phenyl)-1H-pyrazolo[3,4-d]pyrimidin-4-yl]-amino}-ethanol.

In some embodiments, a subject ALDH agonist has the structure of Compound Alda-68, as shown below:

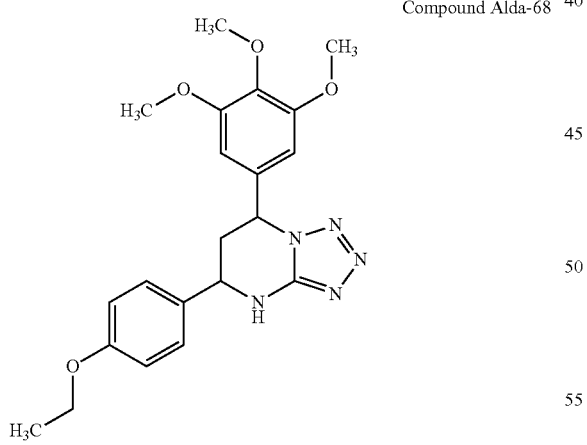

Compound Alda-68

Compound Alda-68: 5-(4-ethoxy-phenyl)-7-(3,4,5-trimethoxy-phenyl)-4,5,6,7-tetrahydro-tetrazolo[1,5-a]pyrimidine.

In some embodiments, a subject ALDH agonist has the structure of Compound Alda-56, as shown below:

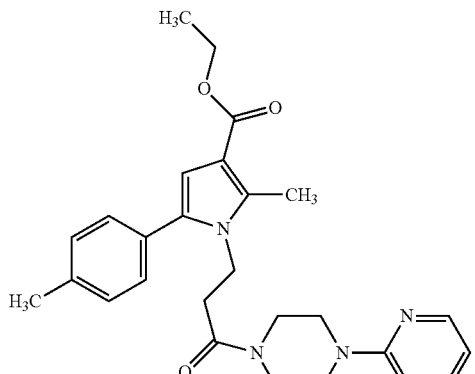

Compound Alda-56

Compound Alda-56: 2-methyl-1-[3-oxo-3-(4-pyridin-2-yl-piperazin-1-yl)-propyl]-5-p-tolyl-1H-pyrrole-3-carboxylic acid ethyl ester.

In some embodiments, a subject ALDH agonist has the structure of Compound Alda-57, as shown below:

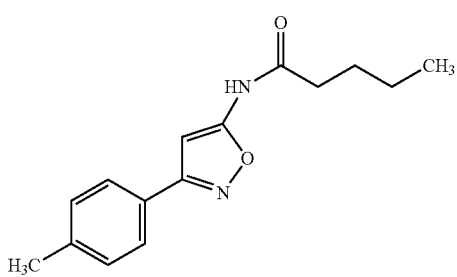

Compound Alda-57

Compound Alda-57: pentanoic acid (3-p-tolyl-isoxazol-5-yl)-amide.

In some embodiments, a subject ALDH agonist has the structure of Compound Alda-63, as shown below:

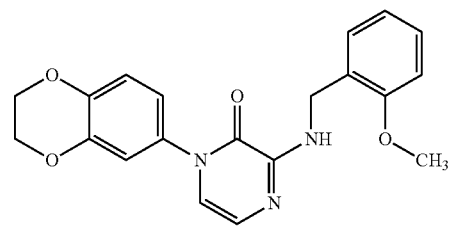

Compound Alda-63

Compound Alda-63: 1-(2,3-dihydro-benzo[1,4]dioxin-6-yl)-3-(2-methoxy-benzylamino)-1H-pyrazin-2-one.

In some embodiments, a subject ALDH agonist has the structure of Compound Alda-62, as shown below:

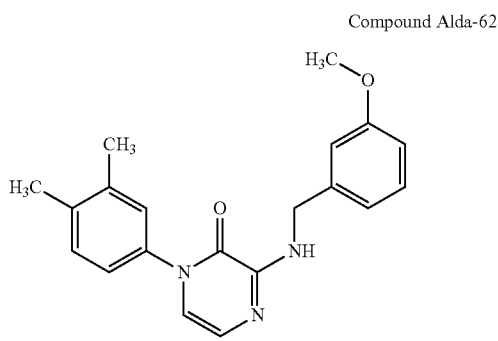 [SMILES: COc1cccc(CNc2nccn(-c3ccc(C)c(C)c3)c2=O)c1]

Compound Alda-62

Compound Alda-62: 1-(3,4-dimethyl-phenyl)-3-(3-methoxy-benzylamino)-1H-pyrazin-2-one.

In some embodiments, a subject ALDH agonist has the structure of Compound Alda-83, as shown below:

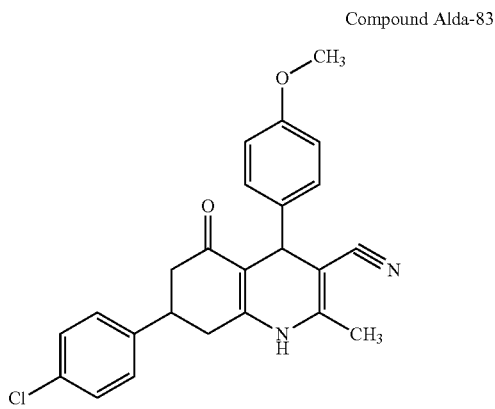 [SMILES: COc1ccc(C2C(C#N)=C(C)NC3=C2C(=O)CC(c2ccc(Cl)cc2)C3)cc1]

Compound Alda-83

Compound Alda-83: 7-(4-chloro-phenyl)-4-(4-methoxyphenyl)-2-methyl-5-oxo-1,4,5,6,7,8-hexahydro-quinoline-3-carbonitrile.

In some embodiments, a subject ALDH agonist has the structure of safrole, as shown below:

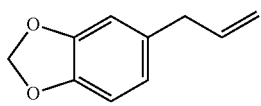

Safrole is 5-(2-propenyl)-1,3-benzodioxole.

In some embodiments, safrole (5-(2-propenyl)-1,3-benzodioxole) is specifically excluded.

In some embodiments, a subject ALDH agonist has the structure of isosafrole, as shown below:

Isosafrole

Isosafrole is 5-propenyl-benzo[1,3]dioxole. In some embodiments, isosafrole is specifically excluded.

In some embodiments, a subject ALDH agonist has the structure of eugenol, as shown below:

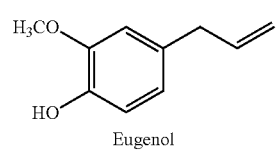

Eugenol

Eugenol is 4-allyl-2-methoxy-phenol. In some embodiments, eugenol is specifically excluded.

In some embodiments, a subject ALDH agonist has the structure of sesamin, as shown below:

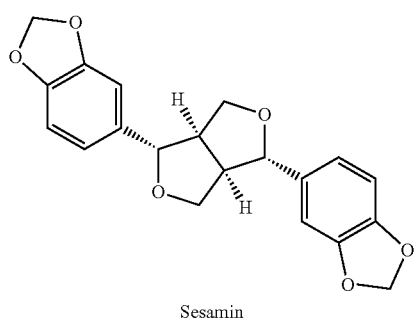 [SMILES: c1cc2c(cc1[C@H]1OC[C@H]3[C@@H]1CO[C@@H]3c1ccc3c(c1)OCO3)OCO2]

Sesamin

Sesamin is 5,5'-(1S,3aR,4S,6aR)-tetrahydro-1H,3H-furo[3,4-c]furan-1,4-diylbis(1,3-benzodioxole). In some embodiments, sesamin is specifically excluded.

In some embodiments, a subject ALDH agonist is a compound of sub-generic Formula IIa, as shown below:

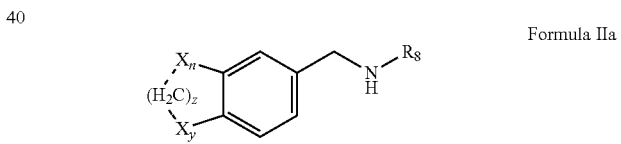

Formula IIa where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where $R_8$ is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, the following compounds are exemplary, non-limiting compounds of Formula IIa: Alda-58.

In some embodiments, a subject ALDH agonist is a compound of sub-generic Formula IIb, as shown below:

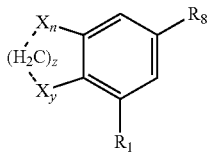

Formula IIb where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where $R_1$ is selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_8$ is selected from a substituted cyclic group, an unsubstituted cyclic group, a substituted heterocyclic group, and an unsubstituted heterocyclic group;

or a pro-drug, a pharmaceutically acceptable salt, an analog, or a derivative thereof.

In some embodiments, the following compounds are exemplary, non-limiting compounds of Formula II): Alda-69, Alda-70, Alda-62 and Alda-63.

In some embodiments, a subject ALDH agonist is a compound of sub-generic Formula IIc, as shown below:

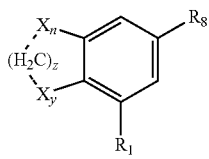

Formula IIc where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where $R_1$ is selected from H; a halo (e.g., bromo, fluoro, chloro, iodo); an aliphatic group, an alkyl group; a substituted alkyl group; a substituted or unsubstituted alkenyl group; and a substituted or unsubstituted alkynyl group;

where $R_8$ is selected from a substituted bicyclic group, an unsubstituted bicyclic group, a substituted hetero bicyclic group, and an unsubstituted hetero bicyclic group;

or a pro-drug, a pharmaceutically acceptable salt, an analog, or a derivative thereof.

In some embodiments, the following compounds are exemplary, non-limiting compounds of Formula IIe: Alda-67, Alda-68, Alda-73, Alda-83, and sesamin.

In some embodiments, a subject ALDH agonist is a compound of sub-generic Formula IId, as shown below:

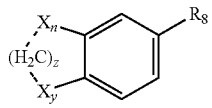

Formula IId where $X_n$ and $X_y$ are each independently H, C, N, O, or a halogen (e.g., F, Br, Cl, or I); where n is the integer 0 or 1; where y is the integer 0 or 1;

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where $R_8$ is selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

In some embodiments, the following compounds are exemplary, non-limiting compounds of Formula IId: Alda-56 and Alda-57.

In some embodiments, a subject ALDH agonist is a compound of generic Formula III, as shown below:

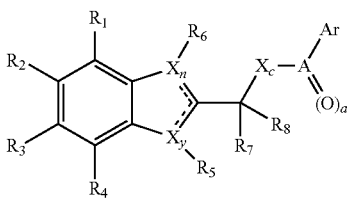

Formula III where $X_n$ and $X_y$ are each independently C, N, O, or S; where n is the integer 0, 1 or 2; where y is the integer 0, 1 or 2;

where ⋯ is an optional double bond;

where each of $R_1$, $R_2$, $R_3$, $R_4$, $R_5$, $R_6$, $R_7$ and $R_8$ is independently selected from H; C; N; O; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where A is C or S; and where a=1 when A=C; and where a=2 when A=S;

where $X_c$ is C, N, O, or S; where c is the integer 0 or 1;

where Ar is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, Ar of Formula III is a substituted or unsubstituted heterocyclic group, e.g., a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group.

In some embodiments, a subject ALDH agonist has the structure of Compound Alda-81, as shown below:

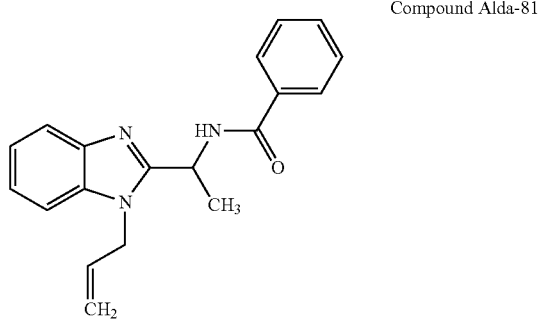 [SMILES: C=CCn1c(C(C)NC(=O)c2ccccc2)nc2ccccc21]

Compound Alda-81

Compound Alda-81: N-[1-(1-allyl-1H-benzoimidazol-2-yl)-ethyl]-benzamide.

In some embodiments, a subject ALDH agonist is a compound of generic Formula IV, as shown below:

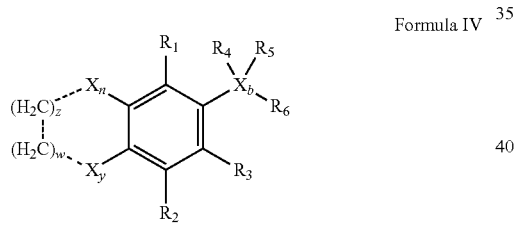

Formula IV where $X_n$ and $X_y$ are each independently C, N, O, or S; where n is the integer 0, 1 or 2; where y is the integer 0, 1 or 2;

where ⋯ (dotted line) is an optional bond;

where z is the integer 0 or 1, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where w is the integer 0 or 1, with the provisos that: 1) w=0 when X=halogen and ⋯ is not a bond; and 2) when w=0, X=O, ⋯ is not a bond, and one or more oxygen atoms (X) are present, oxygen is attached to a methyl group;

where each of $R_1$, $R_2$, $R_3$, $R_4$, and $R_5$ is independently selected from H; C; N; O; a halo (e.g., bromo, fluoro, chloro, iodo); a substituted or unsubstituted alkoxyl group, a substituted or unsubstituted amine group, a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where $X_b$ is C, N, O, or S; where b is the integer 0 or 1;

where $R_6$ is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, $R_6$ of Formula IV is a substituted or unsubstituted alkenyl group, e.g., a substituted or unsubstituted ethenyl group, a substituted or unsubstituted propenyl group, a substituted or unsubstituted allyl group, and the like.

In some embodiments, a subject ALDH agonist has the structure of dillapiol, as shown below:

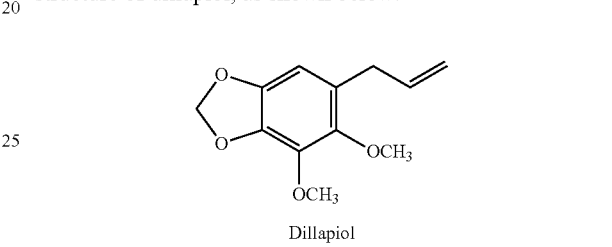

Dillapiol

Dillapiol is 6-allyl-4,5-dimethoxy-benzo[1,3]dioxole. In some embodiments, dillapiol is specifically excluded.

In some embodiments, a subject ALDH agonist has the structure of apiol, as shown below:

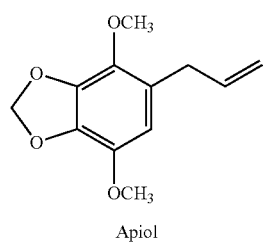 [SMILES: C=CCc1cc(OC)c2c(c1OC)OCO2]

Apiol

Apiol is 5-allyl-4,7-dimethoxy-benzo[1,3]dioxole. In some embodiments, apiol is specifically excluded.

In some embodiments, a subject ALDH agonist has the structure of myristicin, as shown below:

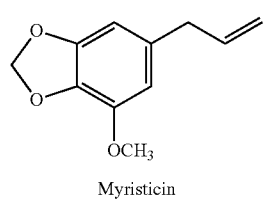

Myristicin

Myristicin is 4-methoxy-6-prop-2-enyl-benzo[1,3]dioxole. In some embodiments, myristicin is specifically excluded.

In some embodiments, a subject ALDH agonist has the structure of elemicin, as shown below:

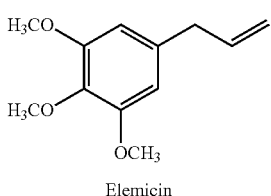

Elemicin

Elemicin is 5-allyl-1,2,3-trimethoxy-benzene. In some embodiments, elemicin is specifically excluded.

In some embodiments, a subject ALDH agonist is a compound of generic Formula V, as shown below:

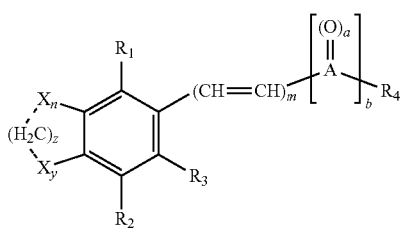

Formula V where $X_n$ and $X_y$ are each independently C, N, O, or S; where n is the integer 0, 1 or 2; where y is the integer 0, 1 or 2;

where ⋯ (dotted line) is an optional bond;

where z is the integer 0 or 1, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where each of $R_1$, $R_2$ and $R_3$ is independently selected from H; C; N; O; a halo (e.g., bromo, fluoro, chloro, iodo); a substituted or unsubstituted alkoxyl group, a substituted or unsubstituted amine group, a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where m is an integer from 1 to 10;

where A is C or S; and where a=1 when A=C; and where a=2 when A=S;

where b is the integer 0 or 1;

where $R_4$ is selected from a hydroxyl group, an amine group, a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

For example, in some embodiments, $R_4$ of Formula V is a substituted or unsubstituted heterocyclic group, e.g., a substituted or unsubstituted piperidine, a substituted or unsubstituted pyran, a substituted or unsubstituted pyranone, a substituted or unsubstituted pyridine, a substituted or unsubstituted pyrazine, a substituted or unsubstituted pyrimidine, a substituted or unsubstituted pyridazine, a substituted or unsubstituted pyrrole, a substituted or unsubstituted furan, a substituted or unsubstituted pyrazole, a substituted or unsubstituted oxazole, a substituted or unsubstituted isoxazole, a substituted or unsubstituted thiazole, a substituted or unsubstituted imidazole, a substituted or unsubstituted thiophene, a substituted or unsubstituted quinoline, or a substituted or unsubstituted isoquinoline group.

In some embodiments, a subject ALDH agonist has the structure of piperine, as shown below:

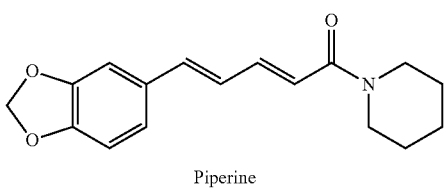 [SMILES: O=C(/C=C/C=C/c1ccc2c(c1)OCO2)N1CCCCC1]

Piperine

Piperine is 1-[5-(1,3-benzodioxol-5-yl)-1-oxo-2,4-pentadienyl]piperidine. In some embodiments, piperine is specifically excluded.

In some embodiments, a subject ALDH agonist has the structure of methysticin, as shown below:

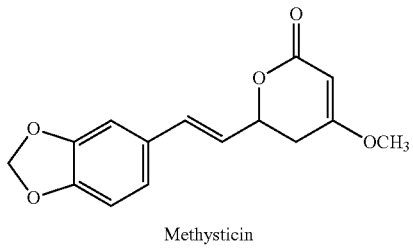 [SMILES: COC1=CC(=O)OC(/C=C/c2ccc3c(c2)OCO3)C1]

Methysticin

Methysticin is 6-(2-Benzo[1,3]dioxol-5-yl-vinyl)-4-methoxy-5,6-dihydro-pyran-2-one. In some embodiments, methysticin is specifically excluded.

In some embodiments, a subject ALDH agonist has the following structure (Alda-101):

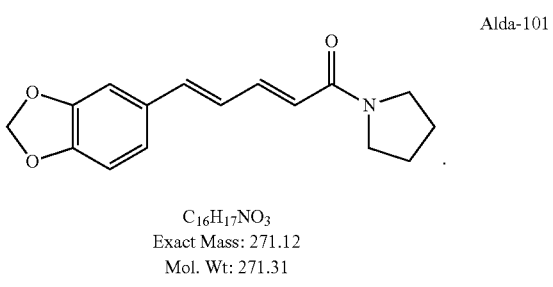 [SMILES: O=C(/C=C/C=C/c1ccc2c(c1)OCO2)N1CCCC1]

Alda-101

$C_{16}H_{17}NO_3$
Exact Mass: 271.12
Mol. Wt: 271.31

In some embodiments, a subject ALDH agonist has the following structure (Alda-102):

Alda-102

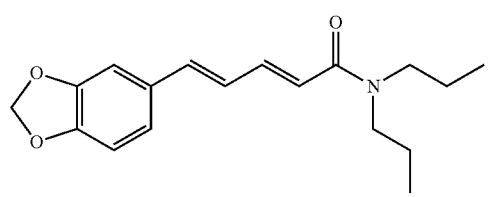

C$_{18}$H$_{23}$NO$_3$
Exact Mass: 301.17
Mol. Wt: 301.38

In some embodiments, a subject ALDH agonist has the following structure (Alda-103):

Alda-103

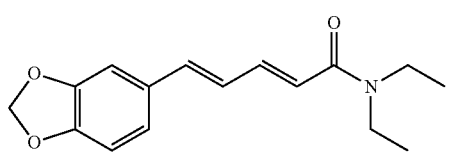

C$_{16}$H$_{19}$NO$_3$
Exact Mass: 273.14
Mol. Wt: 273.33

In some embodiments, a subject ALDH agonist has the following structure (Alda-104a):

Alda-104a

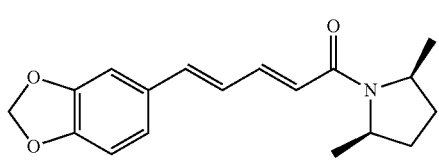

C$_{18}$H$_{21}$NO$_3$
Exact Mass: 299.15
Mol. Wt: 299.36

In some embodiments, a subject ALDH agonist has the following structure (Alda-104b):

Alda-104b

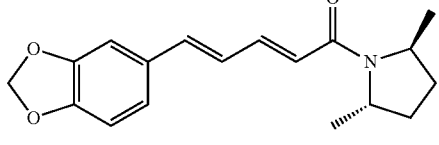

C$_{18}$H$_{21}$NO$_3$
Exact Mass: 299.15
Mol. Wt: 299.36

In some embodiments, a subject ALDH agonist has the following structure (Alda-105):

Alda-105

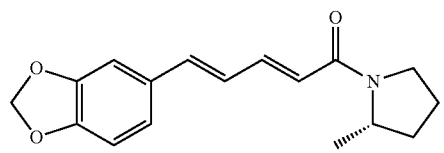

C$_{17}$H$_{19}$NO$_3$
Exact Mass: 285.14
Mol. Wt: 285.34

In some embodiments, a subject ALDH agonist has the following structure (Alda-106):

Alda-106

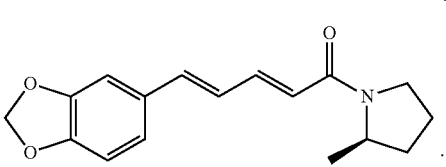

C$_{17}$H$_{19}$NO$_3$
Exact Mass: 285.14
Mol. Wt: 285.34

In some embodiments, a subject ALDH agonist has the following structure (Alda-108):

(Alda-108)

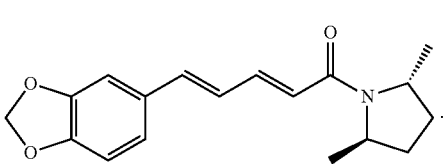

In some embodiments, a subject ALDH agonist has the following structure (Alda-109):

(Alda-109)

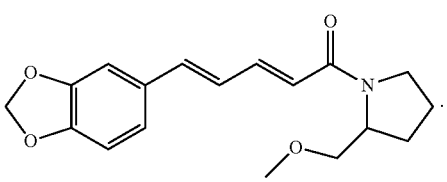

In some embodiments, a subject ALDH agonist has the following structure (Alda-110):

(Alda-110)

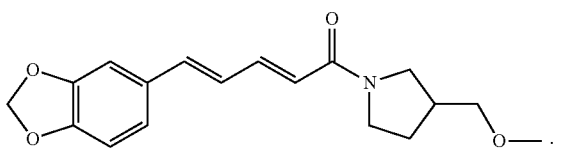

In some embodiments, a subject ALDH agonist has the following structure (Alda-111):

(Alda-111)

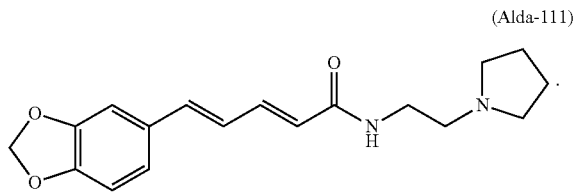 [SMILES: O=C(/C=C/C=C/c1ccc2c(c1)OCO2)NCCN1CCCC1]

In some embodiments, a subject ALDH agonist has the following structure (Alda-112):

(Alda-112)

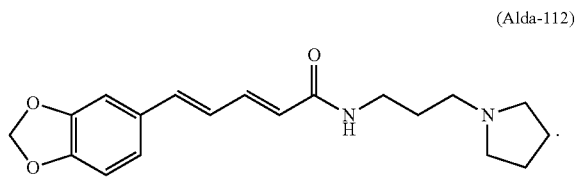 [SMILES: O=C(/C=C/C=C/c1ccc2c(c1)OCO2)NCCCN1CCCC1]

In some embodiments, a subject ALDH agonist has the structure of 5-benzo[1,3]dioxol-5-yl-penta-2,4-dienoic acid, as shown below:

5-benzo[1,3]dioxol-5-yl-penta-2,4-dienoic acid

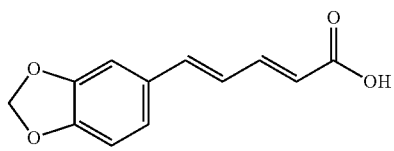 [SMILES: O=C(O)/C=C/C=C/c1ccc2c(c1)OCO2]

In some embodiments, 5-benzo[1,3]dioxol-5-yl-penta-2,4-dienoic acid is specifically excluded.

In some embodiments, a subject ALDH agonist is a compound of generic Formula Va, as shown below:

Formula Va

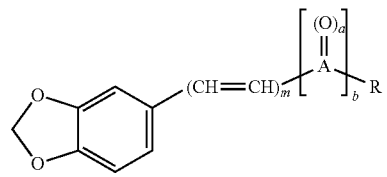

where m is an integer from 1 to 10;
where A is C or S; and where a=1 when A=C; and where a=2 when A=S;
where b is the integer 0 or 1;

where R is selected from a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; a substituted or unsubstituted heteroaryl group; a substituted or unsubstituted bicyclic group; a substituted or unsubstituted hetero bicyclic group; a substituted or unsubstituted polycyclic group; and a substituted or unsubstituted hetero polycyclic group;

or a pro-drug, a pharmaceutically acceptable salt, an analog, or a derivative thereof.

In some embodiments, the following compounds are exemplary, non-limiting compounds of Formula Va: piperine and methysticin.

In certain embodiments, 5-benzo[1,3]dioxol-5-yl-penta-2,4-dienoic acid is specifically excluded from compounds of Formula Va.

Whether a compound is an ALDH agonist can be readily ascertained. Assays for dehydrogenase activity of ALDH are known in the art, and any known assay can be used. Examples of dehydrogenase assays are found in various publications, including, e.g., Sheikh et al. ((1997) *J. Biol. Chem.* 272: 18817-18822); Vallari and Pietruszko (1984) *J. Biol. Chem.* 259:4922; and Farres et al. ((1994) *J. Biol. Chem.* 269:13854-13860).

Figure 4:
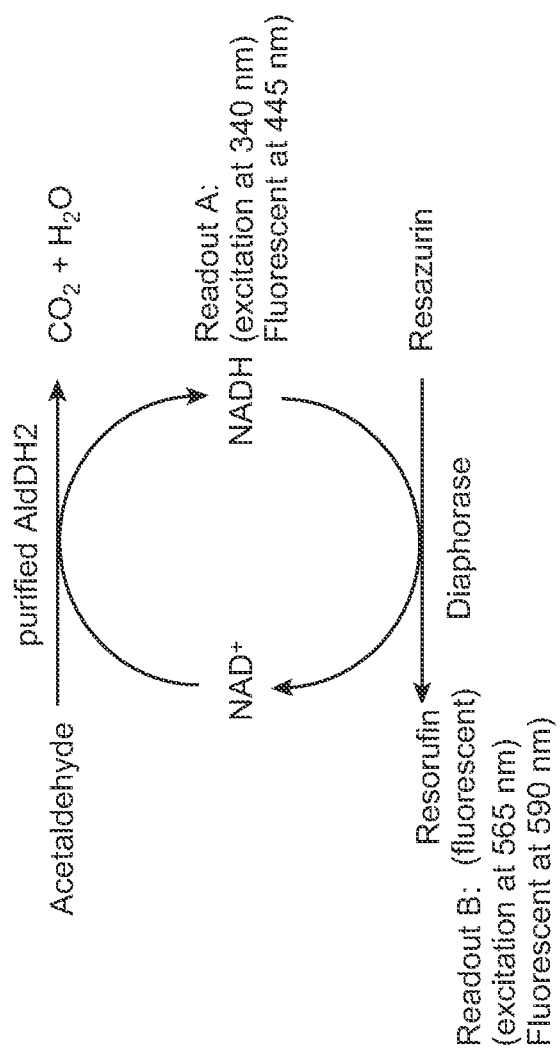
FIG. 4 schematically depicts an exemplary fluorescent aldehyde dehydrogenase enzymatic assay.
Figure 8:
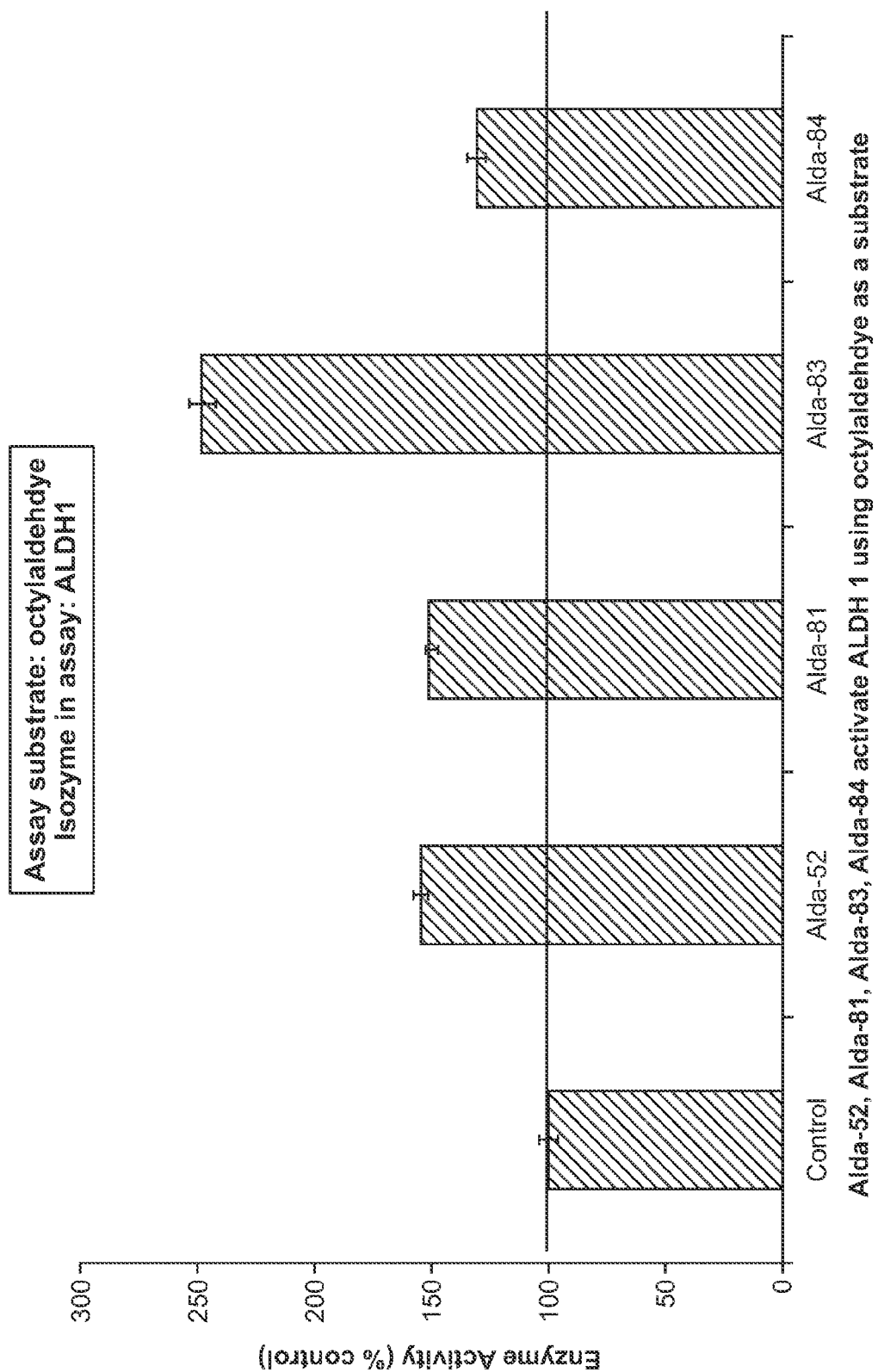
FIG. 8 depicts the effect of four exemplary activator compounds, Alda-52, Alda-81, Alda-83 and Alda-84, on ALDH1 enzymatic activity using octylaldehyde as a substrate.

As an example of an assay for dehydrogenase activity, ALDH aldehyde dehydrogenase activity is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and an aldehyde substrate such as 14 µM propionaldehyde. Reduction of $NAD^+$ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043; and WO 2005/057213, and as depicted schematically in FIG. 4. In an exemplary assay, the reaction is carried out at 25° C. in 0.1 sodium pyrophosphate (NaPPi) buffer, pH 9.0, 2.4 mM $NAD^+$ and 10 mM acetaldehyde as the substrate. Enzymatic activity is measured by a reductive reaction of $NAD^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213, and as depicted schematically in FIG. 4. Detection of fluorescent resorufin at 590 nm provides amplified and more sensitive signals for any change in ALDH aldehyde dehydrogenase enzymatic activity. $NADP^+$ can be used in place of $NAD^+$ in this assay. In some embodiments, a substrate other than the substrate depicted in FIG. 4 is used. Suitable substrates include, but are not limited to, octylaldehyde, phenylacetaldehyde, retinaldehyde, and 4-hydroxynonenal. Although the reaction depicted in FIG. 4 shows use of purified ALDH2, other ALDH polypeptides (e.g., ALDH1, ALDH3, ALDH5, etc.) can be used. The enzyme used in the assay can be purified (e.g., at least about 75% pure, at least about 80% pure, at least about 85% pure, at least about 90% pure, at least about 95% pure, at least about 98% pure, or at least about 99% pure). Recombinant ALDH enzyme can also be used in the assay.

As another example, the effect of a compound on aldehyde dehydrogenase activity of an ALDH polypeptide can be assayed as described in Wierzchowski et al. ((1996) *Analytica Chimica Acta* 319:209), in which a fluorogenic synthetic substrate, e.g., 7-methoxy-1-naphthaldehyde is used. For example, the reaction could include 7-methoxy-1-naphthaldehyde, NAD$^+$, an ALDH polypeptide, and an ALDH agonist to be tested; fluorescence (excitation, 330 nm; emission 390 nm) is measured as a readout of enzymatic activity.

Whether a compound increases an esterase activity of an ALDH polypeptide can be determined using any known assay for esterase activity. For example, esterase activity of ALDH can be determined by monitoring the rate of p-nitrophenol formation at 400 nm in 25 mM N,N-Bis (2-hydroxyethyl)-2-amino ethanesulfonic acid (BES) (pH 7.5) with 800 µM p-nitrophenyl acetate as the substrate at room temperature in the absence or presence of added NAD$^+$. A pH-dependent molar extinction coefficient of 16 mM$^{-1}$ cm$^{-1}$ at 400 nm for nitrophenol can be used. See, e.g., Larson et al. (2007) *J. Biol. Chem.* 282:12940). Esterase activity of ALDH2 can be determined by measuring the rate of p-nitrophenol formation at 400 nm in 50 mM Pipes (pH 7.4) with 1 mM p-nitrophenylacetate as the substrate. A molar extinction coefficient of 18.3×10$^3$ M$^{-1}$ cm$^{-1}$ at 400 nm for p-nitrophenolate can be used for calculating its rate of formation. See, e.g., Ho et al. (2005) *Biochemistry* 44:8022).

Whether a compound increases a reductase activity of ALDH can be determined using any known assay for reductase activity. A reductase activity of ALDH can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence ALDH2. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 µl in ethanol for subsequent TLC separation and scintillation counting. See, e.g., Zhang and Stamler (2002) *Proc. Natl. Acad. Sci. USA* 99:8306.

As noted above, in some embodiments, a subject ALDH agonist is pure, e.g., at least 80%, at least about 90% pure, at least about 98% pure, or at least about 99% pure, by weight.

Natural Extracts

The present disclosure also provides for ALDH agonists in natural extracts, e.g., extracts of plants and other organisms that naturally contain an ALDH agonist. Natural formulations and extracts can comprise an ALDH agonist in an amount by weight of from about 0.01% to about 30%, or from about 30% to about 80%, e.g., from about 0.01% to about 0.05%, from about 0.05% to about 0.1%, from about 0.1% to about 0.5%, from about 0.5% to about 1%, from about 1% to about 2.5%, from about 2.5% to about 5%, from about 5% to about 7.5%, from about 7.5% to about 10%, from about 10% to about 12.5%, from about 12.5% to about 15%, from about 15% to about 20%, from about 20% to about 25%, or from about 25% to about 30%. In some embodiments, a subject natural formulation or natural extract comprises an ALDH agonist in an amount by weight of from about 30% to about 35%, from about 35% to about 40%, from about 40% to about 45%, from about 45% to about 50%, from about 50% to about 60%, from about 60% to about 70%, or from about 70% to about 80%. As used herein, a "natural formulation" or a "natural extract" can include components of a plant or other natural source of an ALDH agonist, but does not exclude inclusion of components not normally found in a plant source of an ALDH agonist, e.g., the "natural formulation" or "natural extract" can include added components not normally found in a plant source or other natural source of an ALDH agonist.

A plant or plant part can be extracted either singly or sequentially with one or more of an aqueous solution, an alcohol, a polar organic solvent, and a non-polar organic solvent. In some embodiments, an ALDH agonist is water soluble (hydrophilic) and is present in an aqueous phase of a natural extract. For example, in some embodiments, a plant or plant part is extracted with 100% water. In other embodiments, an ALDH agonist is hydrophobic and is present in an organic phase of a natural extract. For example, a plant or a plant part can be extracted with an organic solvent such as ethyl acetate or methylene chloride. In some embodiments, the plant or plant part is extracted with alcohol, e.g., methanol or butanol. In some embodiments, the plant or plant part is extracted with methanol:chloroform (1:1 vol:vol). In some embodiments, the plant or plant part is extracted with methanol:water from 95:5 to 1:1. In some embodiments, the plant or plant part is extracted sequentially with an alcohol, then with an alcohol:chloroform mixture. Polar organic solvents include, e.g., tetrahydrofuran, acetonitrile, acetone, and isopropyl alcohol. In some embodiments, the plant or plant part is extracted with a polar organic solvent. Extraction methods are known in the art, and are described in, e.g., U.S. Pat. Nos. 7,282,150 and 7,172,772.

The natural extract can be obtained by extracting a plant or plant part at a temperature of from about 15° C. to about 20° C., from about 20° C. to about 25° C., from about 25° C. to about 30° C., from about 30° C. to about 35° C., from about 35° C. to about 40° C., from about 40° C. to about 45° C., from about 45° C. to about 50° C., from about 50° C. to about 60° C., from about 60° C. to about 70° C., from about 70° C. to about 80° C., from about 80° C. to about 90° C., or from about 90° C. to about 100° C.

A natural extract includes an extract of a whole plant or one or more parts of a plant, where plant parts include leaves, stems, rhizomes, roots, tubers, bulbs, flowers, bark, seeds, fruit, and the like. Thus, sources of an ALDH agonist include, e.g., whole plant or one or more parts of a plant, where plant parts include leaves, stems, rhizomes, tubers, bulbs, roots, flowers, bark, seeds, fruit, and the like. Prior to extraction, the plant or plant part can be subjected to one or more processing steps; e.g., prior to extraction, the plant or plant part can be dried, powdered, frozen, steamed, ground, pulverized, or fermented. Pulverizing can be achieved by carrying out one or more of homogenizing, milling, grinding, chopping, blending, cutting, and tearing.

Combinations of two or more extracts are also contemplated, e.g., extracts of two or more different plant parts from the same plant; extracts from two or more plants of the same genus, where the plants are of two or more different species; extracts from two or more plants of two or more different genuses; a combination of an aqueous extract and an alcohol extract; a combination of an aqueous extract and a polar organic solvent extract; a combination of an aqueous extract and a non-polar organic solvent extract; etc.

A subject natural extract can be formulated in any form convenient for use, e.g., a lozenge, a capsule, a powder, a liquid solution, a gel, etc. Any of a variety of components can be added to a natural extract, including, e.g., fillers, binders, sweeteners, flavors and other ingredients. Nearly any excipients that are known for use in the preparation of oral dosage pharmaceutical products, or natural supplement products, can be used. Examples of such excipients include without limitation, carbomer, carboxymethylcellulose sodium, cellulose, dextrin, dextrose, ethylcellulose, fructose, gelatin, guar gum, hydroxyethyl cellulose, hydroxypropyl cellulose, hydroxypropyl methylcellulose, glucose, maltodextrin, mannitol, methylcellulose, microcrystalline cellulose, polymethacrylates, povidone, sorbitol, starches, sucrose, sugar, sucralose, stevia, and flavor agents.

Pharmaceutical Compositions, Dosages, Routes of Administration

The present disclosure provides pharmaceutical compositions comprising a subject ALDH agonist. The terms "ALDH agonist" and "ALDH activator" are also referred to herein as "active agent." A subject ALDH agonist is formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for a subject active agent depend on the particular compound employed and the effect to be achieved, and the pharmacodynamics associated with each compound in the host.

In the subject methods, a subject ALDH agonist may be administered to the host using any convenient means capable of resulting in the desired outcome, e.g., reduction of disease, reduction of a symptom of a disease, etc. Thus, a subject ALDH agonist can be incorporated into a variety of formulations for therapeutic administration. More particularly, a subject ALDH agonist can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

In pharmaceutical dosage forms, a subject ALDH agonist ("active agent") may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, a subject active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject active agent can be utilized in aerosol formulation to be administered via inhalation. A subject active agent can be formulated into pressurized acceptable propellants such as dichlorodifluoromethane, propane, nitrogen and the like.

Furthermore, a subject active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

A subject active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Ocular Formulations

A subject active agent can be formulated for ocular delivery, e.g., where a subject active agent is formulated for delivery to the eye in liquid form (e.g., eye drops), or for injection into or around the eye.

A subject active agent can be formulated in an ophthalmic pharmaceutical composition. Ophthalmic pharmaceutical compositions can be adapted for topical administration to the eye in the form of solutions, suspensions, ointments, creams or as a solid insert. Ophthalmic formulations of comprising a subject active agent can contain from 0.01 to 5%, or from 0.1 to 2% of a subject active agent. Higher dosages as, for example, about 10% or lower dosages can be employed provided the dose is effective in treating a disorder of the eye (e.g., cataracts). For a single dose, from between 0.001 to 5.0 mg, e.g., from 0.005 to 2.0 mg, or from 0.005 to 1.0 mg of a subject active agent can be applied to the human eye.

A subject active agent can be conveniently admixed with a non-toxic pharmaceutical organic carrier, or with a non-toxic pharmaceutical inorganic carrier. Suitable pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate, cyclodextrin (Loftsson and Sefansson (2002) Acta Ophthalmol. Scand. 80:144), and other conventionally employed acceptable carriers. The pharmaceutical preparation can also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitate, dioctyl sodium sulfosuccinate, monothioglycerol, thiosorbitol, ethylenediamine tetracetic acid, and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation can also be in the form of a microparticle formulation. The pharmaceutical preparation can also be in the form of a solid insert. For example, one may use a solid water soluble polymer as the carrier for the medicament. The polymer used to form the insert can be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

A pharmaceutical preparation comprising a subject active agent can further include one or more non-toxic auxiliary substances such as antibacterial components which are non-injurious in use, for example, thimerosal, benzalkonium chloride, methyl and propyl paraben, benzyldodecinium bromide, benzyl alcohol, chlorhexidine, or phenylethanol; buffering ingredients such as sodium borate, sodium acetate, sodium citrate, or gluconate buffers; and other conventional ingredients such as sodium chloride, sorbitan monolaurate, triethanolamine, polyoxyethylene sorbitan monopalmitate, ethylenediaminetetraacetic acid, and the like.

Topical Formulations

A subject active agent can be formulated for topical administration to the skin. For example, a subject active agent can be formulated with one or more dermatologically acceptable excipients.

The term "dermatologically acceptable," as used herein, means that the compositions or components thereof so described are suitable for use in contact with human skin without undue toxicity, incompatibility, instability, allergic response, and the like.

In some embodiments, a subject active agent is formulated with a dermatologically active acid. Suitable dermatologically active acids include a hydroxy acid, ascorbic acid, glycolic acid, magnesium ascorbyl phosphate, sodium ascorbyl phosphate, sodium ascorbate, ascorbyl glucosides, salicylic acid, lipoic acid, dihydrolipoic acid, and combinations thereof. In some embodiments, the dermatologically active acid is alpha-hydroxy acid. Alpha-hydroxy acids include, malic acid, tartaric acid, lactic acid, pyruvic acid, citric acid, and combination of any of the foregoing. In some embodiments, a subject active agent is formulated with a dermatologically active acid and one or more of: mmonium hydroxide, alkali hydroxide, alkanolamone, amino acid, sodium hydroxide, potassium hydroxide, diethanolamine, triethanolamine, 2-dimethylaminoethanol (dimethyl MEA), aminobutanol, arginine, and lysine.

Suitable excipients include emollients; humectants; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and the like.

A variety of emollients may be employed to yield the conditioning component of the present disclosure. These emollients may be selected from one or more of the following classes: triglyceride esters that include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; acetoglyceride esters, such as acetylated monoglycerides; alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; wax esters such as beeswax, spermaceti, myristyl myristate, stearyl stearate; forming a mixture of ether esters; and vegetable waxes including, but not limited to, carnauba and candelilla waxes; and cholesterol fatty acid esters.

Humectants of the polyhydric alcohol-type are suitable for use. Typical polyhydric alcohols include polyalkylene glycols and more preferably alkylene polyols and their derivatives, including propylene glycol, dipropylene glycol, tripropylene glycol, polyethylene glycol and derivatives thereof, sorbitol, hydroxypropyl sorbitol, erythritol, threitol, pentaerythritol, xylitol, glucitol, mannitol, hexylene glycol, 1,3-butylene glycol, 1,2,6-hexanetriol, glycerol, ethoxylated glycerol, propoxylated glycerol, sodium 2-pyrrolidone-5-carboxylate, soluble collagen, gelatin and mixtures thereof.

Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and mixtures thereof.

A composition comprising a subject active agent can include a dermatologically-acceptable hydrophilic diluent. Non-limiting examples of hydrophilic diluents are water, organic hydrophilic diluents such as lower monovalent alcohols (e.g., $C_1$-$C_4$ alcohols) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. A composition comprising a subject active agent can contain from about 60% to about 99.99% of a hydrophilic diluent.

A composition comprising a subject active agent can include a dermatologically acceptable carrier. An example of a suitable carrier is an emulsion comprising a hydrophilic phase comprising a hydrophilic component, e.g., water or other hydrophilic diluent, and a hydrophobic phase comprising a hydrophobic component, e.g., a lipid, oil or oily material. The hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions can comprise from about 1% to about 50% of the dispersed hydrophobic phase and from about 1% to about 98% of the continuous hydrophilic phase; water-in-oil emulsions can comprise from about 1% to about 98% of the dispersed hydrophilic phase and from about 1% to about 50% of the continuous hydrophobic phase.

A subject active agent can be formulated with common excipients, diluents, or carriers, and formed into lotions, creams, solutions, suspensions, powders, aerosols, emulsions, salves, ointments and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinylpyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. A composition comprising a subject ALDH agonist can include thickening agents such as cellulose and/or cellulose derivatives. A composition comprising a subject ALDH agonist can include contain gums such as xanthan, guar or carbo gum or gum arabic, or alternatively poly(ethylene glycol)s, bentones and montmorillonites, and the like.

A composition comprising a subject ALDH agonist can further include one or more additional agents such as, for example, antioxidants, surfactants, preservatives, film-forming, keratolytic or comedolytic agents, perfumes, flavorings, and colorings. Antioxidants such as t-butylhydroquinone, butylated hydroxyanisole, butylated hydroxytoluene and α-tocopherol and its derivatives can be added.

A composition comprising a subject ALDH agonist can further include, e.g., retinaldehyde (e.g., 0.01% to about 1%, e.g., 0.1%), glycolic acid (e.g., 2% to about 10%, e.g., 6%), etc.

Furthermore, composition comprising a subject ALDH agonist can further include one or more additional therapeutic agents, for example, anti-microbial agents, pain relievers, anti-inflammatory agents, and the like, depending, e.g., on the condition being treated.

Continuous Delivery

In some embodiments, a subject active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with a subject method. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use in a subject method. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in conjunction with a subject treatment method include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of a subject active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for use in a subject method is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Oral Formulations

In some embodiments, a subject active agent is formulated for oral delivery to an individual in need of such an agent.

For oral delivery, a subject formulation comprising a subject active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, a subject active agent is formulated with one or more pharmaceutical excipients and coated with an enteric coating, as described in U.S. Pat. No. 6,346,269. For example, a solution comprising a subject active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for a subject active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include a subject active agent formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include a subject active agent with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Trilayer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Oral Cavity Formulations

Oral formulations further include mouth rinses, chewing gum, lozenges, and the like, where the oral formulation comprises an ALDH agonist, and where the formulation is meant to stay in the oral cavity for from about 15 seconds to about 2 hours, or longer than 2 hours. For example, in some embodiments, a subject oral formulation is suitable for remaining in the oral cavity for a period of from about 15 second to about 30 seconds, from about 30 seconds to about 60 seconds, from about 1 minute to about 5 minutes, from about 5 minutes to about 15 minutes, from about 15 minutes to about 30 minutes, from about 30 minutes to about 1 hour, from about 1 hour to about 2 hours, or more than 2 hours. Exemplary oral formulations include, e.g., a mouth wash, a mouth rinse, chewing gum, a lozenge, a mouth strip, a mouth spray, a toothpaste, a tooth gel, a tooth powder, etc.

The choice of a carrier to be used can be determined by the way the composition is to be introduced into the oral cavity. If a toothpaste (including tooth gels, etc.) is to be used, then a "toothpaste carrier" is chosen (comprising e.g., abrasive materials, sudsing agents, binders, humectants, flavoring and sweetening agents, etc.) as disclosed in e.g., U.S. Pat. No. 3,988,433. If a mouth rinse is to be used, then a "mouth rinse carrier" is chosen (comprising e.g., water, flavoring, and sweetening agents, etc.), as disclosed in e.g., U.S. Pat. No. 3,988,433. Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955; if a chewing gum is to be used, a "chewing gum carrier" is chosen (comprising e.g., gum base, flavoring and sweetening agents), as disclosed in e.g., U.S. Pat. No. 4,083,955. If a sachet is to be used, then a "sachet carrier" is chosen (e.g., sachet bag, flavoring and sweetening agents). Carriers suitable for the preparation of a subject oral formulation are well known in the art. Their selection can depend on secondary considerations such as taste, cost, and shelf stability.

In addition to an ALDH agonist and one or more carriers, a subject oral cavity formulation can include one or more additional agents, e.g., an anticaries agent (from about 0.05% to about 0.3% as fluoride ion); an anticalculus agent (from about 0.1% to about 13%); a teeth whitening agent; an anti-microbial agent; an enzyme; and the like.

In some embodiments, a subject oral composition for use in the oral cavity is a toothpaste, a tooth gel, or a tooth powder. Components of such toothpaste and tooth gels generally include one or more of a dental abrasive (from about 5% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Chewing gum compositions can include, in addition to an ALDH agonist, one or more of a gum base (from about 50% to about 99%), a flavoring agent (from about 0.4% to about 2%) and a sweetening agent (from about 0.01% to about 20%).

Suitable mouthwashes, including mouth sprays, can include, in addition to an ALDH agonist, one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays can also include one or more of an anticaries agent (from about 0.05% to about 0.3% as fluoride ion), and an anticalculus agent (from about 0.1% to about 3%).

A subject lozenge includes, in addition to an ALDH agonist, one or more suitable components. "Lozenge," as used herein, includes: breath mints; troches; pastilles; microcapsules; and fast-dissolving solid forms including freeze dried forms (cakes, wafers, thin films, tablets); and compressed tablets. The term "fast-dissolving solid form" as used herein means that the solid dosage form dissolves in less than about 60 seconds, less than about 15 seconds, or less than about 5 seconds, after placing the solid dosage form in the oral cavity. Fast-dissolving solid forms are disclosed in, e.g., WO 95/33446 and WO 95/11671. Lozenges include discoidshaped solids comprising a therapeutic agent in a flavored base. The base may be a hard sugar candy, glycerinated gelatin or combination of sugar with sufficient mucilage to give it form. These dosage forms are generally described in Remington: The Science and Practice of Pharmacy, 19.sup.th Ed., Vol. II, Chapter 92, 1995. Lozenge compositions (compressed tablet type) can include one or more fillers (compressible sugar), flavoring agents, and lubricants. Suitable microcapsules are disclosed in, e.g., U.S. Pat. No. 5,370,864.

Where a subject oral formulation comprises an abrasive, suitable abrasives include, e.g., silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Where a subject oral formulation comprises a surfactant, suitable surfactants include, e.g., sarcosinate surfactants, isethionate surfactants and taurate surfactants. Suitable surfactants include alkali metal or ammonium salts of sarcosinate surfactants, isethionate surfactants and taurate surfactants. For example, suitable surfactants include sodium and potassium salts of the following: lauroyl sarcosinate, myristoyl sarcosinate, palmitoyl sarcosinate, stearoyl sarcosinate and oleoyl sarcosinate. Suitable anionic surfactants include the water-soluble salts of alkyl sulfates having from 10 to 18 carbon atoms in the alkyl radical and the water-soluble salts of sulfonated monoglycerides of fatty acids having from 10 to 18 carbon atoms; sodium lauryl sulfate and sodium coconut monoglyceride sulfonates are examples of anionic surfactants of this type. Suitable cationic surfactants include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; and the like. Suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. Suitable zwitterionic synthetic surfactants include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable betaine surfactants include alkyl dimethyl betaines and amidobetaines. Alkyl dimethyl betaines include decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like.

As noted above, a subject oral formulation can include an anticalculus agent. Suitable anticalculus agents include synthetic anionic polymers, including polyacrylates and copolymers of maleic anhydride or acid and methyl vinyl ether (e.g., Gantrez), as well as, e.g., polyamino propane sulfonic acid (AMPS), zinc citrate trihydrate, polypeptides (such as polyaspartic and polyglutamic acids), and mixtures thereof.

As noted above, a subject oral formulation can include an anticaries agent such as fluoride. Suitable fluoride ion sources include stannous fluoride, sodium fluoride, potassium fluoride, sodium monofluorophosphate, etc.

As noted above, a subject oral formulation can include a teeth whitening agent, where suitable teeth whitening agents include, e.g., mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof.

Suitable humectants include, e.g., edible polyhydric alcohols such as glycerin, sorbitol, xylitol, butylene glycol, polyethylene glycol, and propylene glycol, especially sorbitol and glycerin.

Suitable thickening agents include, e.g., polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. An exemplary class of thickening or gelling agents includes a class of homopolymers of acrylic acid crosslinked with an alkyl ether of pentaerythritol or an alkyl ether of sucrose, or carbomers. Copolymers of lactide and glycolide monomers, the copolymer having the molecular weight in the range of from about 1,000 to about 120,000 (number average) can also be used.

Suitable flavoring agents include, e.g., oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof.

Suitable sweetening agents include, e.g., sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof.

A subject oral formulation can include an antimicrobial agent. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquamide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (e.g., an alkyl or benzyl group) have a lower number of carbon atoms, such as from about 1 to about 7 carbon atoms, e.g., methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl-hexahydropyrimidine, benzalkonium chloride, benzethonium chloride and methyl benzethonium chloride are exemplary of typical quaternary ammonium antibacterial agents. Other suitable compounds include bis[4-(R-amino)-1-pyridinium] alkanes. Other suitable antimicrobials such as copper bisglycinate, copper glycinate, zinc citrate, and zinc lactate may also be included. Other antimicrobial agents include chlorhexidine, triclosan, triclosan monophosphate, and flavor oils such as thymol.

A subject oral formulation can further include one or more enzymes. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranases, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to antimicrobial properties.

Dental Implements

The dental implement comprises an implement for contact with teeth and other tissues in the oral cavity, where the dental implement is coated and/or impregnated with a composition comprising an ALDH agonist. The dental implement can be impregnated fibers including dental floss or tape; chips; strips; films; and polymer fibers.

Inhalational Formulations

A subject ALDH agonist will in some embodiments be administered to a patient by means of a pharmaceutical delivery system for the inhalation route. A subject ALDH agonist can be formulated in a form suitable for administration by inhalation. The inhalational route of administration provides the advantage that the inhaled drug can bypass the blood-brain barrier. The pharmaceutical delivery system is one that is suitable for respiratory therapy by delivery of a subject ALDH agonist to mucosal linings of the bronchi. This invention can utilize a system that depends on the power of a compressed gas to expel the subject ALDH agonist from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains a subject ALDH agonist, which can be dissolved, suspended, or emulsified in a mixture of a fluid carrier and a propellant. The aerosol can be in the form of a solution, suspension, emulsion, powder, or semi-solid preparation. Aerosols are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

A subject ALDH agonist can also be formulated for delivery with a nebulizer, which is an instrument that generates very fine liquid particles of substantially uniform size in a gas. For example, a liquid containing the subject ALDH agonist is dispersed as droplets. The small droplets can be carried by a current of air through an outlet tube of the nebulizer. The resulting mist penetrates into the respiratory tract of the patient.

A powder composition containing a subject ALDH agonist, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with a subject method, where an ALDH agonist is delivered via inhalation. A subject ALDH agonist can be formulated in basically three different types of formulations for inhalation. First, a subject ALDH agonist can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, a subject ALDH agonist can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

A subject ALDH agonist can be formulated into dry powder formulations. Such formulations can be administered by simply inhaling the dry powder formulation after creating an aerosol mist of the powder. Technology for carrying such out is described within U.S. Pat. Nos. 5,775,320 and 5,740,794.

Dosages and Dosing

Depending on the subject and condition being treated and on the administration route, the subject compounds may be administered in dosages of, for example, 0.1 µg to 500 mg/kg body weight per day, e.g., from about 0.1 µg/kg body weight per day to about 1 µg/kg body weight per day, from about 1 µg/kg body weight per day to about 25 µg/kg body weight per day, from about 25 µg/kg body weight per day to about 50 µg/kg body weight per day, from about 50 µg/kg body weight per day to about 100 µg/kg body weight per day, from about 100 µg/kg body weight per day to about 500 µg/kg body weight per day, from about 500 µg/kg body weight per day to about 1 mg/kg body weight per day, from about 1 mg/kg body weight per day to about 25 mg/kg body weight per day, from about 25 mg/kg body weight per day to about 50 mg/kg body weight per day, from about 50 mg/kg body weight per day to about 100 mg/kg body weight per day, from about 100 mg/kg body weight per day to about 250 mg/kg body weight per day, or from about 250 mg/kg body weight per day to about 500 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, a subject ALDH2 activity modulator can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is in some embodiments one which provides up to about 1 µg to about 1,000 µg or about 10,000 µg of subject compound in a blood sample taken from the individual being treated, about 24 hours after administration of the compound to the individual.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound(s) in a composition as a solution in sterile water, normal saline or another pharmaceutically acceptable carrier.

In some embodiments, multiple doses of a subject compound are administered. The frequency of administration of a subject compound ("active agent") can vary depending on any of a variety of factors, e.g., severity of the symptoms, etc. For example, in some embodiments, a subject compound is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in some embodiments, a subject compound is administered continuously.

The duration of administration of a subject compound, e.g., the period of time over which a subject compound is administered, can vary, depending on any of a variety of factors, e.g., patient response, etc. For example, a subject compound can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, a subject compound is administered for the lifetime of the individual.

Routes of Administration

A subject ALDH agonist is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, ocular (e.g., topically to the eye, intravitreal, etc.), rectal, nasal, oral, and other enteral and parenteral routes of administration. Routes of administration may be combined, if desired, or adjusted depending upon the agent and/or the desired effect. The compound can be administered in a single dose or in multiple doses.

A subject active agent can be administered to a host using any available conventional methods and routes suitable for delivery of conventional drugs, including systemic or localized routes. In general, routes of administration contemplated by the invention include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, ocular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of a subject ALDH agonist through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Treatment Methods

The present disclosure provides various treatment methods, generally involving administering to an individual in need thereof an effective amount of a subject agonist. A subject ALDH agonist is suitable for treating a variety of disorders, including, e.g., conditions involving ischemic stress, oxidative stress, chronic free-radical associated diseases, acute free-radical associated diseases, insensitivity to nitroglycerin (e.g., in angina and heart failure), hypertension, peripheral artery disease, diabetes, cataract, age-related macular degeneration, lung diseases that result from cigarette smoking, cancer, neurodegenerative diseases, and osteoporosis. A subject ALDH agonist is suitable for sensitizing a cancerous cell to a cancer chemotherapeutic agent or other standard cancer therapy; for treating alcohol (e.g., ethanol; ethyl alcohol) intolerance; for treating alcohol (e.g., ethanol; ethyl alcohol) addiction; and for treating narcotic addiction.

Methods of Treating Conditions Involving Ischemic Stress

The present disclosure provides methods for treating conditions involving ischemic stress, including prophylactic methods, in an individual, the methods generally involving administering to an individual in need thereof an effective amount of a subject ALDH agonist. Conditions involving ischemic stress include ischemic conditions, ischemic events, conditions that can give rise to ischemia, and conditions that result from an ischemic event. Conditions involving ischemic stress that are amenable to treatment with a subject method include ischemia that result from any condition or event, including, but not limited to, myocardial infarct (e.g., acute myocardial infarction), cardiac surgery, brain trauma, cerebrovascular disease, stroke, spinal cord injury, subarachnoid hemorrhage, major surgery in which ischemia to variety of organs occur, organ transplantation, limb ischemia (e.g., resulting from Type 1 or Type 2 diabetes), peripheral artery disease, and the like.

In some embodiments, the agent is administered before a predicted or anticipated ischemic event, e.g., from about 1 hour to about 1 week before the ischemic event, e.g., from about 1 hour to about 2 hours, from about 2 hours to about 4 hours, from about 4 hours to about 8 hours, from about 8 hours to about 12 hours, from about 12 hours to about 16 hours, from about 16 hours to about 24 hours, from about 24 hours to about 36 hours, from about 36 hours to about 48 hours, from about 48 hours to about 72 hours, or from about 72 hours to about 1 week preceding the predicted or anticipated ischemic event.

Pretreatment with an active agent is desirable under certain circumstances, for example, when a subject has already experienced a stroke, when a subject is about to undergo cardiac surgery, etc. For example, a patient who has already experienced a stroke will have an increased probability of experiencing a second stroke. Subjects who are susceptible to transient ischemic attacks also have an increased risk of a stroke. Subjects who suffer a subarachnoid hemorrhage may experience further ischemic events induced by vasospasms that constrict the blood vessels. Subjects who experience trauma to organs such as the brain are also susceptible to an ischemic event. Subjects undergoing surgery over an extended period of time are also susceptible to an ischemic event. The above situations exemplify circumstances when a subject would benefit from pretreatment with a subject ALDH agonist.

In some embodiments, a subject ALDH agonist is administered after an ischemic event. For example, a subject ALDH agonist is effective in reducing the adverse effects of an ischemic event such as cardiac ischemia, reperfusion injury, cerebrovascular disease, acute myocardial infarction, subarachnoid hemorrhage, and trauma. In some embodiments, a subject ALDH agonist is administered within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following the ischemic event. In some embodiments, an increased concentration of a subject ALDH2 agonist is maintained in the plasma for at least several hours to several days following the ischemic event.

For example, in some embodiments, a subject ALDH agonist is administered to an individual who has suffered an acute myocardial infarction (AMI) within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following the AML Methods of Treating Ocular Disorders The present disclosure provides methods for treating ocular disorders, e.g., cataracts, the methods generally involving administering to an individual in need thereof an effective amount of a subject ALDH agonist. In some embodiments, the ALDH agonist will be an ALDH3 agonist. The ALDH agonist will be formulated for ocular administration, e.g., for topical administration to the eye, for injection into the eye (e.g., intravitreal injection), or some other route of administration to the eye. Ocular disorders that can be treated with a subject ALDH agonist include, e.g., age-related cataracts, secondary cataracts, traumatic cataracts, congenital cataracts, age-related macular degeneration, radiation cataracts, etc.

Among the risk factors for cataract are exposure to UV-light (which can result in generation of toxic aldehydes such as 4-hydroxy-2-nonenal), exposure to cigarette smoke (cigarette smoke contains high amounts of reactive aldehydes, such as acrolein). See, e.g., Jia et al., Invest Ophthalmol V is Sci. 2007 January; 48(1):339-48. PMID: 17197552; J Dong et al., Neurochem. 2007 November; 103(3):1041-52. PMID: 17935603; Papa et al., Free Radic Biol Med. 2003 May 1; 34(9):1178-89. PMID: 12706498; King et al. J Exp Zool. 1998 Sep.-Oct. 1; 282(1-2):12-7. PMID: 9723161). The instant disclosure provides methods of treating cataracts, the methods generally involving administering to an individual in need thereof an effective amount of an ALDH agonist, e.g., a subject ALDH agonist.

A subject ALDH agonist can be administered to an individual in need thereof for the treatment of an ocular disorder (e.g., cataracts, age-related macular degeneration, etc.), where the ALDH agonist is administered topically to the eye, e.g., in the form of eyedrops. Alternatively, a subject ALDH agonist can be administered by another ocular route of administration, e.g., intravitreally.

A subject ALDH agonist can be administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), for the treatment of an ocular disorder. A subject ALDH agonist can be administered over a period of time of from about 3 months to about 1 year, from 1 year to 10 years, or more than 10 years.

In some embodiments, where a subject ALDH agonist is administered for the treatment of cataracts, the ALDH agonist is administered before or after surgery for cataracts.

Methods of Treating Skin Disorders

The present disclosure provides methods for treating skin disorders, the methods generally involving administering to an individual in need thereof an effective amount of a subject ALDH agonist.

Skin disorders that can be treated with a subject ALDH agonist include, but are not limited to, radiation dermatitis, atopic dermatitis, sunburn, ultraviolet radiation damage to the skin, skin aging, and premature hair loss.

In some embodiments, for the treatment of a skin disorder, a subject ALDH agonist is administered topically to the skin, e.g., to an area of skin affected by a skin disorder.

The present disclosure further provides methods of reducing at least the appearance fine lines, wrinkles, skin roughness, and pore size. The methods generally involve topically administering to the skin of an individual an effective amount of a subject ALDH agonist. In some of these embodiments, a subject ALDH agonist is one that increases the activity of an ALDH enzyme in converting retinaldehyde to retinoic acid. In some of these embodiments, a subject ALDH agonist is formulated for topical administration to the skin, as described above. In some embodiments, a subject ALDH agonist is formulated together with retinaldehyde. See, e.g., U.S. Pat. No. 6,544,531. In some embodiments, a subject ALDH agonist is formulated together with retinaldehyde and glycolic acid.

The present disclosure further provides methods of treating acne. The methods generally involve topically administering to the skin of an individual an effective amount of a subject ALDH agonist. In some of these embodiments, a subject ALDH agonist is one that increases the activity of an ALDH enzyme in converting retinaldehyde to retinoic acid.

Methods of Treating Radiation-induced Damage to Epithelial Cells

The present disclosure provides methods of treating radiation- and chemotherapy-induced damage to epithelial cells. Radiation, used in cancer therapy, can cause damage to epithelial cells, resulting in disorders such as radiation mucositis and radiation dermatitis. Cancer chemotherapy can also cause mucositis. The present disclosure provides methods of treating mucositis, the methods generally involving administering to an individual in need thereof (e.g., an individual who has undergone radiation treatment for head and neck cancer, and who has radiation mucositis as a result of the cancer treatment; an individual who has undergone radiation of the pelvis or abdomen, for treatment of a cancer, and who has mucositis as a result of the radiation; an individual who has undergone cancer chemotherapy and who has mucositis as a result of the chemotherapy) an effective amount of a subject ALDH agonist.

The present disclosure provides methods of treating radiation dermatitis, the methods generally involving administering to an individual in need thereof an effective amount of an ALDH agonist. The ALDH agonist will in some embodiments be a subject ALDH agonist. In other embodiments, the ALDH agonist is an ALDH agonist as disclosed in, e.g., WO 2008/122164. Radiation dermatitis can result from cancer radiotherapy, cardiac catheterization (see, e.g., Schecter et al. (2003) *J. Drugs Dermatol.* 2:425), and fluoroscopic procedures. A subject method is suitable for treating radiation dermatitis resulting from exposure to one or more of proton radiation, fluoroscopic radiation, ultraviolet radiation, alpha radiation, beta radiation and gamma radiation. In some embodiments, a subject method provides for treatment of radiation dermatitis that occurs as a result of cancer radiotherapy. A subject method can also be used to treat persons exposed to radiation as a result of a radiation attack, a nuclear accident, or other radiation exposure.

A subject method of treating radiation dermatitis can ameliorate one or more symptoms of radiation dermatitis. Thus, in some embodiments, an "effective amount" of an ALDH agonist is an amount that ameliorates one or more symptoms of radiation dermatitis, e.g., reduces the severity of one or more adverse symptoms of radiation dermatitis, where such symptoms include, e.g., epilation, edema, dry desquamation, wet desquamation, ulceration, bleeding, and skin cell necrosis. In some embodiments, an "effective amount" of an ALDH agonist is an amount that reduces the severity and/or duration of the radiation dermatitis by at least about 10%, at least about 15%, at least about 20%, at least about 25%, at least about 30%, at least about 40%, at least about 50%, at least about 60%, at least about 70%, or more than 70%, compared to the severity and/or duration in the absence of treatment with an ALDH agonist.

An ALDH agonist, or a formulation comprising an ALDH agonist, is applied to one or more of the skin, the scalp, the mouth, the nasoesophageal system, the gastrointestinal tract, and the urogenital system.

A subject method of treating radiation dermatitis includes the step of topically applying a subject composition comprising an ALDH agonist to an area of skin prior to, during, or after exposure of that area of skin to radiation.

In some embodiments, a composition comprising an effective amount of an ALDH agonist is applied to the skin (e.g., the affected area, or the area to be affected) one to six times daily, as needed.

In some embodiments, a composition comprising an effective amount of an ALDH agonist is applied to the skin of an individual before the individual is exposed to ionizing radiation. For example, in some embodiments, a composition comprising an effective amount of an ALDH agonist is applied to the skin of an individual from about 5 minutes to about 15 minutes, from about 15 minutes to about 30 minutes, from about 30 minutes to about 1 hour, from about 1 hour to about 4 hours, from about 4 hours to about 8 hours, from about 8 hours to about 12 hours, from about 12 hours to about 18 hours, from about 18 hours to about 24 hours, from about 1 day to about 2 days, from about 2 days to about 3 days, from about 3 days to about 4 days, or from about 4 days to about 5 days, prior to exposure of the individual to ionizing radiation (e.g., cancer radiotherapy). In some embodiments, multiple applications of an ALDH agonist are carried out within a time period of from about 12 hours to about 24 hours, from about 1 day to about 2 days, from about 2 days to about 3 days, from about 3 days to about 4 days, or from about 4 days to about 5 days, prior to exposure of the individual to ionizing radiation.

In other embodiments, a composition comprising an effective amount of an ALDH agonist is applied to the skin of an individual after the individual is exposed to ionizing radiation, e.g., an effective amount of an ALDH agonist is applied to the skin of an individual from about 5 minutes to about 10 minutes, from about 10 minutes to about 15 minutes, from about 15 minutes to about 30 minutes, from about 30 minutes to about 1 hour, from about 1 hour to about 4 hours, from about 4 hours to about 8 hours, from about 8 hours to about 12 hours, from about 12 hours to about 18 hours, or from about 18 hours to about 24 hours, following exposure of the individual to ionizing radiation.

In other embodiments, a composition comprising an effective amount of an ALDH agonist is applied to the skin of an individual both before the individual is exposed to ionizing radiation and after the individual is exposed to ionizing radiation.

Multiple applications of an ALDH agonist can be carried out, e.g., multiple topical applications to the skin of an individual who is about to undergo cancer radiotherapy or who has undergone cancer radiotherapy. For example, an ALDH agonist can be applied to the skin once daily, twice daily, three times daily, four times daily, once every other day, twice per week, or once per week, as appropriate, where the frequency of administration of an ALDH agonist to the skin of an individual will depend on various factors including, e.g., the severity of the radiation dermatitis, the anticipated severity of the radiation dermatitis, the age of the individual, etc.

The radiation therapy can include, e.g., 1.8 Gy per day to 2 Gy per day, or 1.5 Gy per day to 1.8 Gy per day. For example, radiation therapy can include 20 Gy to 40 Gy, 45 Gy to 60 Gy, or 60 Gy to 80 Gy, which can be fractionated (e.g., such that the individual receives 1.5 Gy per day to 1.8 Gy per day, or 1.8 Gy per day to 2 Gy per day).

In some embodiments, a subject method provides for an increase in the tolerated dose of ionizing radiation. Thus, in some embodiments, a subject treatment method involves: a) administering to an individual in need thereof (e.g., an individual having a cancer that is treatable with cancer radiotherapy) a dose of ionizing radiation; and b) administering topically or locally to the individual an effective amount of an ALDH agonist, where the ALDH agonist is effective to reduce the extent or severity of radiation dermatitis, and where the dose of ionizing radiation is at least about 10%, at least about 15%, at least about 20%, at least about 25%, at least about 30%, or more than 30%, higher than the dose that the individual would be able to tolerate in the absence of treatment with the ALDH agonist.

ALDH Agonists

As noted above, in some embodiments, an ALDH agonist administered in connection with a subject method of treating radiation-induced damage to epithelial cells will be a subject ALDH agonist. In other embodiments, the ALDH agonist is an ALDH agonist as disclosed in, e.g., WO 2008/122164.

ALDH agonists disclosed in WO 2008/122164 and suitable for use in connection with a subject method of treating radiation-induced damage to epithelial cells include a compound of generic formula VI, as shown below:

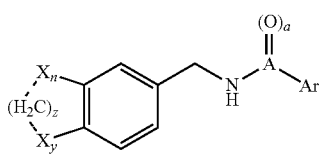

Formula VI where $X_n$ and $X_y$ are each independently H, C, N, O, or a halogen (e.g., F, Br, Cl, or I);

where ⋯ (dotted line) is an optional bond;

where z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where n is the integer 0 or 1;

where y is the integer 0 or 1;

where A=C or S, and where a=1 when A=C; and where a=2 when A=S;

where Ar is a phenyl or thiophene ring; wherein the Ar is optionally substituted at the position(s) ortho to the carbonyl or sulfonyl group by one or more substituents independently selected from methyl, halo, trifluoromethyl, or phenyl; wherein Ar is optionally substituted by a halogen meta or para to the carbonyl or sulfonyl group; and wherein, when Ar is a thiophene ring, the carbonyl or sulfonyl group is attached to a thiophene ring at the 2 or 3 position;

or a pro-drug, a pharmaceutically acceptable salt, an analog, or a derivative thereof.

Examples of suitable ALDH agonists include Compounds 1-4, as shown below, or any of the compounds disclosed in WO 2008/122164

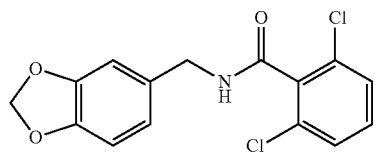

Compound 1

Compound 1: (N-(1,3-benzodioxol-5-ylmethyl)-2,6-dichlorobenzamide). Compound 1 is also referred to as Alda-1.

Compound 2 has the structure:

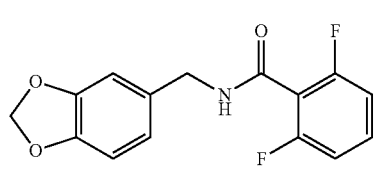

Compound 2

Compound 2: (N-(1,3-benzodioxol-5-ylmethyl)-2,6-difluorobenzamide)

Compound 3 has the structure:

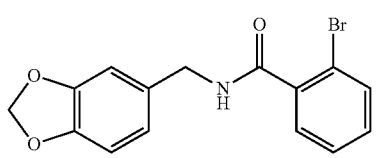

Compound 3

Compound 3: (N-(1,3-benzodioxol-5-ylmethyl)-2-bromobenzamide).

In some embodiments, one or more of Compound 1, Compound 2, and Compound 3 is specifically excluded.

Compound 4 has the structure:

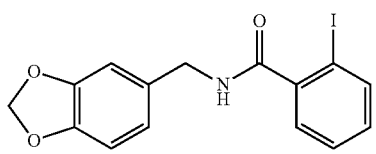

Compound 4

Compound 4: (N-(1,3-benzodioxol-5-ylmethyl)-2-iodobenzamide).

An additional example of an ALDH agonist is capsaicin. Capsaicin has the structure:

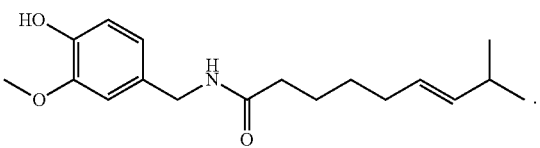 [SMILES: COc1cc(CNC(=O)CCCC/C=C/C(C)C)ccc1O]

Methods of Treating Chronic and Acute Free-Radical Associated Diseases

The present disclosure provides methods for treating acute and chronic free-radical associated diseases in an individual, the methods generally involving administering to an individual in need thereof an effective amount of a subject ALDH agonist.

Acute Free-Radical Associated Disorders

The present disclosure provides methods for treating acute free-radical associated diseases in an individual, the methods generally involving administering to an individual in need thereof an effective amount of a subject ALDH agonist. Acute free radical-associated disorders that are amenable to treatment with a subject method include seizures (Patel et al. (2001) *Journal of Neurochemistry* 79:1065-1069); skin damage resulting from UV exposure, and photodamage of skin (e.g., "sunburn") (Aldini et al. (2007) *Chem Res Toxicol.* 20(3):416-23); acute thermal skin burn injury (Pintaudi et al. (2000) *Free Radical Res.* 33(2):139-46); and tissue hyperoxia (e.g., hyperoxia-induced chronic lung disease; and bronchopulmonary dysplasia) (Xu et al. (2006) *Am J. Phsiol. Lung Cell. Mol. Physiol.* 291(5):L966-75).

The present disclosure provides methods for treating sunburn in an individual, the methods generally involving administering to an individual in need thereof an effective amount of a subject ALDH agonist. In some embodiments, a subject method for treating sunburn comprises topically applying a formulation comprising a subject ALDH agonist to an area of the skin affected by sunburn.

The present disclosure provides methods for treating a seizure in an individual, the methods generally involving administering to an individual in need thereof an effective amount of a subject ALDH agonist. In some embodiments, a subject ALDH agonist is administered after a seizure has occurred, e.g., within from about 1 minute to about 5 minutes, from about 5 minutes to about 15 minutes, from about 15 minutes to about 30 minutes, from about 30 minutes to about 1 hour, or from about 1 hour to about 4 hours following a seizure. In other embodiments, a subject ALDH agonist is administered prophylactically, e.g., a subject ALDH agonist is administered to an individual who has experienced a seizure in the past, to reduce the likelihood that another seizure will occur. In some embodiments, an effective amount of a subject ALDH agonist is an amount that is effective to reduce at least one of the severity of a seizure, the frequency of seizures, and the duration of a seizure.

Chronic Free-Radical Associated Diseases

The present disclosure provides methods for treating chronic free-radical associated diseases in an individual, the methods generally involving administering to an individual in need thereof an effective amount of a subject ALDH agonist. Chronic free radical-associated disorders that are amenable to treatment with a subject method include neurodegenerative diseases such as Parkinson's Disease and Alzheimer's Disease (Burke et al. (2003) *Neurol. Dis.* 2(2):143; and Ohta and Ohsawa (2006) *J. Alzheimer's Disease* 9(2):155); amyotrophic lateral sclerosis (ALS); cancer such as esophageal cancer (Chen et al. (2006) *Int J Cancer* 2119(12):2827-31); upper aerodigestive tract cancer (Hashibe et al. (2006) *Cancer Epidemiol Biomarkers Prev.* 15(4):696-703); head and neck squamous cell carcinoma (Hashimoto et al. (2006) *Tumour Biol.* 27(6):334-8; Yokoyama et al. (2005) *Alcohol.* 35(3):175-85); peripheral artery disease (see, e.g., Wenzel et al. (2008) *Cardiovasc. Res.* 80:280; and Pipinos et al. (2006) *Free Radical Biol. Med.* 41:262); cardiovascular diseases such as atherosclerosis (Narita et al. (2003) *Ultrasound in Medicine and Biology* 29(10):1415-1419); and the like. In some embodiments, a chronic free radical-associated disease is treated by chronic (e.g., daily) treatment with a subject ALDH agonist.

The present disclosure provides a method for treating Alzheimer's Disease (AD) in an individual suffering from AD, the method generally involving administering to the individual an effective amount of a subject ALDH agonist. In some embodiments, an "effective amount" of a subject ALDH agonist is an amount that is effective to at least slow the decline in cognitive function in the individual. In some embodiments, an "effective amount" of a subject ALDH agonist is an amount that is effective to improve memory in the individual being treated. In some embodiments, a subject ALDH agonist is administered to the individual systemically, over a period of time of from about 3 months to about 6 months, from about 6 months to about 1 year, or more than 1 year.

The present disclosure provides a method for treating Parkinson's Disease in an individual, the method generally involving administering to the individual an effective amount of a subject ALDH agonist. In some embodiments, an "effective amount" of a subject ALDH agonist is an amount that is effective to ameliorate one or more symptoms of Parkinson's Disease. In some embodiments, an "effective amount" of a subject ALDH agonist is an amount that is effective to slow the progress of the disease. In some embodiments, a subject ALDH agonist is administered to the individual systemically, over a period of time of from about 3 months to about 6 months, from about 6 months to about 1 year, or more than 1 year.

Methods of Treating Heart Conditions

The present disclosure provides methods of treating disorders such as angina, heart failure, insensitivity to nitroglycerin in angina and heart failure (Li et al. (2006) *J. Clin. Invest.* 116:506-511), hypertension (Asselin et al. (2006) *Free Radical Biol. and Med.* 41:97), and heart disease. The methods generally involve administering to an individual in need thereof an effective amount of a subject ALDH agonist.

In some embodiments, a subject ALDH agonist is administered to an individual in conjunction with nitroglycerin treatment. The subject ALDH agonist and the nitroglycerin can be administered by the same route of administration (e.g., oral, sublingual, transdermal, translingual, etc.). In the alternative, subject ALDH agonist and the nitroglycerin can be administered by different routes of administration. For example, in some embodiments, nitroglycerin is administered sublingually, translingually, transdermally, or orally; and a subject ALDH agonist is administered via a different route of administration (e.g., intravenous, intramuscular, etc.). The ALDH agonist can be administered before, during, or after administration of the nitroglycerin.

An effective amount of a subject ALDH agonist is an amount that, when administered in combination therapy with nitroglycerin, is effective to reduce angina by at least about 10%, at least about 20%, at least about 30%, at least about 40%, at least about 50%, at least about 60%, at least about 70%, at least about 80%, or at least about 90%, or more, within a period of time of from about 1 minute to about 2 minutes, from about 2 minutes to about 3 minutes, from about 3 minutes to about 4 minutes, from about 4 minutes to about 5 minutes, or from about 5 minutes to about 10 minutes, following administration of the ALDH agonist. In some embodiments, a subject ALDH agonist and nitroglycerin are administered substantially simultaneously, e.g., within about two minutes, within about 1 minute, or within about 30 seconds of one another. The term "combination therapy with nitroglycerin" encompasses administration of a subject ALDH agonist substantially simultaneously with nitroglycerin; administration of a subject ALDH agonist before administration of nitroglycerin; administration of a subject ALDH agonist after administration of nitroglycerin; etc.

In some embodiments, an effective amount of a subject ALDH agonist is an amount that is effective to treat hypertension, e.g., to reduce one or more symptoms or indications of hypertension in an individual. For example, in some embodiments, an effective amount of a subject ALDH agonist is an amount that is effective to reduce blood pressure in the individual by at least about 5%, at least about 10%, at least about 15%, at least about 20%, or at least about 25%, or more, or to bring the blood pressure of the individual to within a normal range.

In some embodiments, an effective amount of a subject ALDH agonist is an amount that is effective to treat heart disease, e.g., to reduce one or more symptoms or indications of heart disease in an individual. Whether a given ALDH agonist is effective to treat heart disease can be determined using standard methods of assessing heart function, e.g., electrocardiogram, angiogram, and the like.

Methods of Detoxification

The present disclosure provides methods of reducing the levels of a toxic compound in an individual, the methods generally involving administering to an individual in need thereof an effective amount of a subject ALDH agonist. The present disclosure provides methods of treating a disorder associated with or resulting from a toxic level of a compound (e.g., a xenogenic aldehyde; a biogenic aldehyde; or a compound that, when ingested, absorbed, or inhaled, gives rise to an aldehyde substrate for ALDH), the methods generally involving administering to an individual in need thereof an effective amount of a subject ALDH agonist, where the level of the compound in the individual is reduced to a non-toxic level.

Toxic compounds whose levels can be reduced in an individual using a subject method include, but are not limited to, ethanol, methanol, ethylene glycol monomethyl ether, xenogenic aldehydes, biogenic aldehydes, and an aldehyde produced by in vivo metabolism of a compound that is ingested, absorbed, or inhaled. A subject ALDH agonist is administered in an amount that is effective, when administered in one or more doses, to reduce a toxic level of a compound such as ethanol, methanol, ethylene glycol monomethyl ether, xenogenic aldehydes, biogenic aldehydes, or an aldehyde produced by in vivo metabolism of a compound that is ingested, absorbed, or inhaled. In some embodiments, the aldehyde is acetaldehyde.

As an example, a subject ALDH agonist is administered to an individual following excessive alcohol (e.g., ethanol) consumption; and toxic levels of alcohol or aldehyde (e.g., an aldehyde that is a metabolic product of ethanol) in the individual are reduced by at least about 10%, at least about 20%, at least about 30%, at least about 40%, at least about 50%, at least about 60%, at least about 70%, at least about 80%, or at least about 90%, or more, compared to the alcohol or aldehyde levels in the individual before treatment with the ALDH agonist. In some embodiments, a subject ALDH agonist is administered in an amount that is effective to reduce a toxic alcohol or aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic alcohol or aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

As an example, a subject ALDH agonist is administered to an individual following excessive alcohol (e.g., ethanol) consumption; and levels of acetaldehyde in the individual are reduced by at least about 10%, at least about 20%, at least about 30%, at least about 40%, at least about 50%, at least about 60%, at least about 70%, at least about 80%, or at least about 90%, or more, compared to the alcohol or aldehyde levels in the individual before treatment with the ALDH agonist. In some embodiments, a subject ALDH agonist is administered in an amount that is effective to reduce an acetaldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

The present disclosure provides methods of reducing aldehyde toxicity, the methods generally involving administering an effective amount of a subject ALDH agonist. In some embodiments, an effective amount of an ALDH agonist is an amount that is effective to reduce one or more symptoms of aldehyde toxicity. For example, in some embodiments, an effective amount of an ALDH agonist is an amount that is effective to reduce one or more symptoms of excess ethanol consumption, where such symptoms include, e.g., headache, dehydration, fatigue, nausea, vomiting, diarrhea, weakness, anxiety, irritability, photophobia, phonophobia, etc.

As an example, a subject ALDH agonist is administered to an individual having a toxic level of an aldehyde (e.g., following excessive ethanol consumption); and toxic levels of an aldehyde in the individual are reduced by at least about 10%, at least about 20%, at least about 30%, at least about 40%, at least about 50%, at least about 60%, at least about 70%, at least about 80%, or at least about 90%, or more, compared to the level of the aldehyde in the individual before treatment with the ALDH agonist. In some embodiments, a subject ALDH agonist is administered in an amount that is effective to reduce a toxic aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

In some embodiments, a subject ALDH agonist reduces the level of both ethanol and an aldehyde, e.g., following excessive ethanol consumption, as described above.

As another example, a subject ALDH agonist is administered to an individual having toxic levels of methanol or ethylene glycol monomethyl ether; and the toxic level of methanol or ethylene glycol monomethyl ether is reduced by at least about 10%, at least about 20%, at least about 30%, at least about 40%, at least about 50%, at least about 60%, at least about 70%, at least about 80%, or at least about 90%, or more, compared to the methanol or ethylene glycol monomethyl ether level in the individual before treatment with the ALDH agonist. In some embodiments, a subject ALDH agonist is administered in an amount that is effective to reduce a toxic methanol or ethylene glycol monomethyl ether level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic methanol or ethylene glycol monomethyl ether level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

As another example, a subject ALDH agonist is administered to an individual exhibiting drug toxicity, e.g., a toxic level of an aldehyde following ingestion, absorption, or inhalation of a drug (e.g., a pharmaceutical compound, an illicit drug, etc.). In some embodiments, the aldehyde is produced following ingestion, absorption, or inhalation of a drug, by metabolism of the drug in the body. The toxic level of aldehyde is reduced by at least about 10%, at least about 20%, at least about 30%, at least about 40%, at least about 50%, at least about 60%, at least about 70%, at least about 80%, or at least about 90%, or more, compared to the level of the aldehyde in the individual before treatment with the ALDH agonist. In some embodiments, a subject ALDH agonist is administered in an amount that is effective to reduce a toxic aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some embodiments, a subject ALDH agonist is administered in an amount that is effective to reduce a toxic aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist.

Methods of Reducing Salsolinol Levels

The present disclosure provides methods of reducing salsolinol levels in an individual, the methods generally involving administering to the individual an effective amount of a subject ALDH agonist. Salsolinol (1-methyl-6,7-dihydroxy-1,2,3,4-tetrahydroisoquionoline) is a condensation product of dopamine with acetaldehyde. Acetaldehyde is a metabolic product of ethanol. Plasma salsolinol levels are higher in alcoholic compared to non-alcoholics. Reduction of salsolinol levels is useful in reducing alcohol addiction.

In some embodiments, an effective amount of a subject ALDH agonist is administered to an individual in need thereof following excessive alcohol (e.g., ethanol) consumption; where the effective amount provides for a reduction in the levels of salsolinol in the individual of at least about 10%, at least about 20%, at least about 30%, at least about 40%, at least about 50%, at least about 60%, at least about 70%, at least about 80%, or at least about 90%, or more, compared to the salsolinol levels in the individual before treatment with the ALDH agonist. In some embodiments, an effective amount of a subject ALDH agonist is administered to an individual in need thereof at any time (e.g., not necessarily following excessive alcohol consumption). In some embodiments, a subject ALDH agonist is administered in an amount that is effective to reduce a salsolinol level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH agonist. In some of these embodiments, the individual is one who has been diagnosed with alcoholism. Symptoms and diagnosis of alcoholism are described in, e.g., Enoch and Goldman (2002) *American Family Physician* 65:441.

Methods of Treating Diabetes

The present disclosure provides methods of treating diabetes, the methods generally involving administering to an individual in need thereof an effective amount of a subject ALDH agonist. In some embodiments, a subject method of treating diabetes provides for treatment of a disorder that is a result of diabetes, e.g., diabetic nephropathy, diabetic neuropathy, and the like.

In some embodiments, a subject ALDH agonist is administered in an amount that is effective to reduce a blood glucose level in an individual, e.g., to reduce a blood glucose level in an individual by at least about 10%, at least about 15%, at least about 20%, at least about 25%, at least about 30%, at least about 40%, or at least about 50% when compared to the blood glucose levels in the absence of treatment with the agonist. In some embodiments, an effective amount of an ALDH agonist is an amount that is effective to reduce blood glucose levels to a normal range. Normal fasting blood glucose levels are typically in the range of from about 70 mg/dL to about 110 mg/dL before a meal. Normal blood glucose levels 2 hours after a meal are usually less than about 120 mg/dL. Normal blood glucose levels during an oral glucose tolerance test (involving drinking a sugar solution containing about 75 g glucose; then measuring blood glucose levels at various times following drinking the sugar solution) include: less than 140 mg/dL 2 hours after drinking the sugar solution; and all readings between 0 and 2 hours after drinking the sugar solution less than 200 mg/dL. Blood glucose levels are also sometimes expressed in mmol/L. Normal blood glucose levels are generally between about 4 mmol/L and 8 mmol/L. Normal blood glucose levels are generally less than about 10 mmol/L 90 minutes after a meal; and from about 4 mmol/L to about 7 mmol/L before meals.

In some embodiments, a subject treatment method comprises administering a subject ALDH agonist, and co-administering at least a second therapeutic agent (e.g., insulin) for the treatment of diabetes. Insulin that is suitable for use herein includes, but is not limited to, regular insulin, semilente, NPH, lente, protamine zinc insulin (PZI), ultralente, insuline glargine, insulin aspart, acylated insulin, monomeric insulin, superactive insulin, hepatoselective insulin, and any other insulin analog or derivative, and mixtures of any of the foregoing. Insulin that is suitable for use herein includes, but is not limited to, the insulin forms disclosed in U.S. Pat. Nos. 4,992,417; 4,992,418; 5,474,978; 5,514,646; 5,504,188; 5,547,929; 5,650,486; 5,693,609; 5,700,662; 5,747,642; 5,922,675; 5,952,297; and 6,034,054; and published PCT applications WO 00/121197; WO 09/010,645; and WO 90/12814. Insulin analogs include, but are not limited to, superactive insulin analogs, monomeric insulins, and hepatospecific insulin analogs.

Methods of Treating Osteoporosis

The present disclosure provides methods of treating osteoporosis, the methods generally involving administering to an individual in need thereof an effective amount of a subject ALDH agonist. In some embodiments, an "effective amount" of an ALDH agonist is an amount effective to increase bone density in the individual. In other embodiments, an "effective amount" of an ALDH agonist is an amount that is effective to reduce the rate of bone density loss.

Methods of Treating Head and Neck Cancer

The present disclosure provides methods of treating head and neck cancers, e.g., cancer that occurs or arises in the head or neck region (e.g., as a result of accumulation of toxic aldehydes or reduced ALDH activity), e.g., cancers that occur in the nasal cavity, in the sinuses, on the lips, in the mouth, in the salivary glands, in the throat, or in the larynx. The methods generally involve administering to an individual in need thereof an effective amount of an ALDH agonist, e.g., an ALDH1 agonist, an ALDH2 agonist, or an ALDH3 agonist, or a combination of two or more of ALDH1 agonist, an ALDH2 agonist, and an ALDH3 agonist. In some embodiments, the ALDH agonist is a subject ALDH agonist. In other embodiments, the ALDH agonist is an ALDH agonist as disclosed in WO 2008/122164.

In some embodiments, a subject method involves administering to an individual who is at risk of developing a head and neck cancer an effective amount of an ALDH agonist, where an effective amount of an ALDH agonist is an amount that is effective to reduce the risk that the individual will develop a head and neck cancer. For example, individuals who are habitual users of betel quid (e.g., individuals who habitually chew betel quid). Betel quid is a combination of betel leaves and *areca* nut. Sometimes tobacco is combined with betel quid. Betel quid (sometimes in combination with tobacco) is chewed; habitual, long-term use of betel quid is associated with high risk of oral and esophageal squamous cell carcinoma.

In some embodiments, a subject method involves administering to an individual, which individual is at greater risk than the general population of developing an oral or esophageal squamous cell carcinoma (head and neck cancer) due to habitual use of betel quid, an effective amount of an ALDH agonist, where the ALDH agonist is administered systemically or locally. Local administration to the oral cavity can be accomplished by administering an ALDH agonist that is in an oral formulation, e.g., a mouth rinse, toothpaste, lozenge, chewing gum, tooth gel, tooth powder, and the like, as described above. In some embodiments, an effective amount of an ALDH agonist is an amount that, when administered in one or more doses, is effective to reduce the risk that the individual will develop head and neck cancer, e.g., is effective to reduce the risk by at least about 10%, at least about 15%, at least about 20%, at least about 25%, at least about 30%, at least about 40%, at least about 50%, at least about 60%, at least about 70%, at least about 80%, or more than 80%, compared to the risk in the individual not treated with the ALDH agonist.

In some embodiments, an ALDH agonist is administered to an individual who has head and neck cancer. In some embodiments, an ALDH agonist is administered alone, e.g., in monotherapy without co-administration of any other anti-cancer agent. In other embodiments, an ALDH agonist is administered in conjunction with a standard cancer treatment (e.g., chemotherapy, radiation therapy, surgery, or a combination thereof). For example, laryngeal cancer can be treated by administration of an ALDH agonist in combination with: 1) radiation therapy; 2) surgery (e.g., laser excision surgery); 3) cisplatin/5-FU combination therapy, followed by radiation therapy; or 4) radiation therapy and cisplatin treatment. As another non-limiting example, oral cavity cancer can be treated by administration of an ALDH agonist in combination with: 1) surgery; 2) radiation therapy (e.g., external beam radiation therapy or interstitial implantation radiation therapy); or 3) a combination of surgery and radiation therapy.

A subject method is effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, an "effective amount" of a subject ALDH agonist is an amount that, when administered in conjunction with a standard cancer therapy, is effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen); computed tomography scanning, magnetic resonance imaging, and/or x-ray imaging of the tumor to estimate and/or monitor tumor size; measuring the amount of tumor-associated antigen in a biological sample (e.g., blood, serum, plasma, etc.); and the like.

Combination Therapy for the Treatment of Cancer

The present disclosure provides methods for treating cancer, e.g., where an ALDH agonist is suitable for sensitizing a cancerous cell to a cancer chemotherapeutic agent or other standard cancer therapy such as radiation therapy. In some embodiments, the ALDH agonist is a subject ALDH agonist. In other embodiments, the ALDH agonist is an ALDH agonist as disclosed in WO 2008/122164.

In some embodiments, a subject method provides for a reduction in the amount of a chemotherapeutic agent or a dose of ionizing radiation required to reduce the number of cancer cells and/or reduce the tumor mass in an individual. Thus, e.g., in some embodiments, the present disclosure provides a method of treating cancer in an individual who has a cancer, the method generally involving administering: a) an ALDH agonist; and b) a cancer chemotherapeutic agent, where the ALDH agonist and the cancer chemotherapeutic agent are administered in combined effective amounts that are effective to reduce the number of tumor cells and/or tumor mass in the individual by at least about 10%, at least about 20%, at least about 30%, at least about 40%, at least about 50%, at least about 60%, at least about 70%, at least about 80%, at least about 90%, or more than 90%, where the dose of the cancer chemotherapeutic agent is at least about 5%, at least about 10%, at least about 15%, at least about 20%, at least about 25%, or more than 25%, lower than the dose of the chemotherapeutic agent required to provide for the same reduction in the number of cancer cells or the tumor mass when administered in monotherapy (without co-administration of the ALDH agonist).

In some embodiments, the present disclosure provides a method of treating cancer in an individual who has a cancer, the method generally involving administering: a) an ALDH agonist; and b) ionizing radiation, where the ALDH agonist and the ionizing radiation are administered in combined effective amounts that are effective to reduce the number of tumor cells and/or tumor mass in the individual by at least about 10%, at least about 20%, at least about 30%, at least about 40%, at least about 50%, at least about 60%, at least about 70%, at least about 80%, at least about 90%, or more than 90%, where the dose of the ionizing radiation is at least about 5%, at least about 10%, at least about 15%, at least about 20%, at least about 25%, or more than 25%, lower than the dose of the ionizing radiation required to provide for the same reduction in the number of cancer cells or the tumor mass when administered in monotherapy (without co-administration of the ALDH agonist).

Radiation therapy includes, but is not limited to, x-rays or gamma rays that are delivered from either an externally applied source such as a beam, or by implantation of small radioactive sources. For example, radiation therapy includes external beam radiation therapy and brachytherapy.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indoledione, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore, compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2)

inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; (9) inhibitors of angiogenesis; and (10) antagonists of tumor necrosis factor.

Methods of Treating Cigarette Smoke-Induced Lung Cancer

The present disclosure provides methods for treating cigarette smoke-induced lung cancer, e.g., lung cancer that results from prolonged exposure (either direct or second-hand) to cigarette smoke.

At least six toxicants present in cigarette smoke are of particular concern as health risks: acrolein, acetaldehyde, acrylonitrile, benzene, 1,3-butadiene, and formaldehyde. Acrolein has a high hazard index and causes oxidative stress by reacting with sulfhydryl groups. Acrolein is more toxic (10-1000 times) than formaldehyde, acetaldehyde, and 4-hydroxynonenal and can reach 80 microM in the respiratory tract fluid in smokers. (See, e.g.: 1. Liu et. al. Journal of Neurochemistry, 2007, 103, 2690-2700. 2. Esterbauer H, Schaur R J, Zollner H. Chemistry and biochemistry of 4-hydroxynonenal, malonaldehyde and related aldehydes. *Free Radic Biol Med.* 1991; 11:81-128. 3. Nguyen E, Picklo M J Sr. Inhibition of succinic semialdehyde dehydrogenase activity by alkenal products of lipid peroxidation. *Biochim Biophys Acta.* 2003; 1637:107-112. 4. Eiserich J P, van der Vliet A, Handelman G J, Halliwell B, Cross C E. Dietary antioxidants and cigarette smoke-induced biomolecular damage: a complex interaction. *Am J Clin Nutr.* 1995; 62(suppl 6):14905-15005.).

As subject method of treating cigarette smoke-induced lung cancer generally involves administering to an individual in need thereof an effective amount of an ALDH agonist. In some embodiments, the ALDH agonist is a subject ALDH agonist. In other embodiments, the ALDH agonist is an ALDH agonist as disclosed in WO 2008/122164.

A subject method of treating cigarette smoke-induced lung cancer is effective to reduce lung cancer tumor laod by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, an "effective amount" of a subject ALDH agonist is an amount that, is effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen); computed tomography scanning, magnetic resonance imaging, and/or x-ray imaging of the tumor to estimate and/or monitor tumor size; measuring the amount of tumor-associated antigen in a biological sample (e.g., blood, serum, plasma, etc.); and the like.

In some embodiments, an ALDH agonist is administered as monotherapy. In other embodiments, an ALDH agonist is administered in combination with one or more of: 1) a standard cancer chemotherapy agent; 2) radiation treatment for the lung cancer; and 3) surgical treatment for the cancer (e.g., surgical removal of cancerous tissue from the lung).

Subjects Suitable for Treatment

Subjects suitable for treatment with a subject ALDH agonist include individuals suffering from a condition described above; individuals at risk for developing a condition described above; individuals who have been treated for a condition described above with an agent other than a subject ALDH agonist, and who either failed to respond to such treatment, or who initially responded to such treatment, but subsequently relapsed; individuals who are refractory to treatment with an agent other than a subject ALDH agonist for a condition described above; and individuals who cannot tolerate treatment with an agent other than a subject ALDH agonist for a condition described above. Subjects suitable for treatment with a subject ALDH agonist include individuals who have been diagnosed as having a condition described below.

Methods Involving Administering an ALDH Agonist

A subject treatment method involving administration of a subject ALDH agonist is suitable for treating various conditions, as noted above, including disorders or conditions associated with or resulting from oxidative stress; disorders or conditions associated with nitroglycerin insensitivity; disorders or conditions associated with toxic levels of ethyl alcohol, aldehyde, methanol, ethylene glycol monomethyl ether, biogenic or xenogenic aldehydes, etc.; and heart diseases and conditions, such as coronary artery disease, angina, etc. In some embodiments, the individual is a human who is homozygous for an ALDH2 allele that encodes an ALDH2 having an amino acid sequence as depicted in FIG. 5A. In other embodiments, the individual is a human who carries one or two ALDH2*2 alleles, where an ALDH2*2 allele encodes an ALDH2 having the E487K variant as depicted in FIG. 5B.

Approximately 40% of the East Asian population carries the semidominant ALDH2*2 allele. Such individuals can be characterized by a response to ethanol consumption that includes one or more of facial flushing, nausea, and tachycardia. In addition, ALDH2*2 individuals are also less responsive to nitroglycerin treatment for such disorders as angina and coronary artery disease. Individuals who are heterozygous or homozygous for the ALDH2*2 allele are suitable for treatment with a subject method involving administration of a subject ALDH agonist.

Methods of Treating Conditions Associated with Ischemic Stress

Subjects suitable for treatment with subject ALDH agonist include individuals who are scheduled to undergo cardiac surgery or who have undergone cardiac surgery; individuals who have experienced a stroke; individuals who have suffered brain trauma; individuals who have prolonged surgery; individuals who have suffered a myocardial infarct (e.g., acute myocardial infarction), individuals who are about to undergo scheduled cardiac by-pass surgery; individuals who suffer from cerebrovascular disease; individuals who have spinal cord injury; individuals having a subarachnoid hemorrhage; and individuals who will be subjected to organ transplantation. Subjects suitable for treatment with a subject ALDH agonist also include individuals having an ischemic limb disorder, e.g., resulting from Type 1 or Type 2 diabetes.

Methods of Treating Ocular Disorders

Subjects suitable for treatment with an ALDH agonist (e.g., a subject ALDH agonist) include individuals who have an ocular disorder. Ocular disorders include, e.g., age-related cataracts, secondary cataracts, traumatic cataracts, congenital cataracts, age-related macular degeneration, radiation cataracts, etc.

Methods of Treating Skin Disorders.

Subjects suitable for treatment with an ALDH agonist (e.g., a subject ALDH agonist) include individuals who have a skin disorder. Skin disorders include, e.g., radiation dermatitis, atopic dermatitis, sunburn, ultraviolet radiation damage to the skin, skin aging, and premature hair loss.

Methods of Treating Radiation-induced Damage to Epithelial Cells

Subjects suitable for treatment with an ALDH agonist include individuals who have been exposed to ionizing radiation, either accidentally or by a medical treatment such as cancer radiotherapy.

Methods of Treating Acute Free-radical Associated Diseases

Subjects suitable for treatment with a subject ALDH agonist include individuals who are having or who have experienced a seizure; individuals having skin damage resulting from UV exposure; individuals having photodamage of the skin; individuals having an acute thermal skin burn injury; and individuals suffering from tissue hyperoxia.

Methods of Treating Chronic Free-radical Associated Diseases

Subjects suitable for treatment with subject ALDH agonist include individuals who have been diagnosed with Alzheimer's disease, Parkinson's disease, amyotrophic lateral sclerosis, or other neurodegenerative disease; individuals having atherosclerosis; individuals having esophageal cancer; individuals having head and neck squamous cell carcinoma; and individuals having upper aerodigestive tract cancer.

Methods of Treating Cardiac Conditions

Subjects suitable for treatment with a subject ALDH agonist include individuals having angina; individuals having heart failure; individuals who exhibit an insensitivity to nitroglycerin in the treatment of angina or heart failure; individuals having hypertension; and individuals having heart disease.

Detoxification Methods

Subjects suitable for treatment with a subject ALDH agonist include individuals who have toxic levels of an aldehyde, e.g., via ingestion of a toxic compound, via inhalation of a toxic compound, via ingestion or inhalation of toxic levels of a compound, or via production of the aldehyde during normal metabolism. Such individuals include, but are not limited to, individuals who have ingested or inhaled ethanol, methanol, ethylene glycol monomethyl ether, or other xenogenic or biogenic aldehyde compounds or compounds that give rise to biogenic aldehydes. For example, such individuals include individuals who have ingested or inhaled pesticides, fungicides, or other such compounds; individuals who have consumed excessive levels of ethanol; and the like.

Methods of Treating Diabetes

Subjects suitable for treatment with a subject ALDH agonist include individuals having Type 1 or Type 2 diabetes. Subjects suitable for treatment include individuals who have been diagnosed with Type 1 diabetes mellitus, where such individuals include those having a fasting blood glucose level greater than about 126 mg/dL. Such individuals include those having blood glucose levels of greater than about 200 mg/dL following a two-hour glucose tolerance test (75 g anhydrous glucose orally). Subjects suitable for treatment include individuals who have been diagnosed with Type 2 diabetes; individuals who have not yet been diagnosed with Type 2 diabetes, but who are at risk of developing Type 2 diabetes, e.g., individuals having a body mass index (weight in kilograms divided by height (in meters) squared) greater than 25, e.g., individuals having a body mass index from about 25 to about 27, from about 27 to about 30, or greater than 30.

Methods of Treating Cancer

Subjects suitable for treatment with an ALDH agonist in combination with a cancer chemotherapeutic agent and/or ionizing radiation include individuals having a cancer. The methods are useful for treating a wide variety of cancers, including carcinomas, sarcomas, leukemias, and lymphomas. Thus, the individual can have a cancer such as a carcinoma, a sarcoma, a leukemia, or a lymphoma. In some embodiments, the individual has lung cancer resulting from prolonged exposure to cigarette smoke.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; and the like.

Variant ALDH

The present disclosure provides variant ALDH polypeptides. A subject variant ALDH polypeptide comprises a glutamic acid-to-lysine (E→K) change at a position equivalent to E487K of ALDH2 (e.g., E501 of the ALDH2 amino acid sequence depicted in FIG. 5A, which is E487 of mature ALDH2 (without the MLRAAARFGPRLGRRLL peptide shown in bold in FIG. 5A). The E→K substitution reduces enzymatic activity of an ALDH polypeptide. A subject variant ALDH polypeptide is useful for identifying agents that increase enzymatic activity of an ALDH polypeptide. Thus, the present disclosure also provides methods of using the polypeptides in screening methods for identification of agents that increase enzymatic activity of ALDH.

A subject variant ALDH polypeptide can be produced recombinantly, e.g., by synthesizing a nucleic acid comprising a nucleotide sequence encoding a subject variant ALDH polypeptide, and expressing the nucleic acid in a suitable host cell. Thus, in some embodiments, a subject variant ALDH polypeptide is recombinant. A subject variant ALDH polypeptide can be isolated from other, non-ALDH, polypeptides or other macromolecules, and in some embodiments will be purified, e.g., will be at least about 70%, at least about 75%, at least about 80%, at least about 85%, at least about 90%, at least about 95%, at least about 98%, at least about 99%, or greater than 99%, pure.

A subject variant ALDH polypeptide exhibits reduced enzymatic activity compared to a wild-type ALDH polypeptide. For example, a subject variant ALDH polypeptide exhibits enzymatic activity that is less than about 80%, less than about 70%, less than about 60%, less than about 50%, less than about 40%, less than about 30%, or less than about 25%, of the enzymatic activity of the corresponding wild-type ALDH polypeptide.

As an example, in some embodiments, a subject variant ALDH polypeptide comprises at least an E488K substitution compared to the amino acid sequence set forth in FIG. 6A or FIG. 6B, and exhibits enzymatic activity that is less than about 80%, less than about 70%, less than about 60%, less than about 50%, less than about 40%, less than about 30%, or less than about 25%, of the enzymatic activity of an ALDH1 polypeptide comprising the amino acid sequence set forth in FIG. 6A or FIG. 6B.

As another example, in some embodiments, a subject variant ALDH polypeptide comprises at least an E447K substitution compared to the amino acid sequence set forth in FIG. 7, and exhibits enzymatic activity that is less than about 80%, less than about 70%, less than about 60%, less than about 50%, less than about 40%, less than about 30%, or less than about 25%, of the enzymatic activity of an ALDH3 polypeptide comprising the amino acid sequence set forth in FIG. 7.

As another example, in some embodiments, a subject variant ALDH polypeptide comprises at least an E523K substitution compared to the amino acid sequence set forth in FIG. 12, and exhibits enzymatic activity that is less than about 80%, less than about 70%, less than about 60%, less than about 50%, less than about 40%, less than about 30%, or less than about 25%, of the enzymatic activity of an ALDH5 polypeptide comprising the amino acid sequence set forth in FIG. 12.

In some embodiments, a subject variant ALDH polypeptide comprises at least an E488K substitution compared to the amino acid sequence set forth in FIG. 6A or FIG. 6B, and comprises an amino acid sequence having at least about 75%, at least about 80%, at least about 85%, at least about 90%, at least about 95%, at least about 98%, or at least about 99%, amino acid sequence identity to a contiguous stretch of from about 400 aa to about 450 aa, or from about 450 aa to about 501 aa, of the amino acid sequence set forth in FIG. 6A or 6B. In some embodiments, a subject variant ALDH polypeptide comprises the amino acid sequence set forth in FIG. 6A or FIG. 6B, and comprises an E488K substitution compared to the amino acid sequence set forth in FIG. 6A or FIG. 6B.

In some embodiments, a subject variant ALDH polypeptide comprises at least an E447K substitution compared to the amino acid sequence set forth in FIG. 7, and comprises an amino acid sequence having at least about 75%, at least about 80%, at least about 85%, at least about 90%, at least about 95%, at least about 98%, or at least about 99%, amino acid sequence identity to a contiguous stretch of from about 350 aa to about 400 aa, or from about 400 aa to about 453 aa, of the amino acid sequence set forth in FIG. 7. In some embodiments, a subject variant ALDH polypeptide comprises the amino acid sequence set forth in FIG. 7, and comprises an E447K substitution compared to the amino acid sequence set forth in FIG. 7.

In some embodiments, a subject variant ALDH polypeptide comprises at least an E523K substitution compared to the amino acid sequence set forth in FIG. 12, and comprises an amino acid sequence having at least about 75%, at least about 80%, at least about 85%, at least about 90%, at least about 95%, at least about 98%, or at least about 99%, amino acid sequence identity to a contiguous stretch of from about 400 aa to about 450 aa, from about 450 aa to about 500 aa, or from about 500 aa to about 535 aa, of the amino acid sequence set forth in FIG. 12. In some embodiments, a subject variant ALDH polypeptide comprises the amino acid sequence set forth in FIG. 12, and comprises an E523K substitution compared to the amino acid sequence set forth in FIG. 12.

In some embodiments, a subject variant ALDH is a fusion polypeptide, e.g., a polypeptide comprising a subject variant ALDH fused in-frame with a fusion partner, where a fusion partner is a polypeptide other than ALDH. In some embodiments, the fusion partner is attached to the amino terminus of a subject variant ALDH polypeptide. In other embodiments, the fusion partner is attached to the carboxyl terminus of a subject variant ALDH polypeptide. In other embodiments, the fusion partner is fused in-frame to a subject variant ALDH polypeptide at a location internal to the variant ALDH polypeptide. Suitable fusion partners include immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; polypeptides that facilitate purification or isolation of the fusion protein, e.g., metal ion binding polypeptides such as 6His tags (e.g., variant ALDH/6His), glutathione-S-transferase, and the like; polypeptides that provide for subcellular localization; and polypeptides that provide for secretion from a cell.

In some embodiments, the fusion partner is an epitope tag. In some embodiments, the fusion partner is a metal chelating peptide. In some embodiments, the metal chelating peptide is a histidine multimer, e.g., $(His)_6$. In some embodiments, a $(His)_6$ multimer is fused to the amino terminus of the variant ALDH; in other embodiments, a $(His)_6$ multimer is fused to the carboxyl terminus of the variant ALDH. The $(His)_6$-variant ALDH fusion protein is purified using any of a variety of available nickel affinity columns (e.g. His-bind resin, Novagen).

Compositions

The present disclosure provides a composition comprising a subject variant ALDH polypeptide. Compositions comprising a subject variant ALDH polypeptide can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES),2-(N-Morpholino) ethanesulfonic acid (MES),2-(N-Morpholino)ethanesulfonic acid sodium salt (MES),3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Nucleic Acids

The present disclosure further provides a nucleic acid comprising a nucleotide sequence encoding a subject variant ALDH polypeptide. A nucleic acid comprising a nucleotide sequence encoding a subject variant ALDH polypeptide is referred to herein as a "variant ALDH nucleic acid."

A subject variant ALDH nucleic acid is in some embodiments an expression vector. In some embodiments, the expression vector is suitable for expression in a prokaryotic host cell. In other embodiments, the expression vector is suitable for expression in a eukaryotic host cell.

The expression vector will provide a transcriptional and translational initiation region, which may be inducible or constitutive, where the coding region is operably linked under the transcriptional control of the transcriptional initiation region, and a transcriptional and translational termination region. Thus, e.g., a subject variant ALDH polynucleotide can comprise a nucleotide sequence encoding a subject variant ALDH polypeptide, where the variant ALDH polypeptide-encoding nucleotide sequence is operably linked to a transcriptional control element (e.g., a promoter), where the transcriptional control element can be inducible or constitutive.

Expression vectors generally have convenient restriction sites located near the promoter sequence to provide for the insertion of nucleic acid sequences encoding heterologous proteins (e.g., to provide for insertion of a nucleotide sequence encoding a subject variant ALDH polypeptide). A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol V is Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol V is Sci 38:2857 2863, 1997; Jomary et al., Gene Ther 4:683 690, 1997, Rolling et al., Hum Gene Ther 10:641648, 1999; Ali et al., Hum Mol Genet. 5:591594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as E. coli and yeast). The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). Mol. Microbiol. 22:367-378); a tet promoter (see, e.g., Hillen, W. and Wissmann, A. (1989) In Saenger, W. and Heinemann, U. (eds), *Topics in Molecular and Structural Biology, Protein— Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.).

Non-limiting examples of suitable eukaryotic promoters (promoters functional in a eukaryotic cell) include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

A subject recombinant vector will in some embodiments include one or more selectable markers. In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

Host Cells

The present disclosure further provides a genetically modified host cell comprising a subject variant ALDH nucleic acid, e.g., a subject variant ALDH expression vector. Suitable host cells include as unicellular microorganisms, as well as cells of multicellular organisms grown in in vitro culture as unicellular entities. Suitable host cells include bacterial cells such as *Escherichia coli*; yeast cells such as *Saccharomyces cerevisiae, Pichia pastoris, Hansenula polymorpha, Kluyveromyces lactis, Yarrowia lipolytica, Candida utilis, Schizosaccharomyces pombe*, and the like; insect cells such as *Drosophila melanogaster* cells; amphibian cells such as *Xenopus* cells; mammalian cells, such as CHO cells, 3T3 cells, and the like.

Screening Methods

The present disclosure provides methods for identifying an ALDH agonist. The methods generally involve contacting a subject variant ALDH enzyme having reduced enzymatic activity with a test compound, in the presence of a substrate for the variant ALDH enzyme; and determining the effect, if any, of the test compound on the enzymatic activity of the variant ALDH enzyme. An agent that increases the enzymatic activity of a subject variant ALDH polypeptide is a candidate agent for increasing the activity of a wild-type ALDH polypeptide.

As used herein, the term "determining" refers to both quantitative and qualitative determinations and as such, the term "determining" is used interchangeably herein with "assaying," "measuring," and the like.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising a subject variant ALDH enzyme and substrate in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

A test compound of interest is a compound that increases the enzymatic activity of a subject variant ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the variant ALDH polypeptide in the absence of the test compound.

In some embodiments, a test compound of interest has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

A candidate agent is assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

In many embodiments, the screening method is carried out in vitro, in a cell-free assay.

In some embodiments, the in vitro cell-free assay will employ a purified variant ALDH, where "purified" refers to free of contaminants or any other undesired components. Purified variant ALDH that is suitable for a subject screening method is at least about 50% pure, at least about 60% pure, at least about 70% pure, at least about 75% pure, at least about 80% pure, at least about 85% pure, at least about 90% pure, at least about 95% pure, at least about 98% pure, at least about 99% pure, or greater than 99% pure.

Purified variant ALDH will in some embodiments be stabilized by addition of one or more stabilizing agents, to maintain enzymatic activity. In some embodiments, a solution of purified variant ALDH comprises an aqueous solution of variant ALDH and from about 10% to about 50% glycerol, e.g., from about 10% to about 15%, from about 15% to about 20%, from about 20% to about 25%, from about 25% to about 30%, from about 30% to about 35%, from about 35% to about 40%, from about 40% to about 45%, or from about 45% to about 50% glycerol. In some embodiments, a solution of variant ALDH further comprises one or more of a chelating agent (e.g., EDTA or EGTA); salts such as NaCl, $MgCl_2$, KCl, and the like; buffers, such as a Tris buffer, phosphate-buffered saline, sodium pyrophosphate buffer, and the like; one or more protease inhibitors; and the like.

In some embodiments, a subject screening method is an in vitro cell-free assay. In some embodiments, a subject variant ALDH polypeptide used in a subject screening method is a recombinant variant ALDH. In some embodiments, a subject variant ALDH polypeptide used in a subject screening method is a variant ALDH fusion polypeptide.

Assays for ALDH enzymatic activity are known in the art, and any known assay can be used in a subject screening method. Examples of assays are found in various publications, including, e.g., Sheikh et al. ((1997) *J. Biol. Chem.* 272:18817-18822) and Farres et al. ((1994) *J. Biol. Chem.* 269:13854-13860). For example, ALDH enzymatic activity is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and a substrate such as 14 μM propionaldehyde, retinaldehyde, octylaldehyde, phenylacetaldehyde, 4-hydroxynonenal, and the like. Reduction of $NAD^+$ is monitored at 340 nm using a spectrophotometer, or by fluorescence increase using a fluoromicrophotometer.

ALDH enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043, or WO 2005/057213. In an exemplary assay, the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of $NAD^+$ to NADH at 340 nm, as described in US 2005/0171043, or WO 2005/057213. Alternative, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043, or WO 2005/057213. Detection of fluorescent resorufin at 590 nm provides amplified and more sensitive signals for any change in ALDH enzymatic activity.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like. In some instances, e.g., in some figures, micromolar (μM) is represented as "uM."

Example 1

Identification and Characterization of ALDH Agonists

Compounds were screened using a method as depicted schematically in FIG. 4. Essentially, the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of $NAD^+$ to NADH at 340 nm. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin.

For example, a 120 μl reaction mixture for ALDH enzymatic activity comprises the following components:

43 μl 150 mM sodium pyrophosphate (NaPPi) buffer, pH 9.0;

30 μl 10 mM $NAD^+$;

15 μl 80 mM acetaldehyde;

1 μl of resazurin (0.2 mg/ml in $H_2O$);

1 μl of diaphorase (1 unit, e.g., from *Clostridium kluyveri*);

2 μl of variant ALDH2 (e.g., 2 μl of variant ALDH2 at (0.5-2 μg/μl); and

28 μl of a solution comprising an agent to be tested, which agent has been resuspended in an appropriate solvent (e.g., an aqueous solution, DMSO, and the like).

Approximately 65,000 compounds were screened. A number of compounds were identified that increase the activity of ALDH2. The results are shown in Table 1, below.

TABLE 1

| Compound | Alda- | $EC_{50}$ (μM) |
|---|---|---|
| 1 | Alda-52 | 3 |
| 2 | Alda-59 | 4.6 |
| 3 | Alda-72 | 2.92 |
| 4 | Alda-71 | 16.55 |
| 5 | Alda-53 | 1.09 |
| 6 | Alda-54 | 1.72 |
| 7 | Alda-68 | 18.53 |
| 8 | Alda-61 | 6.44 |
| 9 | Alda-60 | 4.96 |
| 10 | Alda-70 | 5.57 |
| 11 | Alda-69 | 8.9 |
| 12 | Alda-73 | 3.55 |
| 13 | Alda-67 | 3.42 |
| 14 | Alda-66 | 2.66 |
| 15 | Alda-65 | 8.41 |
| 16 | Alda-68 | 12.6 |
| 17 | Alda-56 | 3.65 |

TABLE 1-continued

| Compound | Alda- | EC$_{50}$ (µM) |
|---|---|---|
| 18 | Alda-57 | 1.4 |
| 19 | Alda-64 | 2.2 |
| 20 | Alda-63 | 12.39 |
| 21 | Alda-62 | 14.69 |

The activity of compounds 1-21 in modulating ALDH2 activity is depicted in FIGS. 1-3 and 8-11. The structures of the compounds are also shown.

Figure 9:
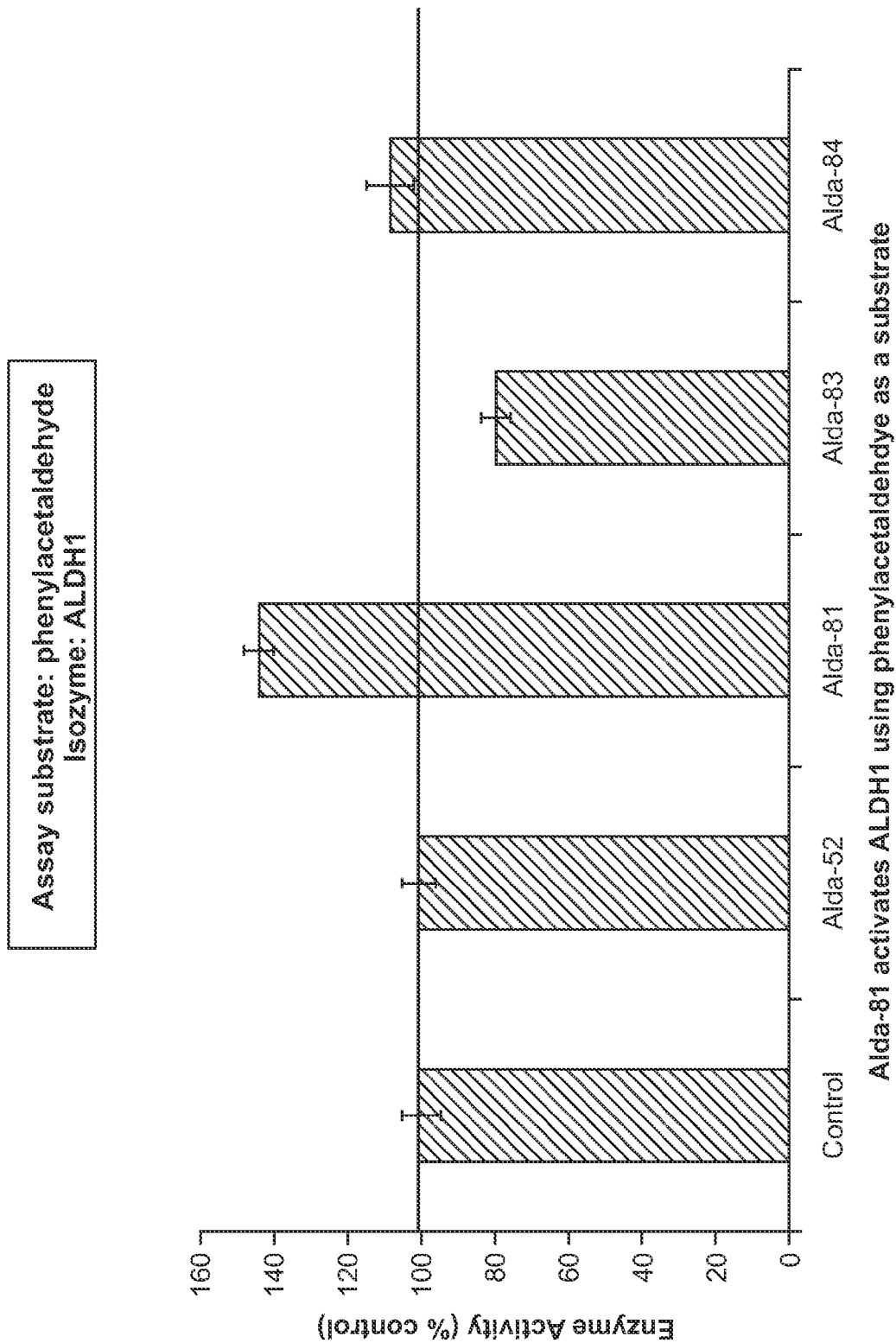
FIG. 9 depicts the effect of four exemplary activator compounds—Alda-52, Alda-81, Alda-83, and Alda-84—on ALDH1 enzymatic activity using phenylacetaldehyde as a substrate.
Figure 10:
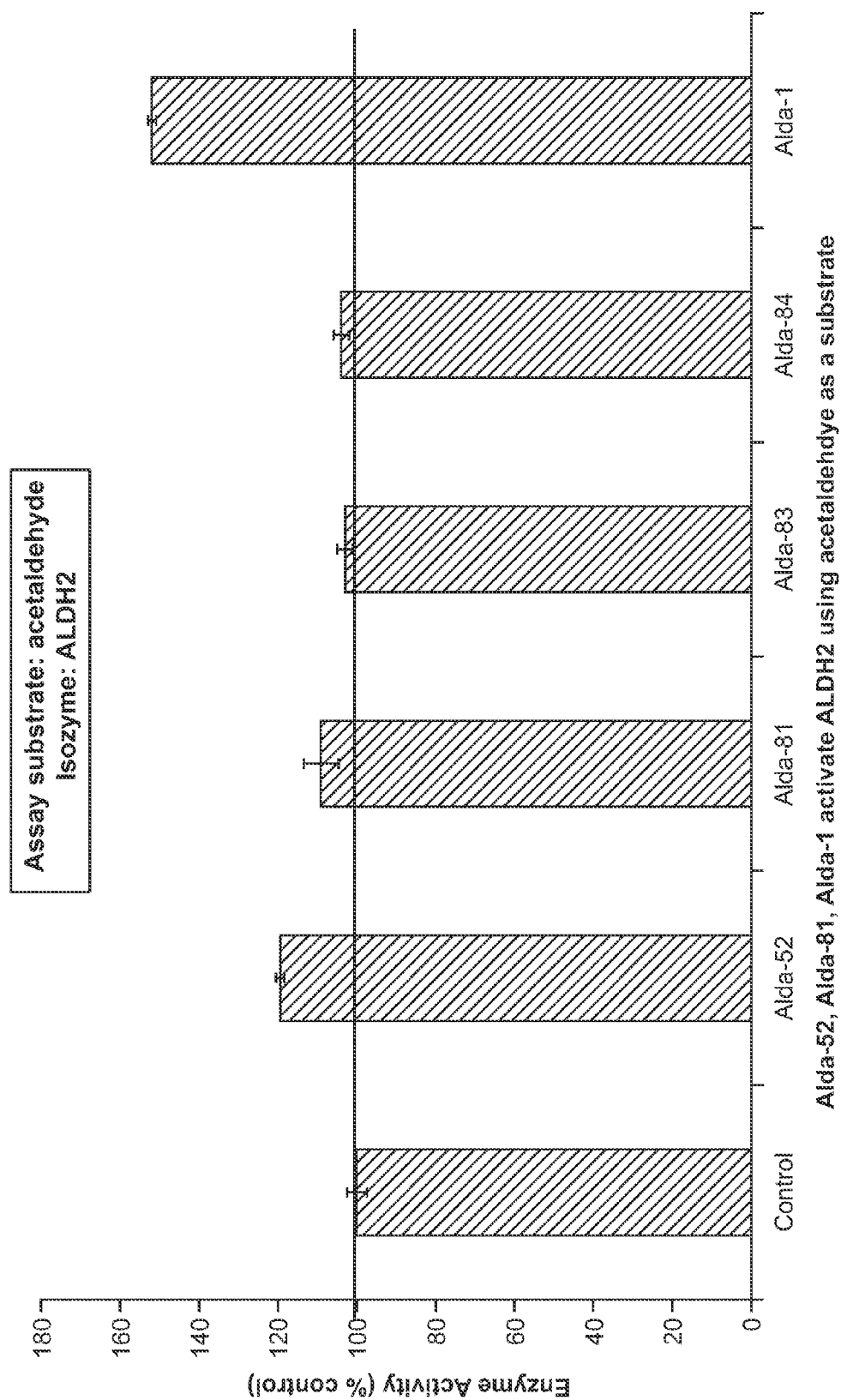
FIG. 10 depicts the effect of five exemplary activator compounds—Alda-52, Alda-81, Alda-83, Alda-84, and Alda-1—on ALDH2 enzymatic activity using acetaldehyde as a substrate.
Figure 11:
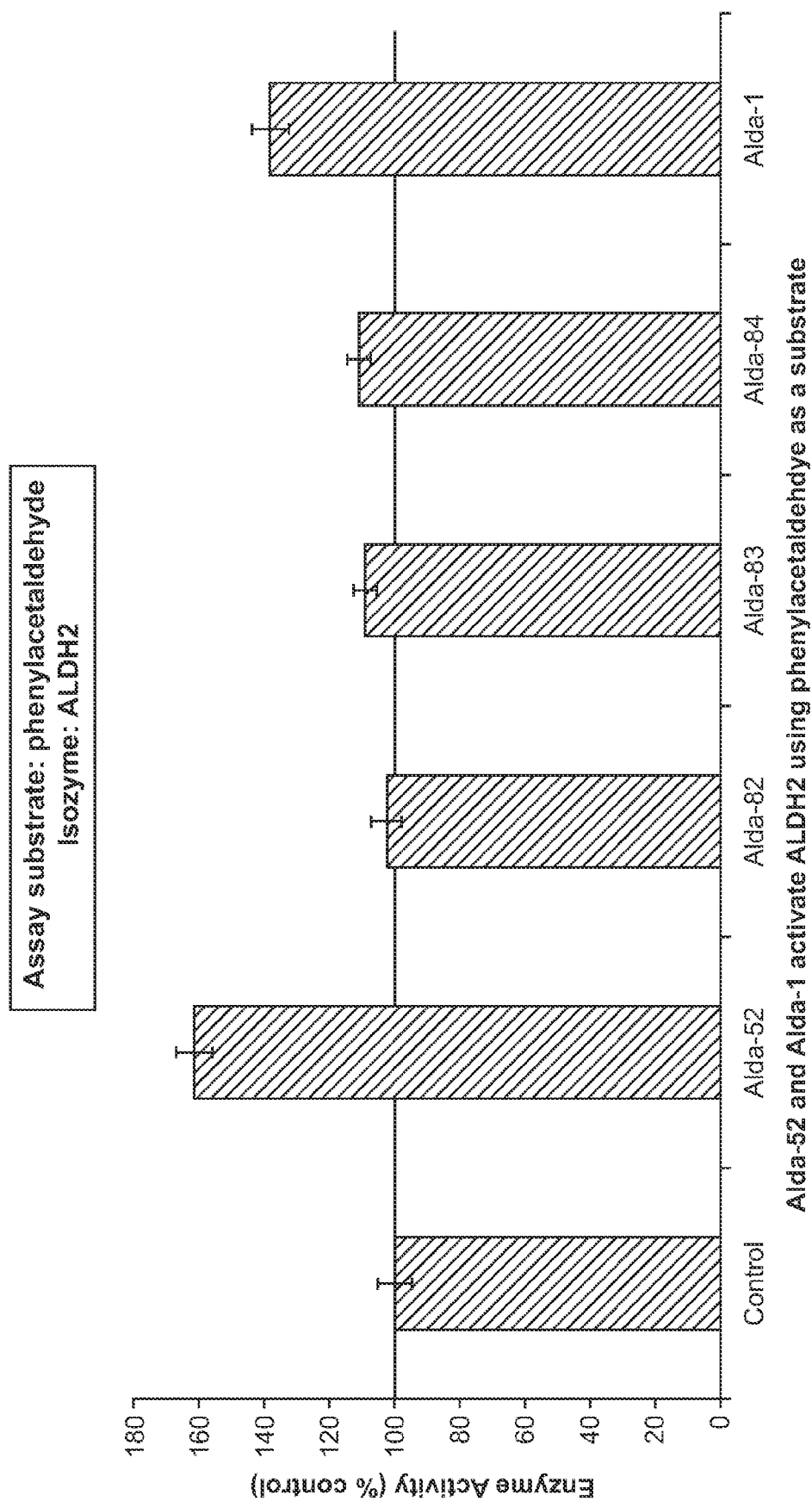
FIG. 11 depicts the effect of four exemplary activator compounds—Alda-52, Alda-81, Alda-83, Alda-84, and Alda-1—on ALDH2 enzymatic activity using phenylacetaldehyde as a substrate.

FIGS. 8-11 depicts the structures of ALDH1 activators Alda-81, Alda-83, and Alda-84. Alda-81, Alda-83, and Alda-84 were identified by high throughput screening of 130,000 compounds against E488K ALDH1 mutant recombinant protein. The screening assays used octylaldehyde (an example of longer chain aliphatic aldehyde) and phenylacetaldehdye (an example of aromatic aldehyde), instead of acetaldehyde. FIG. 9 shows examples of substrate selectivity of ALDH agonists. FIGS. 10 and 11 show substrate selectivity and ALDH isozyme selectivity of ALDH agonists.

Example 2

Plant-Derived ALDH Agonists

Reagents for plant-derived compounds safrole, isosafrole, piperine, sesamin, capsaicin were purchased from Sigma-Aldrich Chemicals and dihydromethysticin was purchased from AvaChem Scientific. Piperine related compounds, Alda-101 to Alda-112, were synthesized by standard organic chemistry. All testing compounds were dissolved in dimethyl-sulfoxide (DMSO) to obtain a stock solution of 20 mM. Different recombinant ALDH isozymes with a His-epitope tag at the N-terminus were constructed, cloned and expressed in BL21 *E. coli* host cells according published methods (Chen et al., 2008 Science 321:1493). The bacteria were subjected to 0.5 mM IPTG induction for protein expression at 30° C. Purification of the recombinant proteins by affinity nickel columns were carried out using a standard protocol according to manufacturer's instructions (Novagen, Wis., USA).

ALDH enzymatic activity was determined spectrophotometrically using purified recombinant protein (15 ug) in the reductive reaction of NAD$^+$ to NADH at λ340 nm (Rex et al., 1985, *Alcohol Clin Exp Res* 9: 147). All the assays in the presence of absence of a testing compound were carried out at 25° C. in 0.1 sodium pyrophosphate buffer, pH=9.5, 2.4 mM NAD+ and 10 mM acetaldehyde or phenylacetaldehyde as a substrate.

Figure 13:
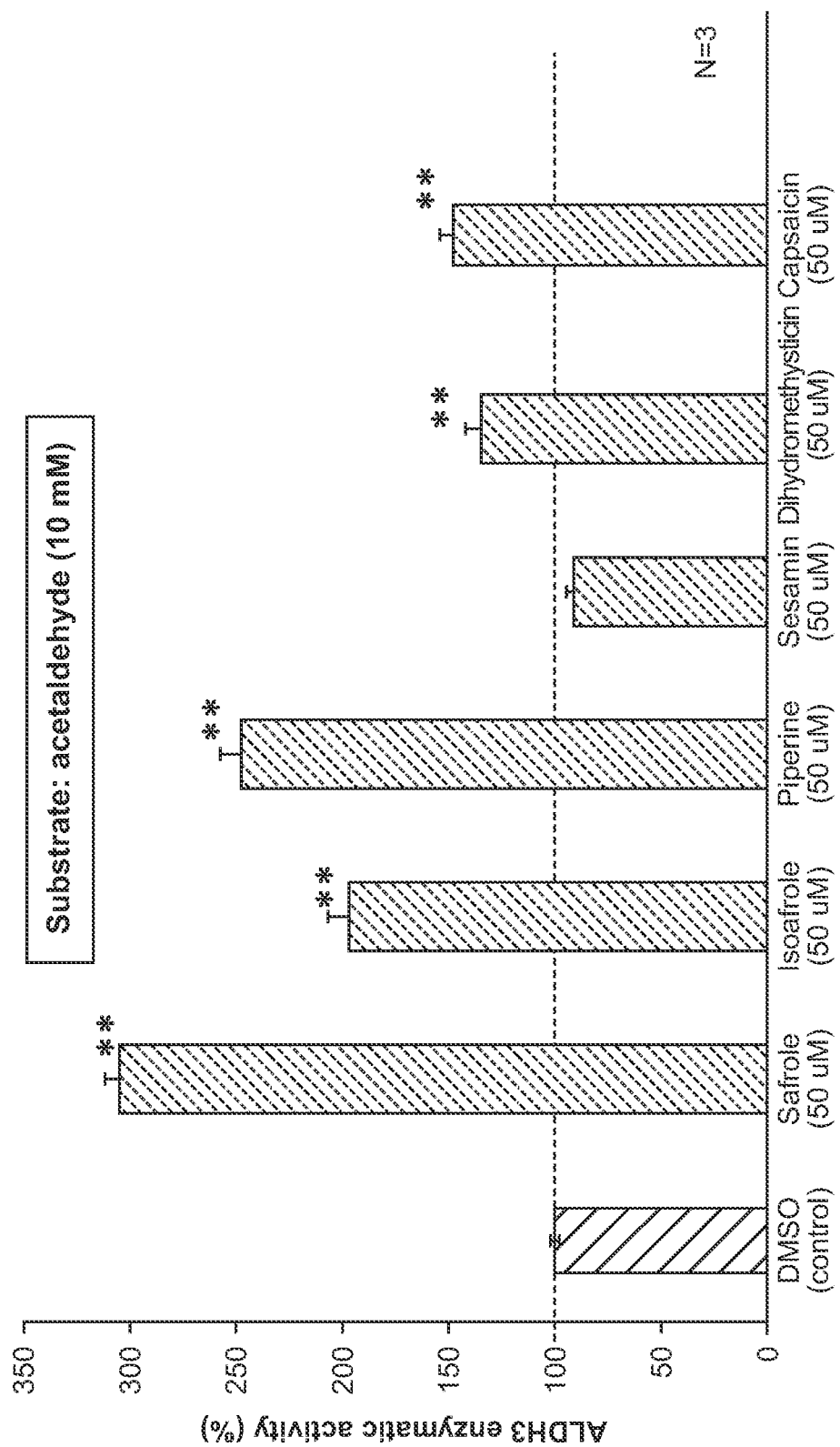
FIG. 13 depicts activation of ALDH3 by various compounds using acetaldehyde as substrate.

FIG. 13 depicts: Activation of ALDH3 by different compounds (50 uM) in a 3-minute kinetic assay using acetaldehyde as a substrate. Enzymatic activity is expressed in percentage using DMSO vehicle alone as the control (100%), (n=3; **p<0.01 vs. control).

Figure 14:
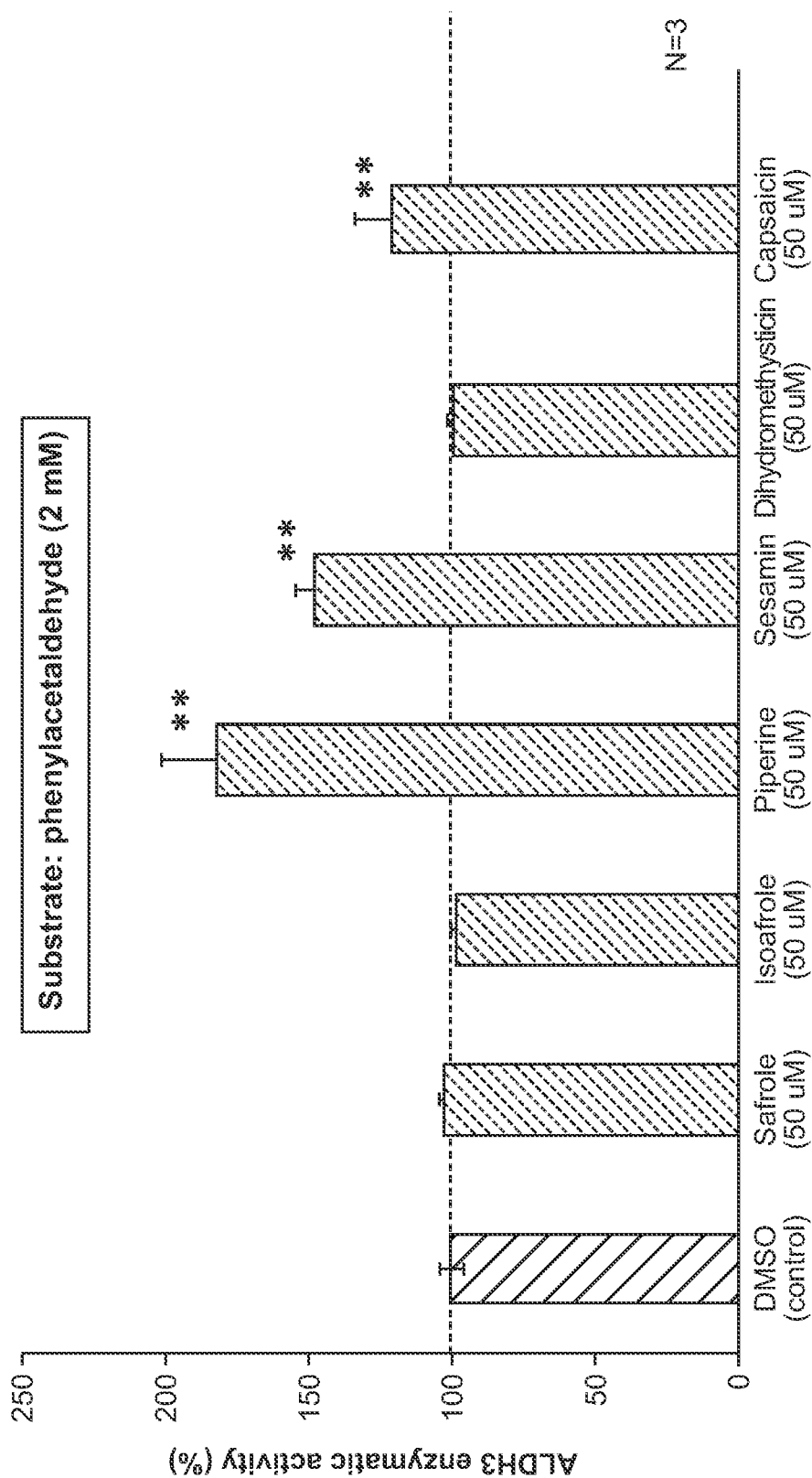
FIG. 14 depicts activation of ALDH3 by various compounds using phenylacetaldehyde as substrate.

FIG. 14 depicts: Activation of ALDH3 by different compounds (50 uM) in a 3-minute kinetic assay using phenylacetaldehyde as a substrate. Enzymatic activity is expressed in percentage using DMSO vehicle alone as the control (100%), (n=3; **p<0.01 vs. control).

Figure 15:
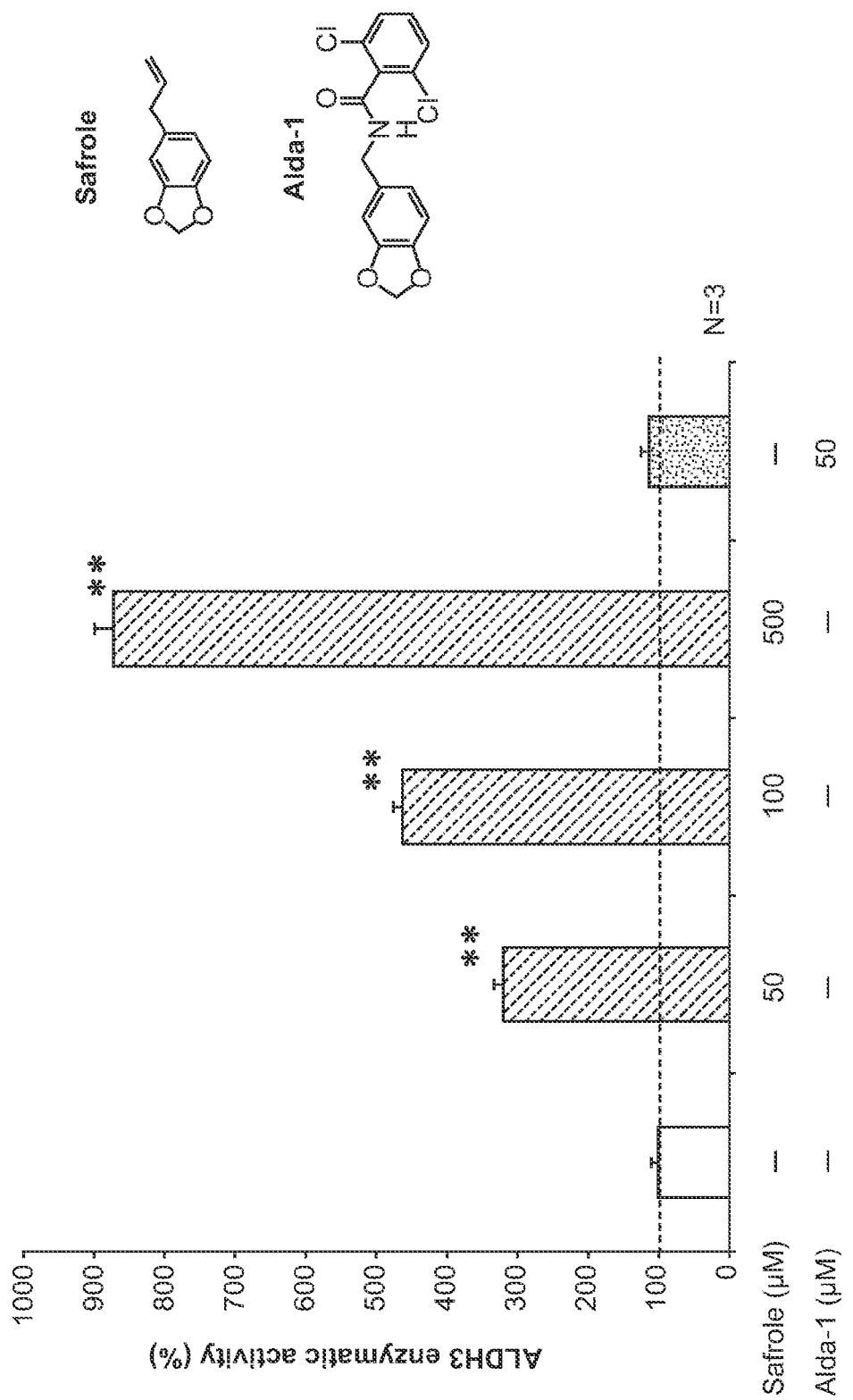
FIG. 15 depicts dosate effect of safrole on ALDH3 enzymatic activity using acetaldehyde as substrate.

FIG. 15 depicts: Dosage effect of safrole (Alda-89) on ALDH3 enzymatic activity using acetaldehyde as a substrate. Note that Alda-1 does not have any effect on enzymatic activity of ALDH3 isozyme, (n=3; **p<0.01 vs. control).

Figure 16:
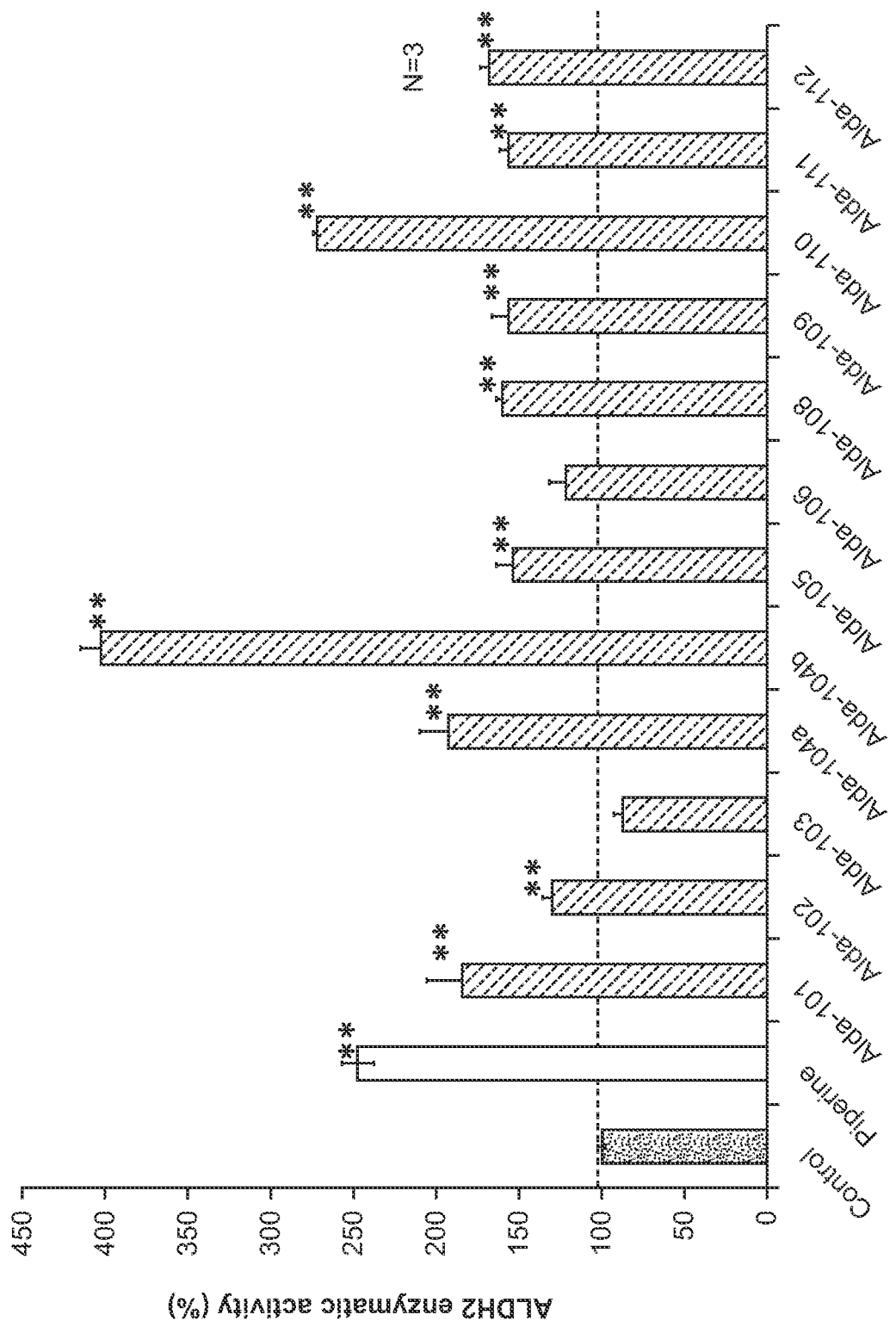
FIG. 16 depicts the effect of various compounds, designated Alda-101 to Alda-112, on ALDH3 enzymatic activity acetaldehyde as substrate.

FIG. 16 depicts: Activation of ALDH3 enzymatic activity by synthetic derivative compounds (Alda-101-Alda-112, 50 uM) of piperine using acetaldehyde as a substrate (n=3; **p<0.01 vs. control).

Figure 17:
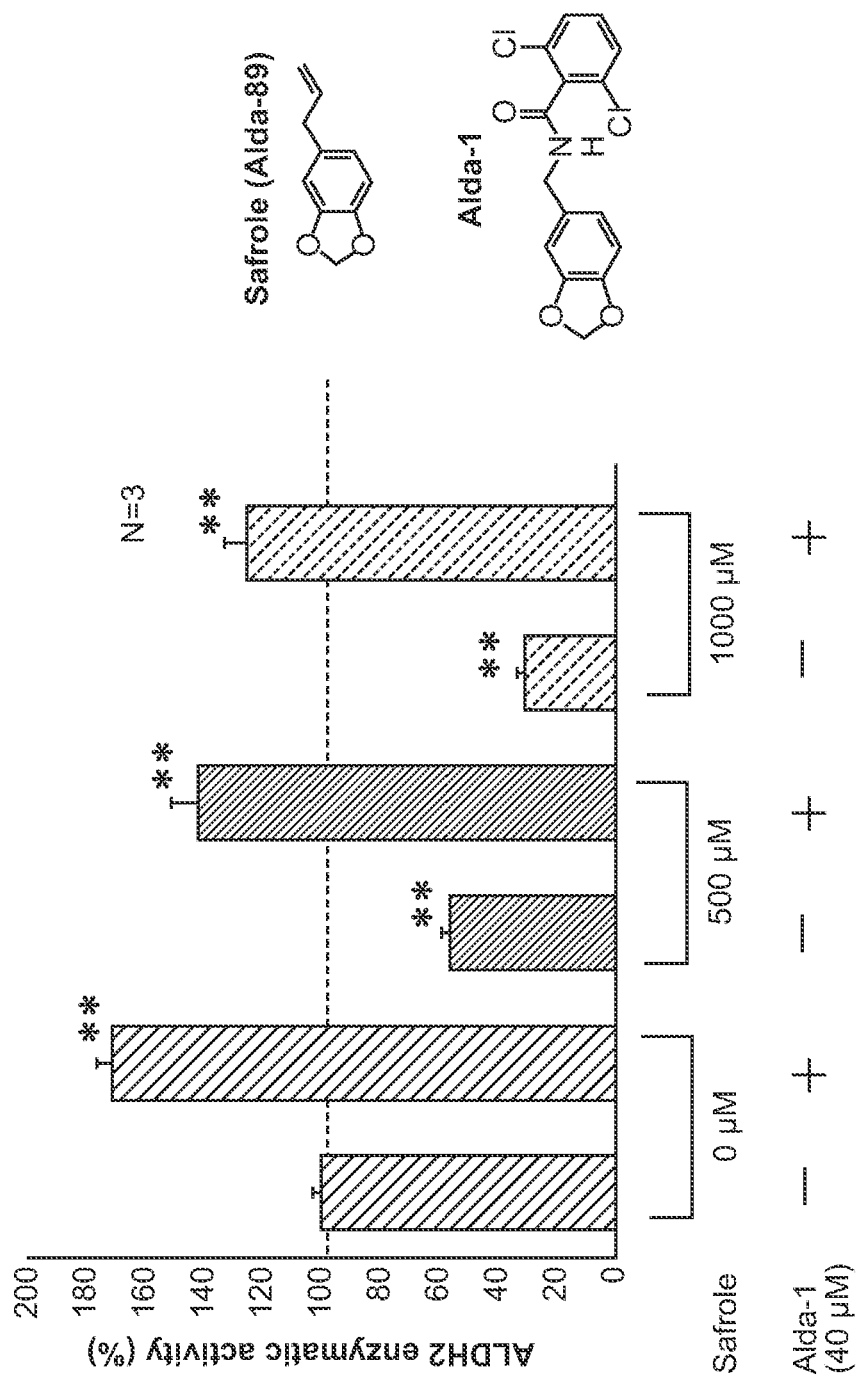
FIG. 17 depicts the inhibitory effect of high concentration of safrole on ALDH2 enzymatic activity using acetaldehyde as substrate.

FIG. 17 depicts: Inhibitory effect of high concentration of safrole (Alda-89, 500 uM & 1000 uM) on enzymatic activity of ALDH2 isozyme using acetaldehyde as a substrate. This inhibition can be prevented and reversed by co-incubation of an ALDH2 activator Alda-1 (40 uM), (n=3; **p<0.01 vs. control).

Figure 18:
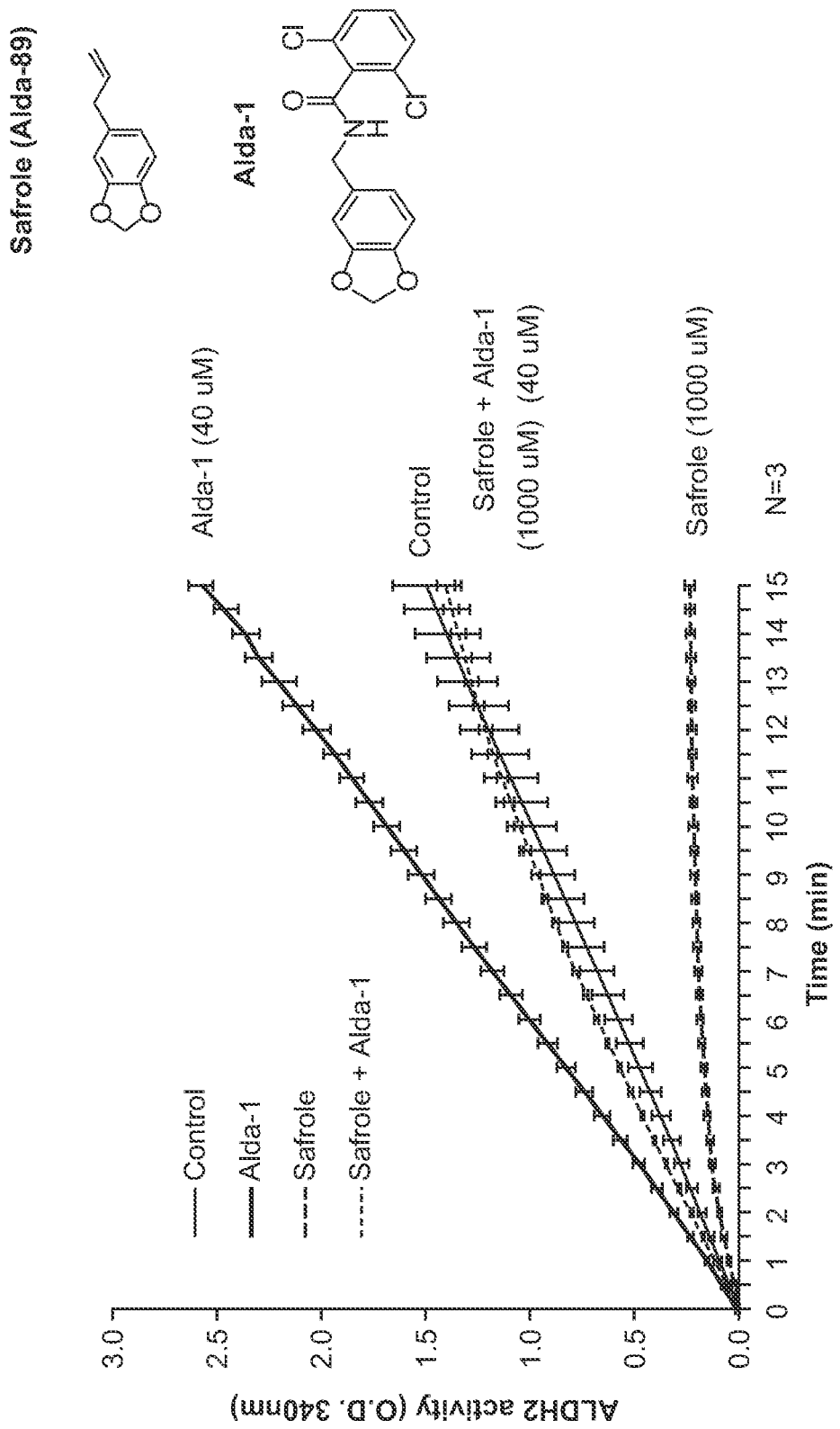
FIG. 18 depicts 15-minute kinetic measurements of the inhibitory effect of 1000 μM safrole on ALDH2 enzymatic activity using acetaldehyde as substrate.

FIG. 18 depicts: 15-minute kinetic measurements of inhibitory effect of safrole (Alda-89, 1000 uM) on enzymatic activity of ALDH2 isozyme using acetaldehyde as a substrate. This inhibition can be prevented and reversed by co-incubation of an ALDH2 activator Alda-1 (40 uM). Control is DMSO vehicle alone.

Example 3

Treatment of Radiation Dermatitis with ALDH Agonists

Radiation dermatitis is a painful side effect experienced by human patients undergoing radiotherapy for solid tumors. Radiation dermatitis is believed to be due to acute oxidative injury to the skin, which leads to lipid peroxidation and the accumulation of reactive aldehydes, such as 4-hydrorxynonenal. In this example, Alda-1 is shown to reduce radiation dermatitis by maintaining ALDH activity during exposure to radiation. C57Bl/6J mice were exposed to 6 Gy gamma irradiation per day (applied directly to the shaved back area over a period of 5 minites) in the absence or presence of 200 µl of 3 mM Alda-1 (in 95% ethanol) or 200 µl 95% ethanol alone (vehicle control). Alda-1 or ethanol alone was applied topically 5 minutes before and 5 minutes after each radiation treatment for a total of 10 sessions (60 Gy total, 6 Gy/day with a two-day break after 5 sessions). Mice were euthanized and exposed skin was dissected, and either homogenized in Lysis Buffer (for ALDH2 activity assay, FIG. 18) or fixed in 4%-paraformaldehyde (for histological analysis, FIG. 19).

Figure 19:
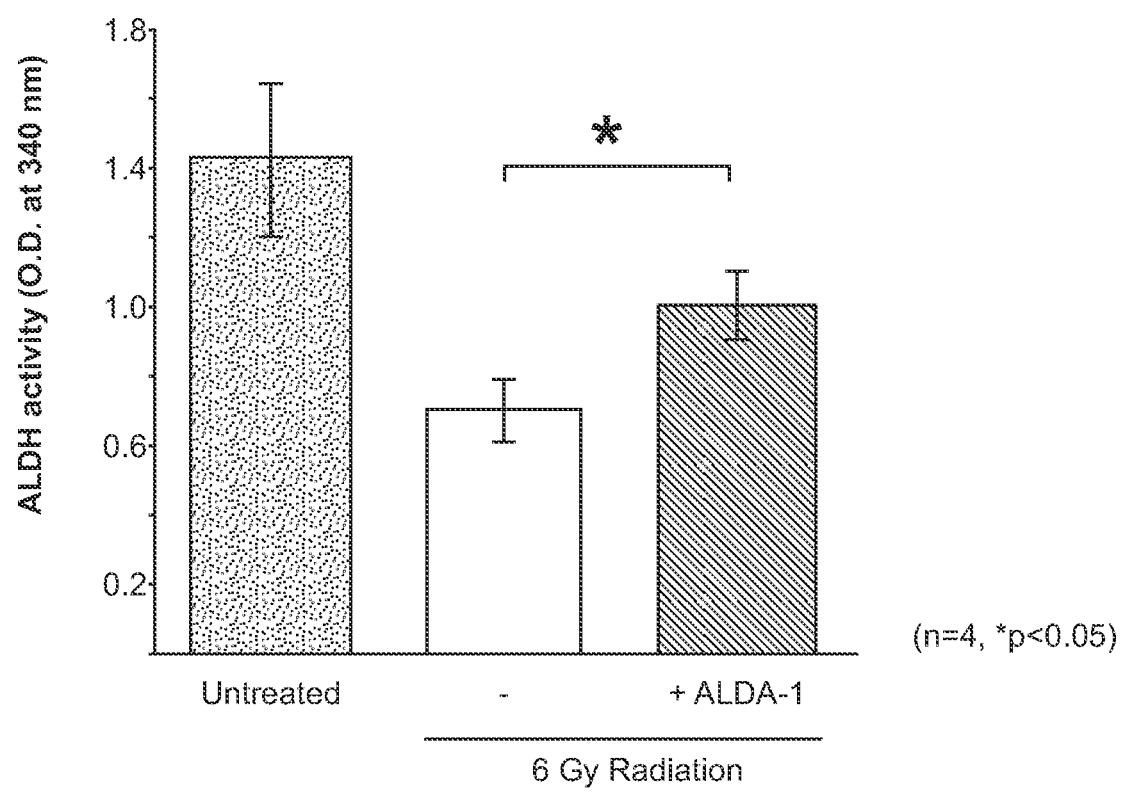
FIG. 19 depicts the effect of Alda-1 on ALDH activity in skin exposed to 6 Gy irradiation.

FIG. 19 depicts: 6 Gy gamma radiation significantly reduced ALDH activity, when compared to non-irradiated, control skin. Topical administration of 3 mM Alda-1 (in 95% Ethanol) significantly attenuated the inhibition of ALDH induced by 6 Gy gamma irradiation (n=4, *P<0.05).

Figure 20:
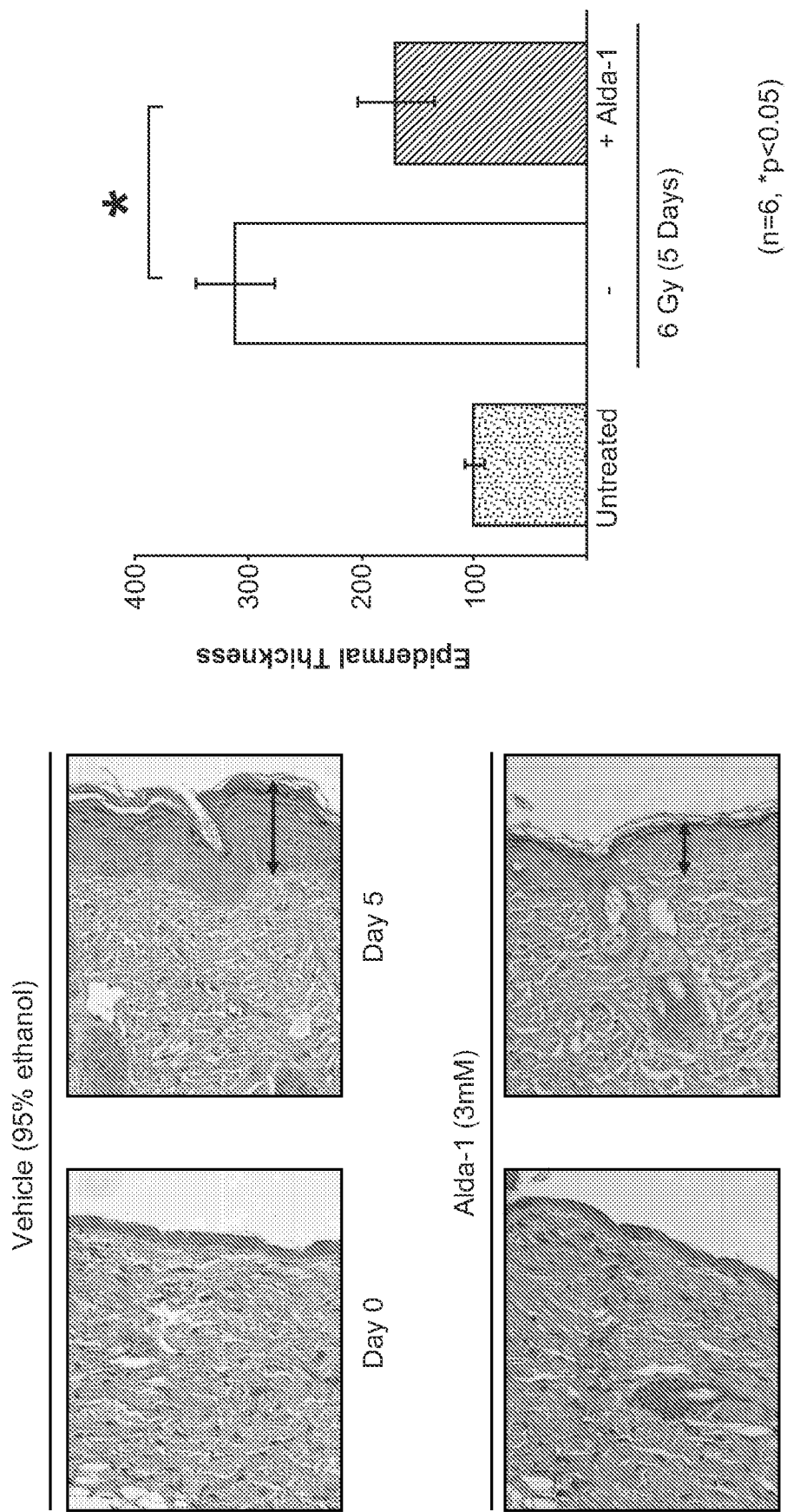
FIG. 20 depicts the effect of Alda-1 on reducing skin damage induced by radiation exposure.

FIG. 20 depicts: Epidermal thickening after radiation in C57Bl/6J mice. Epidermal thickening is used as a measure of radiation-induced skin damage (Kim et al, 2004 Journal of the American College of Nutrition, Vol. 23, 157-162). Quantitative analysis of heamatoxylin and eiosin (H&E) stained skin sections revealed that epidermal thickening, induced by 5 days exposure to 6 Gy irradiation, was significantly reduced in the Alda-1 treated group, when compared to the vehicle control (n=6, *p<0.05)

Example 4

Sensitizing a Tumor to Radiation Treatment

In order to determine the impact of Alda-1 on the effectiveness of radiation therapy, C57Bl/6J mice were inoculated subcutaneously with SCC VII murine squamous cell carcinoma cells (5×10$^5$) and exposed to radiation therapy (250 cGy/day) in the absence or presence of Alda-1 (200 µl of 3 mM Alda-1 in 95% ethanol) or ethanol (200 µl of 95% ethanol) applied 5 min before and 5 min after radiation. Tumor volume was measured daily until the tumor reached four times its starting size at treatment onset (Ning et al., 2008, *Mol Cancer Therapy* 7:1569-78).

Figure 21:
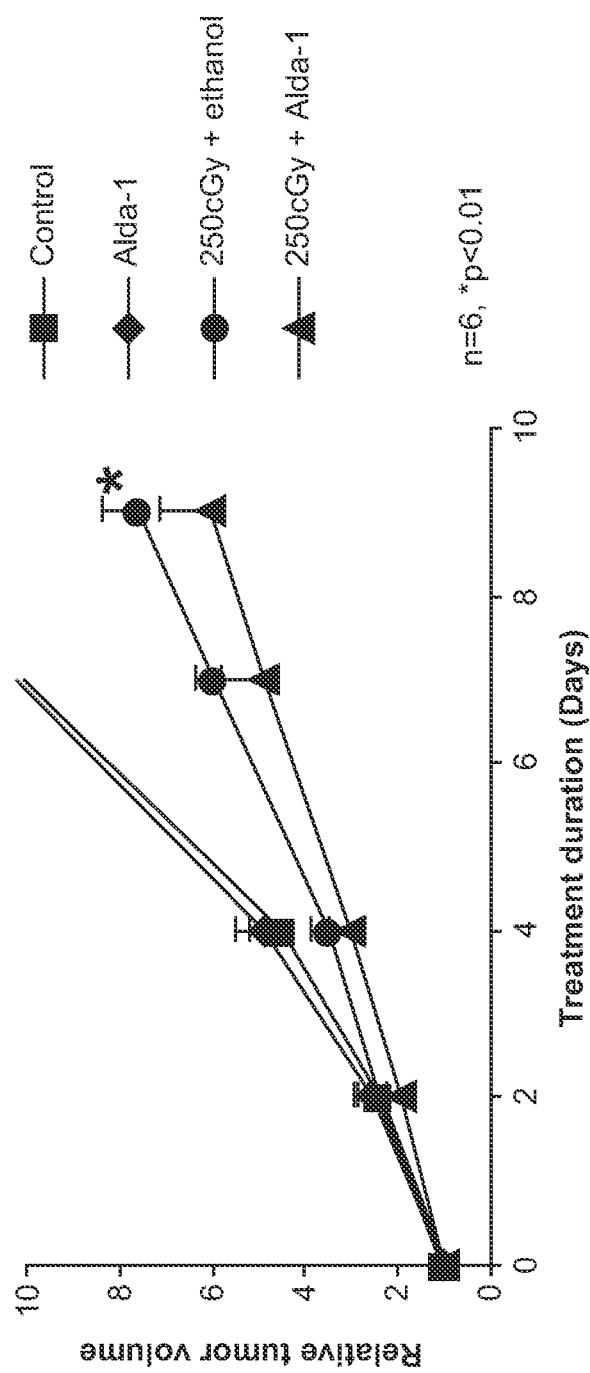
FIG. 21 depicts the effect of Alda-1 and radiation in reducing tumor growth.

FIG. 21 depicts: No negative impact of Alda-1 treatment on radiation therapy. Therapeutic application of Alda-1 in radiation dermatitis, does not affect the effectiveness of radiation therapy to inhibit tumor growth. On the contrary, treatment of Alda-1 actually increased significantly the sensitivity of the tumor to radiation treatment (red line) when compare to the ethanol vehicle control (green line) (n=6, *p<0.01). Alda-1 had no effect on tumor growth in non-irradiated mice (blue line) when compare to ethanol treated mice (black line).

Example 5

Enhanced Metabolism and Detoxification of Ethanol by ALDH Agonists

C57Bl/6J mice (male, 25-30 g), were used in the experiments to demonstrate enhanced detoxification of ethanol intake. Combination of ALDH agonists Alda-1 (83 mg/kg) and Alda-89 (166 mg/kg) or PEG400 vehicle alone were delivered orally to the animals 15 minutes before the challenge of ethanol at 3.3 g/kg. Ethanol was delivered orally also by a 47.5% (v/v) solution. Functional analysis of vertical rearing activity and behavioral score (Majchrowicz, 1975, Psychopharmacolgia 43:245-254) were conducted every 30 minutes after ethanol intake for a period of 120 minutes. For the experiment of blood alcohol level (BAL) measurement, 50 ul of blood sample was taken from the saphenous vein of each animal at time point of 45 minutes after ethanol delivery. BAL was determined by a standard method (Zahr et al., 2009, Neuropsychopharmacology 34, 1427-1442) using a Analox alcohol analyzer (Lunenburg, Mass.).

Figure 22:
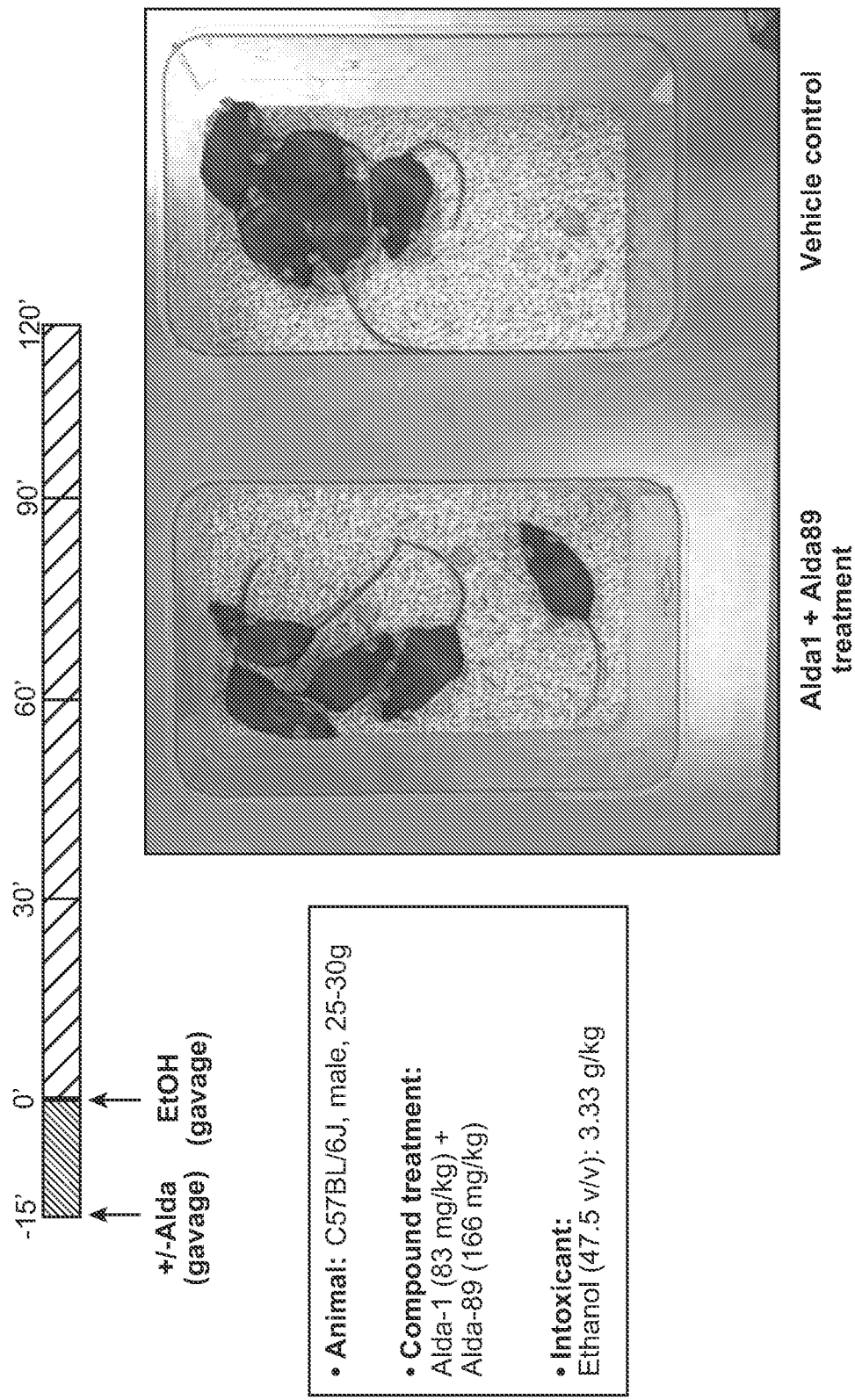
FIG. 22 depicts detoxification of ethanol by ALDH agonists.

FIG. 22 depicts: Experimental protocol of enhanced metabolism and detoxification of ethanol by ALDH agonists. 15 animals each for the treatment and control groups were used in the functional analysis by rearing activity (FIG. 23) and behavioral scoring (FIG. 24). 10 animals each were used in the determination of blood alcohol level (FIG. 25).

Figure 23:
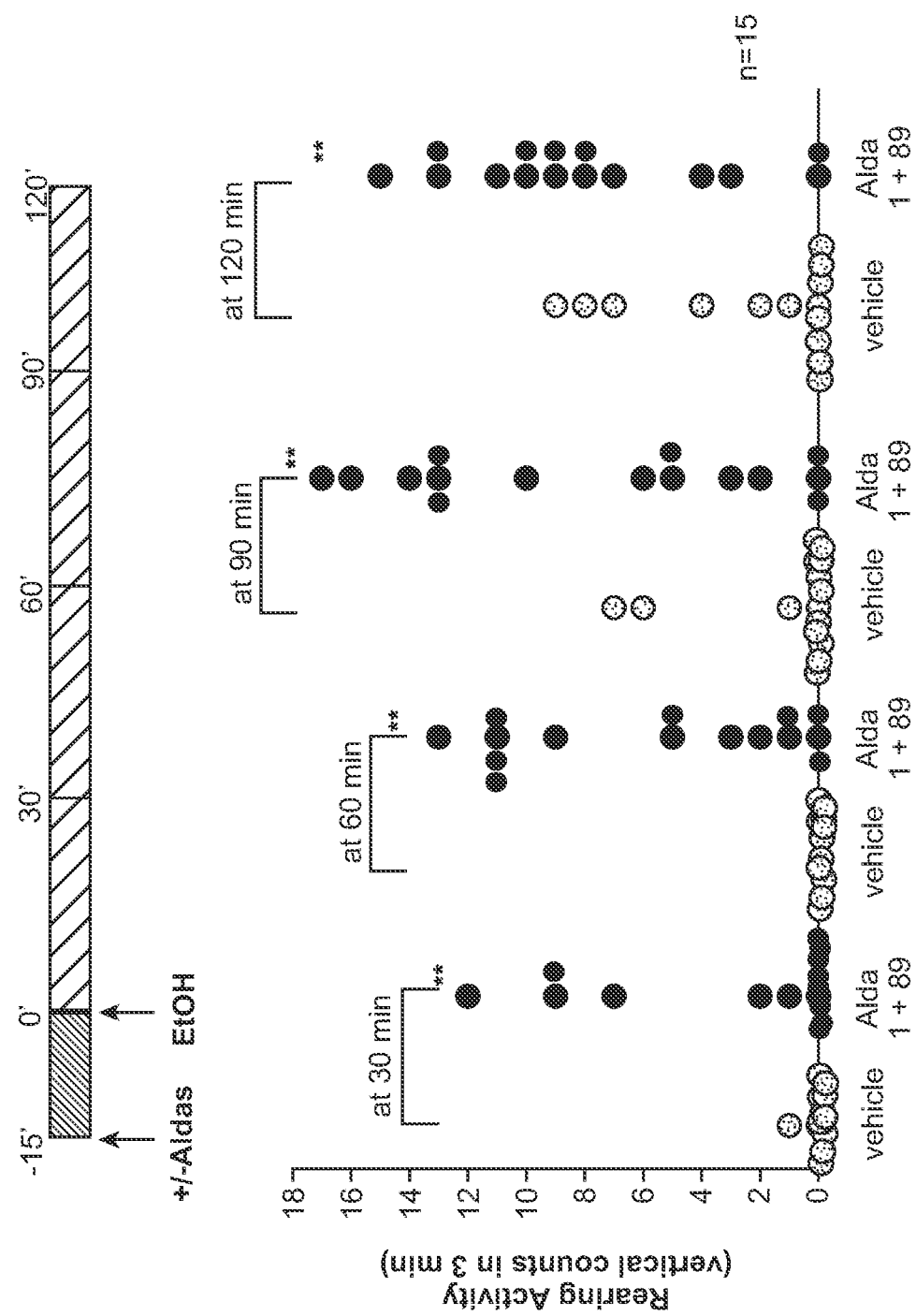
FIG. 23 depicts functional analysis by rearing activity of detoxification of ethanol by ALDH agonists.

FIG. 23 depicts: Functional analysis by rearing activity. Vertical counts were monitored and totalled for each animal for in a 3-minute period at 30, 60, 90 and 120 minutes after ethanol intake (n=15; **p<0.01 vs. vehicle control).

Figure 24:
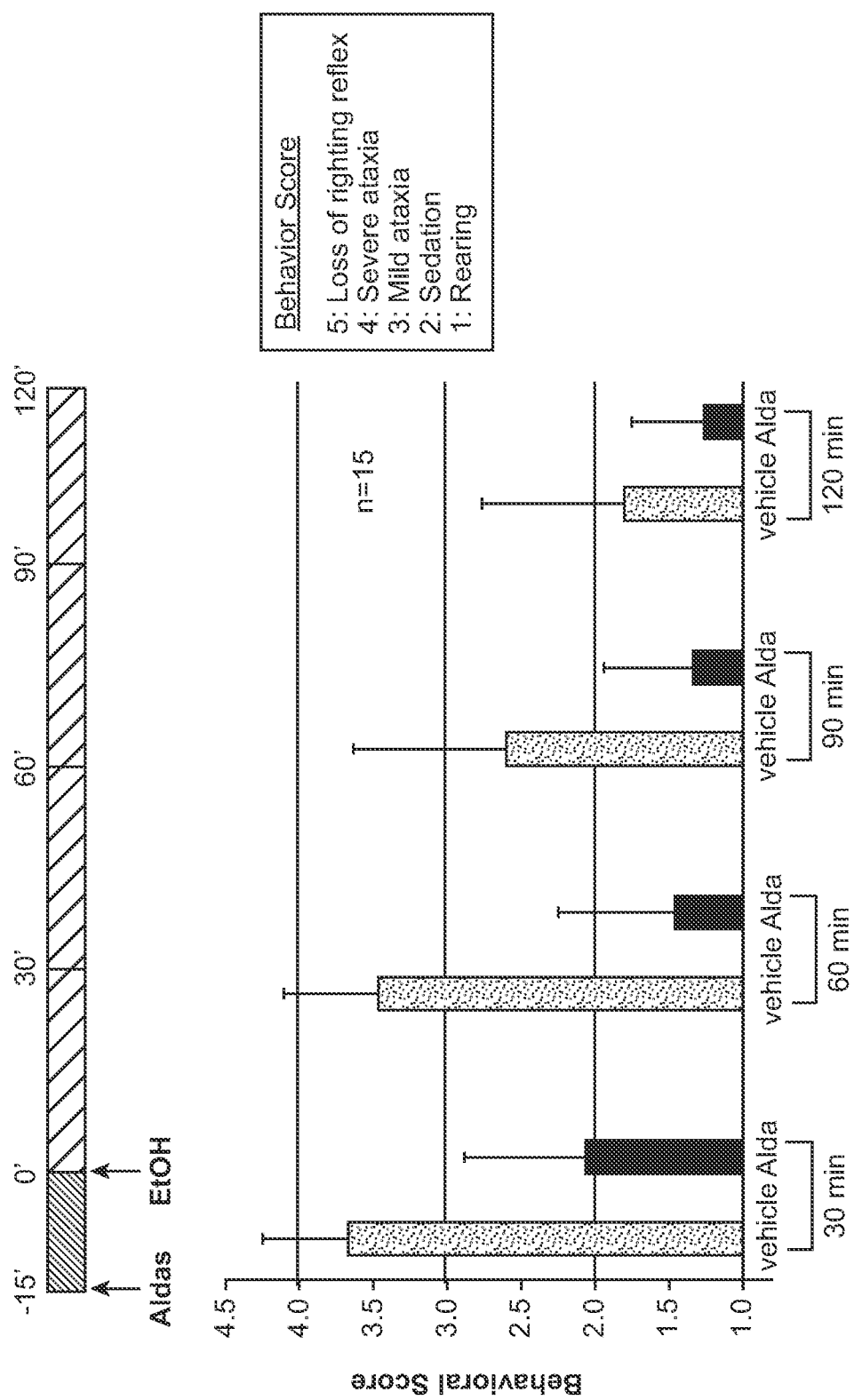
FIG. 24 depicts functional analysis by behavioral score of detoxification of ethanol by ALDH agonists.

FIG. 24 depicts: Functional analysis by behavioral score. Each animal was monitored and scored at a 30, 60, 90 and 120 minutes after ethanol intake using an assigned scoring system of 1: rearing, 2: sedation, 3: mild ataxia, 4: severe ataxia, 5: loss of righting reflex. Each column is expressed as an average of 15 animals.

Figure 25:
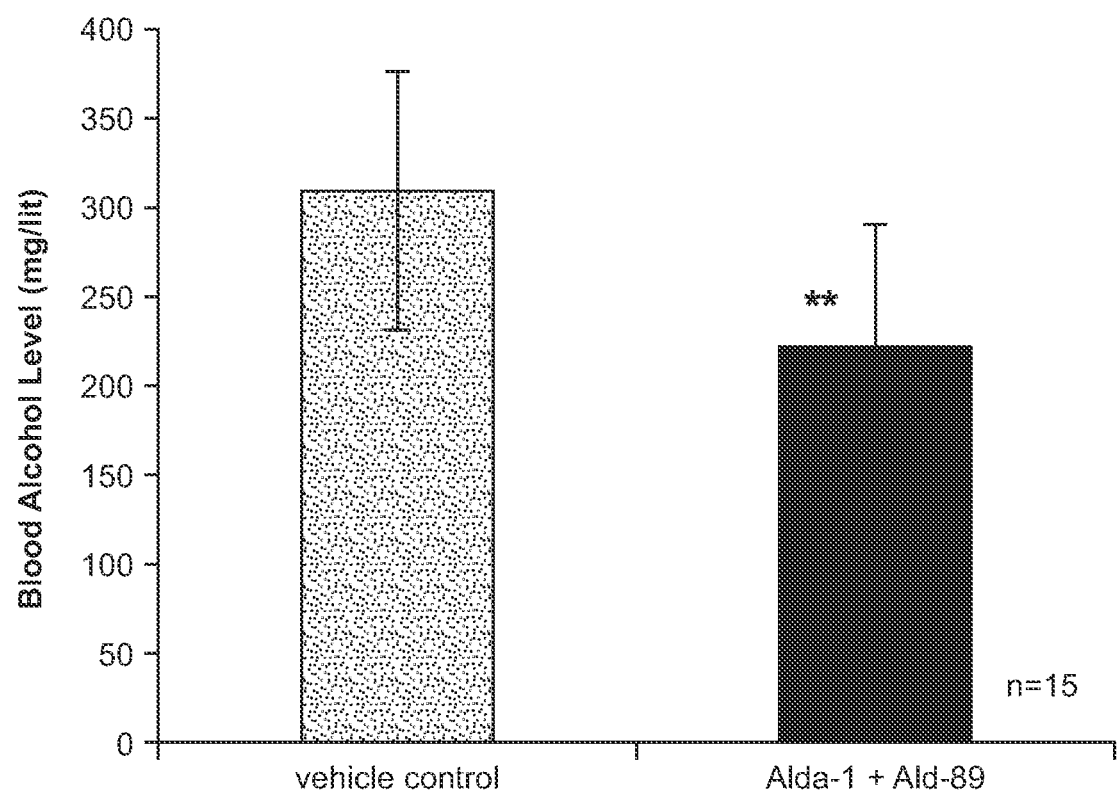
FIG. 25 depicts the effect of ALDH agonist on blood alcohol levels.

FIG. 25 depicts: Blood alcohol level measurement of the animals treated with ALDH agonists or vehicle alone. Blood samples were withdrawn from saphenous vein from each animal at time point of 45 minutes after ethanol intake (n=15; **p<0.01 vs. vehicle control).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of Formula Ic:

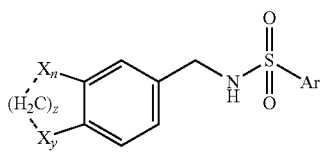

wherein $X_n$ and $X_y$ are each independently H, C, N, O, or a halogen; where n is the integer 0 or 1; where y is the integer 0 or 1;

wherein ⋯ (dotted line) is an optional bond;

wherein z is the integer 0, 1, or 2, with the provisos that: 1) z=0 when X=halogen and ⋯ is not a bond; and 2) when z=0, X=O, ⋯ is not a bond, and one or more oxygen atoms (X) are present, oxygen is attached to a methyl group;

where Ar is selected from a substituted phenyl and a substituted thiophene group; wherein the phenyl group is substituted with one or more $C_1$ to $C_7$ alkyl and an isoxazolyl group, and the thiophene group is substituted with $C(O)NH_2$;

or a pro-drug, a pharmaceutically acceptable salt, or a derivative thereof.

2. The compound of claim 1, wherein $X_n$ and $X_y$ are both O.

3. The compound of claim 1, wherein z is 1.

4. The compound of claim 1, wherein Ar is a substituted phenyl.

5. The compound of claim 4, wherein the phenyl is substituted with a methyl group.

6. The compound of claim 1, wherein the isoxazolyl group is substituted with one or more methyl groups.

7. The compound of claim 1, wherein Ar is a substituted thiophene group.

8. A compound having a structure selected from:

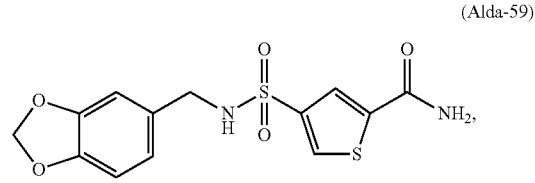
(Alda-59)

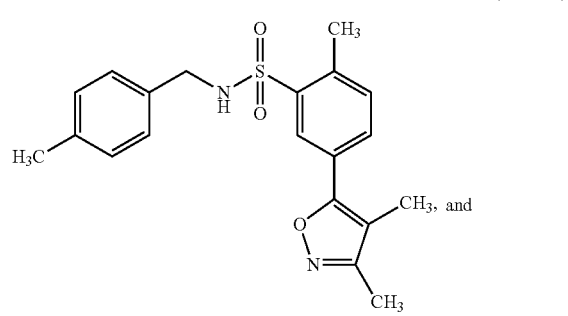
(Alda-61)

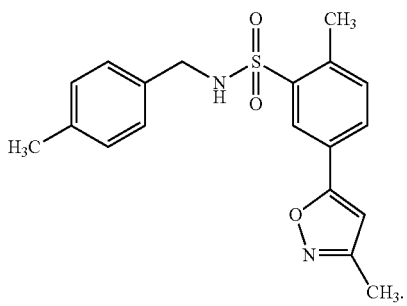
(Alda-60)

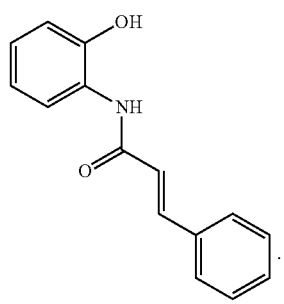
(Alda-84)

9. A pharmaceutical composition comprising:
a) a compound of claim 1; and
b) a pharmaceutically acceptable excipient.

10. A pharmaceutical composition comprising:
a) a compound of claim 8; and
b) a pharmaceutically acceptable excipient.

11. A method of reducing a level of aldehyde present at a toxic level in an individual to below the toxic level comprising administering to an individual an effective amount of a compound of claim 1.

12. The method of claim 11, wherein the individual has alcohol intolerance, alcohol addiction, or an alcohol abuse disorder.

13. A method of treating a disease or disorder selected from alcohol intolerance, alcohol addiction, alcohol abuse disorder, methanol poisoning, ethylene glycol monomethyl ether poisoning, and poisoning due to other xenogenic or biogenic aldehyde compounds, comprising administering to an individual an effective amount of a compound of claim 1.

14. The method of claim 13, wherein the disease or disorder is alcohol addiction.

15. The method of claim 13, wherein the disease or disorder is alcohol intolerance.

16. The method of claim 13, wherein the individual is heterozygous or homozygous for the ALDH2*2 allele.

17. The method of claim 13, wherein the compound is administered parenterally or orally.

18. A method of detoxifying alcohol in an individual in need thereof, the method comprising administering to the individual an effective amount of a compound of claim 1.

19. A pharmaceutical composition comprising:
a) a compound having the structure:

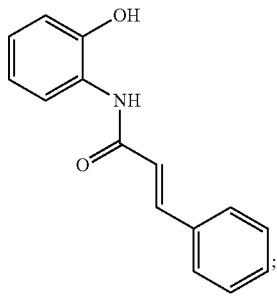
(Alda-84)

and
b) a pharmaceutically acceptable excipient.

20. A method of reducing a level of aldehyde present at a toxic level in an individual to below the toxic level comprising administering to an individual an effective amount of a pharmaceutical composition of claim 19.

21. A method of treating a disease or disorder selected from alcohol intolerance, alcohol addiction, alcohol abuse disorder, methanol poisoning, ethylene glycol monomethyl ether poisoning, and poisoning due to other xenogenic or biogenic aldehyde compounds, comprising administering to an individual an effective amount of a pharmaceutical composition of claim 19.

* * * * *

SEQUENCE LISTING

```
<160> NUMBER OF SEQ ID NOS: 6

<210> SEQ ID NO 1
<211> LENGTH: 517
<212> TYPE: PRT
<213> ORGANISM: Homo sapiens

<400> SEQUENCE: 1

Met Leu Arg Ala Ala Ala Arg Phe Gly Pro Arg Leu Gly Arg Arg Leu
1               5                   10                  15

Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
        35                  40                  45

Val Ser Arg Lys Thr Phe Pro Thr Val Asn Pro Ser Thr Gly Glu Val
    50                  55                  60

Ile Cys Gln Val Ala Glu Gly Asp Lys Glu Asp Val Asp Lys Ala Val
65                  70                  75                  80

Lys Ala Ala Arg Ala Ala Phe Gln Leu Gly Ser Pro Trp Arg Arg Met
                85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160
```

Ile Pro Ile Asp Gly Asp Phe Phe Ser Tyr Thr Arg His Glu Pro Val
            165                 170                 175

Gly Val Cys Gly Gln Ile Ile Pro Trp Asn Phe Pro Leu Leu Met Gln
        180                 185                 190

Ala Trp Lys Leu Gly Pro Ala Leu Ala Thr Gly Asn Val Val Val Met
    195                 200                 205

Lys Val Ala Glu Gln Thr Pro Leu Thr Ala Leu Tyr Val Ala Asn Leu
210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
                260                 265                 270

Ala Ala Gly Ser Ser Asn Leu Lys Arg Val Thr Leu Glu Leu Gly Gly
            275                 280                 285

Lys Ser Pro Asn Ile Ile Met Ser Asp Ala Asp Met Asp Trp Ala Val
290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
                340                 345                 350

Asp Ser Lys Thr Glu Gln Gly Pro Gln Val Asp Glu Thr Gln Phe Lys
            355                 360                 365

Lys Ile Leu Gly Tyr Ile Asn Thr Gly Lys Gln Glu Gly Ala Lys Leu
370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
                420                 425                 430

Val Val Gly Arg Ala Asn Asn Ser Thr Tyr Gly Leu Ala Ala Ala Val
            435                 440                 445

Phe Thr Lys Asp Leu Asp Lys Ala Asn Tyr Leu Ser Gln Ala Leu Gln
450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Glu Val Lys Thr Val Thr Val Lys Val
            500                 505                 510

Pro Gln Lys Asn Ser
            515

<210> SEQ ID NO 2
<211> LENGTH: 517
<212> TYPE: PRT
<213> ORGANISM: Homo sapiens

<400> SEQUENCE: 2

Met Leu Arg Ala Ala Ala Arg Phe Gly Pro Arg Leu Gly Arg Arg Leu

```
  1               5               10              15
Leu Ser Ala Ala Ala Thr Gln Ala Val Pro Ala Pro Asn Gln Gln Pro
            20              25              30
Glu Val Phe Cys Asn Gln Ile Phe Ile Asn Asn Glu Trp His Asp Ala
            35              40              45
Val Ser Arg Lys Thr Phe Pro Thr Val Asn Pro Ser Thr Gly Glu Val
            50              55              60
Ile Cys Gln Val Ala Glu Gly Asp Lys Glu Asp Val Asp Lys Ala Val
65              70              75              80
Lys Ala Ala Arg Ala Ala Phe Gln Leu Gly Ser Pro Trp Arg Arg Met
            85              90              95
Asp Ala Ser His Arg Gly Arg Leu Leu Asn Arg Leu Ala Asp Leu Ile
            100             105             110
Glu Arg Asp Arg Thr Tyr Leu Ala Ala Leu Glu Thr Leu Asp Asn Gly
            115             120             125
Lys Pro Tyr Val Ile Ser Tyr Leu Val Asp Leu Asp Met Val Leu Lys
            130             135             140
Cys Leu Arg Tyr Tyr Ala Gly Trp Ala Asp Lys Tyr His Gly Lys Thr
145             150             155             160
Ile Pro Ile Asp Gly Asp Phe Phe Ser Tyr Thr Arg His Glu Pro Val
            165             170             175
Gly Val Cys Gly Gln Ile Ile Pro Trp Asn Phe Pro Leu Leu Met Gln
            180             185             190
Ala Trp Lys Leu Gly Pro Ala Leu Ala Thr Gly Asn Val Val Val Met
            195             200             205
Lys Val Ala Glu Gln Thr Pro Leu Thr Ala Leu Tyr Val Ala Asn Leu
            210             215             220
Ile Lys Glu Ala Gly Phe Pro Pro Gly Val Val Asn Ile Val Pro Gly
225             230             235             240
Phe Gly Pro Thr Ala Gly Ala Ala Ile Ala Ser His Glu Asp Val Asp
            245             250             255
Lys Val Ala Phe Thr Gly Ser Thr Glu Ile Gly Arg Val Ile Gln Val
            260             265             270
Ala Ala Gly Ser Ser Asn Leu Lys Arg Val Thr Leu Glu Leu Gly Gly
            275             280             285
Lys Ser Pro Asn Ile Ile Met Ser Asp Ala Asp Met Asp Trp Ala Val
            290             295             300
Glu Gln Ala His Phe Ala Leu Phe Phe Asn Gln Gly Gln Cys Cys Cys
305             310             315             320
Ala Gly Ser Arg Thr Phe Val Gln Glu Asp Ile Tyr Asp Glu Phe Val
            325             330             335
Glu Arg Ser Val Ala Arg Ala Lys Ser Arg Val Val Gly Asn Pro Phe
            340             345             350
Asp Ser Lys Thr Glu Gln Gly Pro Gln Val Asp Glu Thr Gln Phe Lys
            355             360             365
Lys Ile Leu Gly Tyr Ile Asn Thr Gly Lys Gln Glu Gly Ala Lys Leu
            370             375             380
Leu Cys Gly Gly Gly Ile Ala Ala Asp Arg Gly Tyr Phe Ile Gln Pro
385             390             395             400
Thr Val Phe Gly Asp Val Gln Asp Gly Met Thr Ile Ala Lys Glu Glu
            405             410             415
Ile Phe Gly Pro Val Met Gln Ile Leu Lys Phe Lys Thr Ile Glu Glu
            420             425             430
```

```
Val Val Gly Arg Ala Asn Asn Ser Thr Tyr Gly Leu Ala Ala Val
        435                 440                 445

Phe Thr Lys Asp Leu Asp Lys Ala Asn Tyr Leu Ser Gln Ala Leu Gln
450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Lys Val Lys Thr Val Thr Val Lys Val
            500                 505                 510

Pro Gln Lys Asn Ser
        515

<210> SEQ ID NO 3
<211> LENGTH: 501
<212> TYPE: PRT
<213> ORGANISM: Homo sapiens

<400> SEQUENCE: 3

Met Ser Ser Ser Gly Thr Pro Asp Leu Pro Val Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Ser Asp Leu Ala Gly Cys Ile Lys
        115                 120                 125

Thr Leu Arg Tyr Cys Ala Gly Trp Ala Asp Lys Ile Gln Gly Arg Thr
130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
```

```
                275                 280                 285
Glu Phe Ala His His Gly Val Phe Tyr His Gln Gly Gln Cys Cys Ile
290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
                340                 345                 350

Lys Ile Leu Asp Leu Ile Glu Ser Gly Lys Lys Glu Gly Ala Lys Leu
                355                 360                 365

Glu Cys Gly Gly Gly Pro Trp Gly Asn Lys Gly Tyr Phe Val Gln Pro
370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
                420                 425                 430

Phe Thr Lys Asp Ile Asp Lys Ala Ile Thr Ile Ser Ser Ala Leu Gln
                435                 440                 445

Ala Gly Thr Val Trp Val Asn Cys Tyr Gly Val Val Ser Ala Gln Cys
450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
                500

<210> SEQ ID NO 4
<211> LENGTH: 501
<212> TYPE: PRT
<213> ORGANISM: Homo sapiens

<400> SEQUENCE: 4

Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
                20                  25                  30

Val Ser Gly Lys Lys Phe Pro Val Phe Asn Pro Ala Thr Glu Glu Glu
                35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
                100                 105                 110

Lys Leu Tyr Ser Asn Ala Tyr Leu Asn Asp Leu Ala Gly Cys Ile Lys
                115                 120                 125

Thr Leu Arg Tyr Cys Ala Gly Trp Ala Asp Lys Ile Gln Gly Arg Thr
                130                 135                 140
```

```
Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
            165                 170                 175

Ile Trp Lys Ile Gly Pro Ala Leu Ser Cys Gly Asn Thr Val Val
            180                 185                 190

Lys Pro Ala Glu Gln Thr Pro Leu Thr Ala Leu His Val Ala Ser Leu
            195                 200                 205

Ile Lys Glu Ala Gly Phe Pro Pro Gly Val Val Asn Ile Val Pro Gly
        210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
            275                 280                 285

Glu Phe Ala His His Gly Val Phe Tyr His Gln Gly Gln Cys Cys Ile
290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Gly Gln Tyr Asp
            340                 345                 350

Lys Ile Leu Asp Leu Ile Glu Ser Gly Lys Lys Glu Gly Ala Lys Leu
            355                 360                 365

Glu Cys Gly Gly Gly Pro Trp Gly Asn Lys Gly Tyr Phe Val Gln Pro
            370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
            435                 440                 445

Ala Gly Thr Val Trp Val Asn Cys Tyr Gly Val Val Ser Ala Gln Cys
            450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 5
<211> LENGTH: 453
<212> TYPE: PRT
<213> ORGANISM: Homo sapiens

<400> SEQUENCE: 5

Met Ser Lys Ile Ser Glu Ala Val Lys Arg Ala Pro Ala Ala Phe Ser
1               5                   10                  15
```

```
Ser Gly Arg Thr Arg Pro Leu Gln Phe Arg Ile Gln Gln Leu Glu Ala
             20                  25                  30

Leu Gln Arg Leu Ile Gln Glu Gln Glu Gln Leu Val Gly Ala Leu
         35                  40                  45

Ala Ala Asp Leu His Lys Asn Glu Trp Asn Ala Tyr Tyr Glu Val
 50                  55                  60

Val Tyr Val Leu Glu Glu Ile Glu Tyr Met Ile Gln Lys Leu Pro Glu
 65                  70                  75                  80

Trp Ala Ala Asp Glu Pro Val Glu Lys Thr Pro Gln Thr Gln Gln Asp
                 85                  90                  95

Glu Leu Tyr Ile His Ser Glu Pro Leu Gly Val Val Leu Val Ile Gly
                100                 105                 110

Thr Trp Asn Tyr Pro Phe Asn Leu Thr Ile Gln Pro Met Val Gly Ala
            115                 120                 125

Ile Ala Ala Gly Asn Ser Val Val Leu Lys Pro Ser Glu Leu Ser Glu
130                 135                 140

Asn Met Ala Ser Leu Leu Ala Thr Ile Ile Pro Gln Tyr Leu Asp Lys
145                 150                 155                 160

Asp Leu Tyr Pro Val Ile Asn Gly Gly Val Pro Glu Thr Thr Glu Leu
                165                 170                 175

Leu Lys Glu Arg Phe Asp His Ile Leu Tyr Thr Gly Ser Thr Gly Val
            180                 185                 190

Gly Lys Ile Ile Met Thr Ala Ala Ala Lys His Leu Thr Pro Val Thr
        195                 200                 205

Leu Glu Leu Gly Gly Lys Ser Pro Cys Tyr Val Asp Lys Asn Cys Asp
    210                 215                 220

Leu Asp Val Ala Cys Arg Arg Ile Ala Trp Gly Lys Phe Met Asn Ser
225                 230                 235                 240

Gly Gln Thr Cys Val Ala Pro Asp Tyr Ile Leu Cys Asp Pro Ser Ile
                245                 250                 255

Gln Asn Gln Ile Val Glu Lys Leu Lys Lys Ser Leu Lys Glu Phe Tyr
            260                 265                 270

Gly Glu Asp Ala Lys Lys Ser Arg Asp Tyr Gly Arg Ile Ile Ser Ala
        275                 280                 285

Arg His Phe Gln Arg Val Met Gly Leu Ile Glu Gly Gln Lys Val Ala
    290                 295                 300

Tyr Gly Gly Thr Gly Asp Ala Ala Thr Arg Tyr Ile Ala Pro Thr Ile
305                 310                 315                 320

Leu Thr Asp Val Asp Pro Gln Ser Pro Val Met Gln Glu Glu Ile Phe
                325                 330                 335

Gly Pro Val Leu Pro Ile Val Cys Val Arg Ser Leu Glu Glu Ala Ile
            340                 345                 350

Gln Phe Ile Asn Gln Arg Glu Lys Pro Leu Ala Leu Tyr Met Phe Ser
        355                 360                 365

Ser Asn Asp Lys Val Ile Lys Lys Met Ile Ala Glu Thr Ser Ser Gly
    370                 375                 380

Gly Val Ala Ala Asn Asp Val Ile Val His Ile Thr Leu His Ser Leu
385                 390                 395                 400

Pro Phe Gly Gly Val Gly Asn Ser Gly Met Gly Ser Tyr His Gly Lys
                405                 410                 415

Lys Ser Phe Glu Thr Phe Ser His Arg Arg Ser Cys Leu Val Arg Pro
            420                 425                 430
```

```
Leu Met Asn Asp Glu Gly Leu Lys Val Arg Tyr Pro Pro Ser Pro Ala
            435                 440                 445

Lys Met Thr Gln His
    450

<210> SEQ ID NO 6
<211> LENGTH: 535
<212> TYPE: PRT
<213> ORGANISM: Homo sapiens

<400> SEQUENCE: 6

Met Ala Thr Cys Ile Trp Leu Arg Ser Cys Gly Ala Arg Arg Leu Gly
  1               5                  10                  15

Ser Thr Phe Pro Gly Cys Arg Leu Arg Pro Arg Ala Gly Gly Leu Val
                 20                  25                  30

Pro Ala Ser Gly Pro Ala Pro Gly Pro Ala Gln Leu Arg Cys Tyr Ala
             35                  40                  45

Gly Arg Leu Ala Gly Leu Ser Ala Ala Leu Leu Arg Thr Asp Ser Phe
 50                  55                  60

Val Gly Gly Arg Trp Leu Pro Ala Ala Thr Phe Pro Val Gln Asp
 65                  70                  75                  80

Pro Ala Ser Gly Ala Ala Leu Gly Met Val Ala Asp Cys Gly Val Arg
                 85                  90                  95

Glu Ala Arg Ala Ala Val Arg Ala Ala Tyr Glu Ala Phe Cys Arg Trp
                100                 105                 110

Arg Glu Val Ser Ala Lys Glu Arg Ser Ser Leu Leu Arg Lys Trp Tyr
                115                 120                 125

Asn Leu Met Ile Gln Asn Lys Asp Asp Leu Ala Arg Ile Ile Thr Ala
130                 135                 140

Glu Ser Gly Lys Pro Leu Lys Glu Ala His Gly Glu Ile Leu Tyr Ser
145                 150                 155                 160

Ala Phe Phe Leu Glu Trp Phe Ser Glu Glu Ala Arg Arg Val Tyr Gly
                165                 170                 175

Asp Ile Ile His Thr Pro Ala Lys Asp Arg Arg Ala Leu Val Leu Lys
                180                 185                 190

Gln Pro Ile Gly Val Ala Ala Val Ile Thr Pro Trp Asn Phe Pro Ser
            195                 200                 205

Ala Met Ile Thr Arg Lys Val Gly Ala Ala Leu Ala Ala Gly Cys Thr
210                 215                 220

Val Val Val Lys Pro Ala Glu Asp Thr Pro Phe Ser Ala Leu Ala Leu
225                 230                 235                 240

Ala Glu Leu Ala Ser Gln Ala Gly Ile Pro Ser Gly Val Tyr Asn Val
                245                 250                 255

Ile Pro Cys Ser Arg Lys Asn Ala Lys Glu Val Gly Glu Ala Ile Cys
                260                 265                 270

Thr Asp Pro Leu Val Ser Lys Ile Ser Phe Thr Gly Ser Thr Thr Thr
            275                 280                 285

Gly Lys Ile Leu Leu His His Ala Ala Asn Ser Val Lys Arg Val Ser
290                 295                 300

Met Glu Leu Gly Gly Leu Ala Pro Phe Ile Val Phe Asp Ser Ala Asn
305                 310                 315                 320

Val Asp Gln Ala Val Ala Gly Ala Met Ala Ser Lys Phe Arg Asn Thr
                325                 330                 335

Gly Gln Thr Cys Val Cys Ser Asn Gln Phe Leu Val Gln Arg Gly Ile
                340                 345                 350
```

```
His Asp Ala Phe Val Lys Ala Phe Ala Glu Ala Met Lys Lys Asn Leu
        355                 360                 365

Arg Val Gly Asn Gly Phe Glu Glu Gly Thr Thr Gln Gly Pro Leu Ile
    370                 375                 380

Asn Glu Lys Ala Val Glu Lys Val Glu Lys Gln Val Asn Asp Ala Val
385                 390                 395                 400

Ser Lys Gly Ala Thr Val Val Thr Gly Gly Lys Arg His Gln Leu Gly
                405                 410                 415

Lys Asn Phe Phe Glu Pro Thr Leu Leu Cys Asn Val Thr Gln Asp Met
            420                 425                 430

Leu Cys Thr His Glu Glu Thr Phe Gly Pro Leu Ala Pro Val Ile Lys
            435                 440                 445

Phe Asp Thr Glu Glu Glu Ala Ile Ala Ile Ala Asn Ala Ala Asp Val
    450                 455                 460

Gly Leu Ala Gly Tyr Phe Tyr Ser Gln Asp Pro Ala Gln Ile Trp Arg
465                 470                 475                 480

Val Ala Glu Gln Leu Glu Val Gly Met Val Gly Val Asn Glu Gly Leu
                485                 490                 495

Ile Ser Ser Val Glu Cys Pro Phe Gly Gly Val Lys Gln Ser Gly Leu
            500                 505                 510

Gly Arg Glu Gly Ser Lys Tyr Gly Ile Asp Glu Tyr Leu Glu Leu Lys
            515                 520                 525

Tyr Val Cys Tyr Gly Gly Leu
530                 535
```